United States Patent
Zheng et al.

(10) Patent No.: US 8,470,863 B2
(45) Date of Patent: *Jun. 25, 2013

(54) DERIVATIVES AND ANALOGS OF CHROMAN AS FUNCTIONALLY SELECTIVE ALPHA2C ADRENORECEPTOR AGONISTS

(75) Inventors: Junying Zheng, New Providence, NJ (US); Kevin D. McCormick, Basking Ridge, NJ (US); Jianhua Chao, San Diego, CA (US); Christopher W. Boyce, Flemington, NJ (US); Robert G. Aslanian, Rockaway, NJ (US); Younong Yu, East Brunswick, NJ (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 738 days.

This patent is subject to a terminal disclaimer.

(21) Appl. No.: 12/525,646

(22) PCT Filed: Feb. 11, 2008

(86) PCT No.: PCT/US2008/001770
§ 371 (c)(1),
(2), (4) Date: Mar. 12, 2010

(87) PCT Pub. No.: WO2008/100459
PCT Pub. Date: Aug. 21, 2008

(65) Prior Publication Data
US 2010/0168195 A1 Jul. 1, 2010

Related U.S. Application Data

(60) Provisional application No. 60/901,071, filed on Feb. 13, 2007, provisional application No. 60/972,892, filed on Sep. 17, 2007.

(51) Int. Cl.
*A61K 31/4178* (2006.01)
*C07D 233/64* (2006.01)

(52) U.S. Cl.
USPC ........................................ 514/397; 548/311.4

(58) Field of Classification Search
USPC ........................................ 514/397; 548/311.4
See application file for complete search history.

(56) References Cited

U.S. PATENT DOCUMENTS

| | | | |
|---|---|---|---|
| 5,658,938 | A | 8/1997 | Geerts et al. |
| 6,841,684 | B2 | 1/2005 | Chow et al. |
| 2003/0023098 | A1 | 1/2003 | Chow et al. |
| 2007/0093477 | A1 | 4/2007 | McCormick et al. |
| 2007/0099872 | A1 | 5/2007 | McCormick et al. |
| 2008/0027100 | A1 | 1/2008 | McCormick et al. |

FOREIGN PATENT DOCUMENTS

| | | |
|---|---|---|
| EP | 0 445 073 A | 9/1991 |
| EP | 1 170 288 A | 1/2002 |
| WO | WO 97/12874 | 4/1997 |
| WO | WO 99/28300 | 6/1999 |
| WO | WO 01/00586 | 1/2001 |
| WO | WO 02/076950 | 10/2002 |
| WO | WO 2005/034998 A3 | 4/2005 |
| WO | WO 2005/005781 | 11/2005 |
| WO | WO 2007/085556 | 8/2007 |
| WO | WO 2008/100456 A2 | 8/2008 |
| WO | WO 2008/100459 A1 | 8/2008 |
| WO | WO 2008/100463 A1 | 8/2008 |
| WO | WO 2008/100480 A1 | 8/2008 |

OTHER PUBLICATIONS

Byrn et al., Chapter 11 Hydrates and Solvates in Solid-State Chemistry of Drugs (2d Ed. 1999), 233-247.*
Ahlquist RP, "A Study of the Adrenotropic Receptors," Am. J. Physiol., (1948), pp. 586-600, vol. 153.
Bagley et al., "Synthesis and Alpha.2-adrenergic Activities of Imidazole and Imidazolidine analogues, in Vivtro and in Vivo Selectivity", Medicinal Chemistry Research, Birkhauser, Boston, US, (1994), pp. 346-364, vol. 4 No. 5.

(Continued)

*Primary Examiner* — Jason M Nolan
(74) *Attorney, Agent, or Firm* — H. Eric Fischer; Gerard M. Devlin

(57) ABSTRACT

In its many embodiments, the present invention provides a novel class of chroman compounds of formula I as α2C adrenergic receptor agonists, methods of preparing such compounds, pharmaceutical compositions containing one or more such compounds, methods of prepaxing pharmaceutical formulations comprising one or more such compounds, and methods of treatment, prevention, inhibition, or amelioration of one or more conditions associated with the α2C adrenergic receptors using such compounds or pharmaceutical compositions.

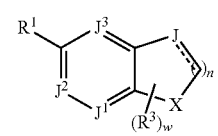

wherein
J is:

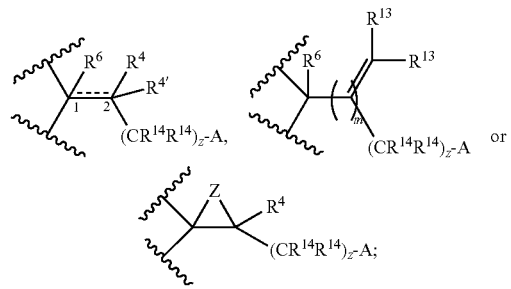

Z is —[C(R$^c$)(R$^c$)]$^x$—,
where
x is 1, 2, or 3.

14 Claims, No Drawings

OTHER PUBLICATIONS

Bousquet, P. et al., "Imidazoline Receptors: From Basic Concepts to Recent Developments", Journal of Cardiovascular Pharmacology, (1995), pp. S1-S6, (Suppl. 2). vol. 26.

Bousquet et al., "Role of the Ventral Surface of the Brain Stem in the Hypotensive Action of Clonidine", European Journal of Pharmacology, (1975), pp. 151-156, vol. 34.

Bruno et al., "The α2C-adrenergic receptor mediates hyperactivity of *cologoma* mice, a model of attention deficit hyperactivity disorder", Neurobiology of Disease, (2006), pp. 679-688, vol. 23.

Hong et al., "A Structure-Activity Relationship Study of Benzylic Modification of 4-[1-(1-Naphtyl)ethyl]-1*H*-imidazoles on α-2-Adrenergic Receptors", J. Med. Chem., (1994) pp. 2328-2333, vol. 37.

Lands et al., "Differentiation of Receptor Systems Activated by Sympathomimetic Amines", Nature, (1967), pp. 597-598, vol. 214.

MacDonald et al., "Gene Targeting—Homing in on Alpha2-Adrenoceptor-Subtype Function", TiPS, (1997), pp. 211-219, vol. 18.

Michel et al., "Classification of Alpha1-Adrenoceptor Subtypes", Naunyn-Schmiedeberg's Arch Pharmacol., (1995), pp. 1-10, vol. 352.

Reis et al., "The Imidazoline Receptor: Pharmacology, Functions, Ligands, and Relevance to Biology and Medicine", Annals of the New York Academy of Sciences, (1995), vol. 763, Table of Contents.

Yoo et al., "The Conformation and Activity of Benzofuran Derivatives as Angiotensin II Receptor Antagonists", Bioorganic & Medicinal Chemistry, (1997), pp. 445-459, vol. 5. No. 2.

Zhang et al., "Medetomidine Analogs as α2-Adrenergic Ligands. 2. Design, Synthesis, and Biological activity of Conformationally Restricted Naphthalene Derivatives of Medetomidine", J. Med. Chem., (1996), pp. 2001-3013, vol. 39.

Zhang et al., "Medetomidine Analogs as α2-Adrenergic Ligands. 3. Synthesis and Biological Evaluation of a New Series of Medetomidine Analogs and Their Potential Binding Interactions with α2-Adrenoceptors Involving a "Methyl Pocket"", J. Med. Chem., (1997), pp. 3014-3024, vol. 40.

International Search Report (PCT/US2008/001770) mail date Jul. 21, 2008, 6 pages.

* cited by examiner

DERIVATIVES AND ANALOGS OF CHROMAN AS FUNCTIONALLY SELECTIVE ALPHA2C ADRENORECEPTOR AGONISTS

RELATED APPLICATIONS

This application claims priority to U.S. application Ser. Nos. 60/901,071, filed on Feb. 13, 2007, and 60/972,892, filed on Sep. 17, 2007, both herein incorporated by reference.

FIELD OF THE INVENTION

The present invention relates to chroman compounds useful as α2C adrenergic receptor agonists, methods for making the compounds, pharmaceutical compositions containing the compounds, and methods of treatment and prevention using the compounds and compositions to treat disease states such as congestion (including nasal), migraine, congestive heart failure, cardiac ischemia, glaucoma, stress-induced urinary incontinence, attention deficit hyperactivity disorder, pain and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $\alpha_1$-Adrenoceptor Subtypes," Naunyn-Schmiedeberg's Arch. Pharmacol, 352:1-10 (1995); Macdonald et al., "Gene Targeting—Homing in on $\alpha_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art, and are described in numerous patents and scientific publications It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, attention deficit hyperactivity disorder and psychotic disorders.

For example, published PCT application WO 02/076950 discloses compounds having α2 agonist activity of the following general formula:

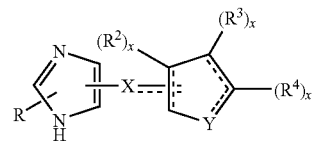

Other publications disclosing similar compounds includes WO 01/00586, WO 99/28300, U.S. Pat. No. 6,841,684 B2 and US 2003/0023098 A1.

Another class of compounds having α2-agonist properties is disclosed in U.S. Pat. No. 5,658,938, and has the following general formula:

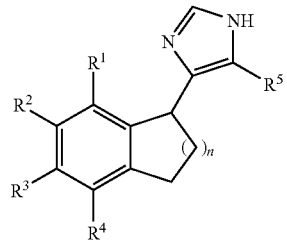

wherein n=1-2, $R^1$-$R^3$ represent hydrogen, halogen hydroxy, alkyl or alkoxy, and $R^5$ is hydrogen or alkyl.

Another class of compounds reported to have affinity for α2 receptors includes the following two compounds (Bagley et. al., Med. Chem. Res. 1994, 4:346-364):

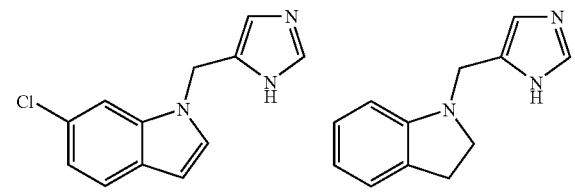 [SMILES: Clc1ccc2ccn(Cc3cnc[nH]3)c2c1 ; c1ccc2c(c1)CCN2Cc1cnc[nH]1]

An α2C-adrenergic receptor antagonist, yohimbine, was reported to have ameliorated hyperactivity of Coloboma mice, which are mice mutated to exhibit spontaneous hyperactivity. The α2C-andrenergic receptors were discussed as potential targets of pharmacotherapy for attention deficit hyperactivity disorder (ADHD). Bruno et al. Neurobiology of Disease 2006, 23: 679-688.

It is also known that compounds having adrenergic activity, such as α2A agonists, may be associated with undesirable side effects. Examples of such side effects include hyper- and hypotension, sedation, locomotor activity, and body temperature variations.

Another class of compounds reported to have affinity for α2 receptors includes the following two compounds (Miller et. al., *J. Med. Chem.* 1994, 37:2328-2333; *J. Med. Chem.* 1996, 39:3001-3013; *J. Med. Chem.* 1997, 37:3014-3024):

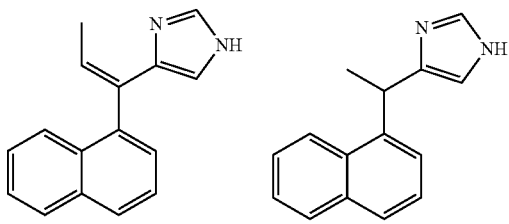 [SMILES: C/C=C(\c1c[nH]cn1)c1cccc2ccccc12 ; CC(c1c[nH]cn1)c1cccc2ccccc12]

Another class of indane and tetrahyrdonaphthalene type compounds having α2-agonist properties is disclosed in PCT application WO 97/12874 and WO20040506356 This class has the following general formula:

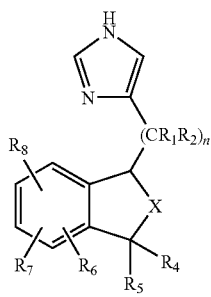

wherein n=0-1, X is 1 or 2 carbon units, $R_4$ is H, OH, alkyl, or alkoxy, $R_5$ may be taken together with $R^4$ to form a carbonyl, and $R^6$-$R^8$=H, OH, SH, alkyl, alkenyl, cycloalkyl, alkoxy, hydroxyalkyl, alkylthio, alkylthiol, halo, $CF_3$, $NO_2$, or alkylamino. This class specifically includes MPV-2426 (fadolmidine) and its prodrug esters:

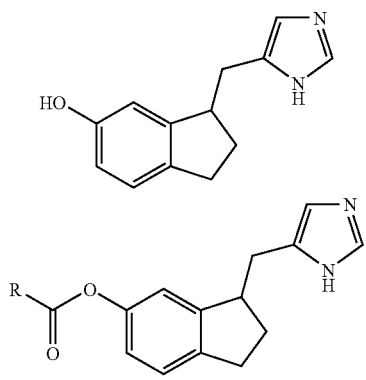

wherein R is optionally substituted lower alkyl, aryl, cycloalkyl, heteroaryl, lower alkylamino, and saturated. 5- or 6-membered heterocyclic groups containing. 1 or 2 N atoms.

Further, other classes of compounds that exhibit functional selectivity for the alpha 2C receptor have been discovered. Application U.S. Ser. No. 11/508,458, filed Aug. 23, 2006, discloses indoline compounds that possess this activity and application U.S. Ser. No. 11/508,467, filed on the same date, describes morpholine compounds that are functionally selective of the alpha 2C receptor. CIP applications of these applications have been filed; the Ser. Nos. 11/705,673 and 11/705,683, both filed on Feb. 13, 2009.

Additional applications filed concurrently herewith that disclose alpha2C receptor agonists are application U.S. Ser. No. 12/525,641, which claims priority to provisional application USSN 60/901,045, (AL06619) and application U.S. Ser. No. 12/525,648 (now US Patent No. 8,017,642), which claims priority to provisional application USSN 60/901,064 (AL06621).

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype and that act functionally selectively as agonists of the α2C or the α2B/2C receptor subtype in preference over the α2A receptor subtype possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is ≧30% $E_{max}$ (GTPγS assay) and its efficacy at the α2A receptor is ≦35% $E_{max}$, with an efficacy at the α2A receptor ≦33% $E_{max}$ preferred (GTPγS assay).

It has been reported in PCT application WO 05/034998 A3 that coadministration of 2 components, one of which activates an alpha 2 adrenergic receptor and the other an alpha 1 adrenergic receptor antagonist, has resulted in an increased potency of the therapeutic activity of the first component without significantly increasing its sedative activity.

There is a need for new compounds, formulations, treatments and therapies to treat diseases and disorders associated with α2C adrenergic receptors while minimizing adverse side effects. Further, there is a need to develop compounds that are functionally selective for the α2C or the α2B/2C receptor subtype with respect to the α2A receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as functionally selective α2C adrenergic receptor agonists, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts or metabolites, solvates, prodrugs or polymorphs of said compound, said compound having the general Formula I:

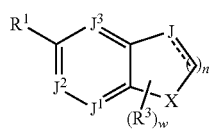

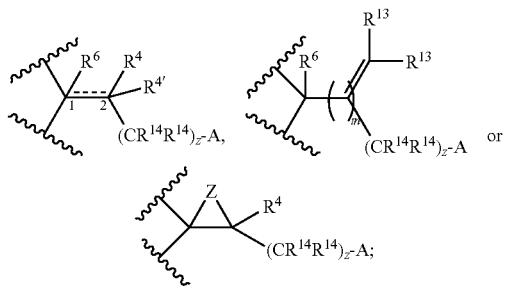

wherein:

J is:

Z is —[C(R$^c$)(R$^c$)]$_x$—, where x is 1, 2, or 3;

A is a 5-membered heteroaryl, heterocyclyl or heterocyclenyl ring containing 1-3 heteroatoms, and is optionally substituted with at least one R$^5$ and/or 1 or 2 (=O) groups;

J$^1$, J$^2$, and J$^3$ are independently —N—, —N(O)— or —C(R$^2$)—;

X is —O— or —S—;

----- is a single or double bond provided that there cannot be two continuous double bonds and further provided that when position 1 and 2 form a double bond in Formula I, R$^{4'}$ and R$^6$ are not present;

R$^1$ is selected from the group consisting of —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —[C(R$^a$)(R$^b$)]$_q$N(YR$^7$)(YR$^{7'}$), —[C(R$^a$)(R$^b$)]$_q$ON=CR$^7$R$^{7'}$, —P(=O)(OR$^7$)(OR$^{7'}$), —P(=O)(NR$^7$R$^{7'}$)$_2$, and —P(=O)R$^8$$_2$;

Y is selected from the group consisting of a bond, —C(=O)—, —C(=O)NR$^7$—, —C(=O)O—, —C(=O)—[C(R$^a$)(R$^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)NR$^7$O—, —S(O)$_p$—, —SO$_2$NR$^7$—, and —C(=S)NR$^7$—;

wherein R$^a$ and R$^b$ are independently selected from the group consisting of H, alkyl, alkoxy, and halo, and R$^c$ is H or alkyl;

R$^2$ is independently selected from the group consisting of H, —OH, halo, —CN, —NO$_2$, —S(O)$_p$R$^7$, —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)])=$_q$OYR$^{7'}$, and —(CH$_2$)$_q$ON=CR$^7$R$^{7'}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

R$^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least R$^5$, provided that when w is 3, no more than 2 of the R$^3$ groups may be (=O);

R$^4$ is independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

R$^{4'}$ is absent or independently selected from the group consisting of H, and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

R$^5$ is independently selected from the group consisting of H, halo, and —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O);

R$^6$ is absent or independently selected from the group consisting of H, —CN, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

R$^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by R$^{12}$;

R$^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by R$^{12}$; or a) when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —(CH$_2$)$_q$NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O);

R$^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$, and —S(O)$_p$R$^{11}$ substituents and/or 1 or 2 (=O);

R$^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O);

R$^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O);

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11'}$)$_2$, and —S(O)$_p$R$^{11'}$ substituents and/or 1 or 2 (=O);

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more times by R$^{11}$;

R$^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

R$^{14}$ is independently selected from the group consisting of H, alkyl, halo, —CN, and alkoxy;

m is 0 or 1;
n is independently 1, 2, or 3;
p is independently 0, 1, or 2;
q is independently an integer from 0-10;
w is 0, 1, 2, or 3; and
z is 0, 1, 2, 3, 4, or 55, with the following provisos:

(a) if J$^1$-J$^3$ are —C(H)—, R$^1$ is —[C(R$^a$)(R$^b$)]$_q$OYR$^{7'}$, q is 0, and A is unsubstituted imidazolyl, then Y is other than a bond;

(b) if J$^1$-J$^3$ are —C(H)—, R$^1$ is —[C(R$^a$)(R$^b$)]$_q$YR$^{7'}$, q is 0, and A is unsubstituted imidazolyl, then Y is other than a bond;

(c) if m is 0 then z cannot be zero;

(d) if A is unsubstituted imidazolyl, R$^1$ is —[C(R$^a$)(R$^b$)]$_q$ YR$^{7'}$, q is 0, Y is —C(=O)— or —C(=O)O—, then R$^{7'}$ is other than H or alkyl;

(e) if R$^1$ is —[C(R$^a$)(R$^b$)]$_q$YR$^{7'}$, q=0, and Y=—C(=NR$^7$)—, —C(=NOR$^7$)—, —C(=NR$^7$)NR$^7$—, or —C(=NR$^7$)N(R$^c$)O—, then R$^7$ and R$^{7'}$ may not be taken together to form a 3- to 8-membered heterocyclyl, heterocyclenyl or heteroaryl ring; and (f) if R$^1$ is —[C(R$^a$)(R$^b$)]$_q$N(R$^7$)YR$^{7'}$ or —[C(R$^a$)(R$^b$)]$_q$NR$^7$R$^{7'}$ and q=0, then R$^7$ and R$^{7'}$ may not be taken together to form a 3- to 8-membered heterocyclyl, heterocyclenyl or heteroaryl ring.

Compounds described in the present application include a compound, or pharmaceutically acceptable salts or metabolites, solvates, prodrugs or polymorphs of said compound, said compound having the general structure shown in Formulae Ia or Ib:

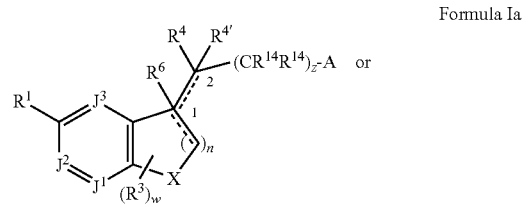

Formula Ia

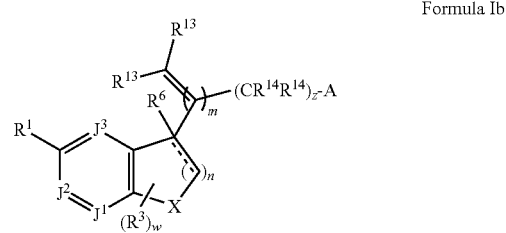

Formula Ib wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) R$^5$ and/or 1 or 2 (=O) (carbonyl) groups;

J$^1$, J$^2$, and J$^3$ are independently —N—, —N(O)— or —C(R$^2$)—;

X is —O— or —S—;

- - - - - is a single or double bond provided that there cannot be two continuous double bonds and further provided that when position 1 and 2 form a double bond in Formula Ia, R$^{4'}$ and R$^6$ are not present;

R$^1$ is selected from the group consisting of —[C(R$^a$)(R$^b$)]$_q$ YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —[C(R$^a$)(R$^b$)]$_q$N(YR$^7$)(YR$^{7'}$), —[C(R$^a$)(R$^b$)]$_q$ON=CR$^7$R$^{7'}$, —P(=O)(OR$^7$)(OR$^{7'}$), —P(=O)(NR$^7$R$^{7'}$)$_2$, and —P(=O)R$^8{}_2$;

Y is selected from the group consisting of a bond, —C(=O)—, —C(=O)NR$^7$—, —C(=O)O—, —C(=O)—[C(R$^a$)(R$^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)NR$^7$O—, —S(O)$_p$—, —SO$_2$NR$^7$—, and —C(=S)NR$^7$—;

wherein R$^a$ and R$^b$ are independently selected from the group consisting of H, alkyl, alkoxy, and halo, and R$^c$ is H or alkyl;

R$^2$ is independently selected from the group consisting of H, —OH, halo, —CN, —NO$_2$, —S(O)$_p$R$^7$, —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]=$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

$R^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^4$ is independently selected from the group consisting of H, halo and —CN, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or independently selected from the group consisting of H, and halo —CN, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O);

$R^6$ is absent or independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

or $R^4$ and $R^6$ taken together with the carbon atoms to which they are attached form a 3- to 6-membered cycloalkyl, cycloalkenyl, hetrocyclyl or heterocyclylalkenyl ring, wherein said rings may be optionally substituted one or more times (preferably 1 to 5, more preferably 1 to 3) by $R^5$ and/or 1 or 2 (=O);

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$; or a) when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7''}$, —(CH$_2$)$_q$NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^7$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^5$ moieties and/or 1 or 2 (=O);

$R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O);

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

$R^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{14}$ is independently selected from the group consisting of H, alkyl, halo, —CN, and alkoxy;

m is 0 or 1;

n is independently and integer from −3;

p is independently an integer from 0-2;

q is independently an integer from 0-10;

w is and integer from 1-3; and z is an integer from 0 to 5, with the following provisos:

(a) if $J^1$-$J^3$ are —C(H)—, $R^1$ is —[C($R^a$)($R^b$)]$_q$OY$R^{7'}$, q is 0, and A is unsubstituted imidazolyl, then Y is other than a bond;

(b) if $J^1$-$J^3$ are —C(H)—, $R^1$ is —[C($R^a$)($R^b$)]$_q$Y$R^{7'}$, q is 0, and A is unsubstituted imidazolyl, then Y is other than a bond;

(c) if m is 0 then z cannot be zero;

(d) if A is unsubstituted imidazolyl, $R^1$ is —[C($R^a$)($R^b$)]$_q$Y$R^{7'}$, q is 0, Y is —C(═O)— or —C(═O)O—, then $R^{7'}$ is other than H or alkyl;

(e) if $R^1$ is —[C($R^a$)($R^b$)]$_q$Y$R^{7'}$, q=0, and Y═—C(═N$R^7$)—, —C(═NO$R^7$)—, —C(═N$R^7$)N$R^7$—, or —C(═N$R^7$)N($R^c$)O—, then $R^7$ and $R^{7'}$ may not be taken together to form a 3- to 8-membered heterocyclyl, heterocyclenyl or heteroaryl ring; and (f) if $R^1$ is —[C($R^a$)($R^b$)]$_q$N($R^7$)Y$R^{7'}$ or —[C($R^a$)($R^b$)]$_q$N$R^7R^{7'}$ and q=0, then $R^7$ and $R^{7'}$ may not be taken together to form a 3- to 8-membered heterocyclyl, heterocyclenyl or heteroaryl ring.

The compounds of Formula I (including those of Ia and IIb) can be useful as α2C adrenergic receptor agonists, and can be useful in the treatment and prevention of allergic rhinitis, congestion (including, but not limited to nasal congestion), migraine, congestive heart failure, chronic heart failure, cardiac ischemia, glaucoma, stress-induced urinary incontinence, attention deficit hyperactivity disorder, neuronal damage from ischemia and psychotic disorders. Further, the compounds of Formula I (including those of Ia and Ib) can be useful in the treatment of pain (both chronic and acute), such as pain that is caused by inflammation, neuropathy, arthritis (including osteo and rheumatoid arthritis), diabetes (e.g., diabetes mellitus or diabetes insipidus) or pain of an unknown origin. Examples of neuropathic pain may include but not limited to; diabetic neuropathy, neuralgia of any etiology (e.g. post-herpetic, trigeminal), chemotherapy-induced neuropathy, HIV, lower back pain of neuropathic origin (e.g. sciatica), traumatic peripheral nerve injury of any etiology, central pain (e.g. post-stroke, thalamic, spinal nerve injury). Other pain that can be treated is nociceptive pain and pain that is visceral in origin or pain that is secondary to inflammation or nerve damage in other diseases or diseases of unknown origin. Further, these compounds can be useful in the treatment of symptoms of diabetes. Examples of symptoms of diabetes may include but are not limited to: hyperglycemia, hypertriglyceridemia, increased levels of blood insulin and hyperlipidemia.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to the mammal an effective dose of at least one compound having adrenergic activity wherein said compound is a functionally selective agonist of the α2C receptor, wherein the selective agonist of the α2c receptor has an efficacy that is greater than or equal to 30% $E_{max}$ when assayed in the GTPγS assay and its efficacy at the α2A receptor is ≦35% $E_{max}$ (GTPγS assay).

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In one embodiment, if $J^1$-$J^3$ are —C(H)—, $R^1$ is —[C($R^a$)($R^b$)]$_q$OY$R^{7'}$, q is 0, and A is unsubstituted imidazolyl, then Y is other than a bond.

In another embodiment, if $J^1$-$J^3$ are —C(H)—, $R^1$ is —[C($R^a$)($R^b$)]$_q$Y$R^{7'}$, q is 0, and A is unsubstituted imidazolyl, then Y is other than a bond.

In another embodiment, $J^1$-$J^3$ are each —C($R^2$)—.

In another embodiment one of $J^1$-$J^3$ is —N— while the other two variables are each —C($R^2$)—.

In another embodiment A is an optionally substituted 5-membered heteroaryl, heterocyclenyl or heterocyclyl ring. Preferred optionally substituted heteroaryl, heterocyclenyl or heterocyclyl 5-membered rings include, for example, imidazole, thiazole, pyrrole, isoxazole, oxazole, isothiazole, pyrazole, imadazoline, imidazol-2-one, imidazol-2-thione, 2-aminoimidazoline, oxazoline, oxazol-2-one, oxazol-2-thione, 2-aminooxazoline, thiazoline, thiazol-2-one, thiazol-2-thione, 2-aminothiazoline, pyrroline, pyrazoline, pyrrolidine, imidazolidine, and pyrazolidine. A more preferred set of 5-membered rings includes: imidazole, imadazoline, imidazol-2-one, imidazol-2-thione, 2-aminoimidazoline, oxazoline, oxazol-2-one, oxazol-2-thione, and 2-aminooxazoline. A most preferred set of 5-memebered rings includes imidazole. Optionally substituents include any of the "ring system substituents" identified below.

In another embodiment, $R^1$ is selected from —(CH$_2$)$_q$Y$R^{7'}$, —(CH$_2$)$_q$N($R^7$)Y$R^{7'}$, —(CH$_2$)$_q$N(Y$R^7$)(Y$^{7'}$), —(CH$_2$)$_q$N$R^7R^{7'}$, —(CH$_2$)$_q$OY$R^{7'}$, —(CH$_2$)$_q$ON═C$R^7R^{7'}$, —P(═O)(O$R^7$)(O$R^{7'}$), —P(═O)(N$R^7R^{7'}$), and —P(═O)$R^8{}_2$.

In another embodiment, Y is selected from a bond, —C(═O)—, —C(═O)N$R^7$—, —C(═O)O—, —C(═N$R^7$)—, —C(═NO$R^7$)—, —C(═N$R^7$)N$R^7$—, —C(═N$R^7$)N$R^7$O—, —S(O)$_p$—, —SO$_2$N$R^7$—, and —C(═S)N$R^7$—.

In another embodiment, $R^2$ is independently selected from the group consisting of H, —OH, halo, —CN, —NO$_2$, —S(O)$_p R^7$, —N$R^7R^{7'}$, —(CH$_2$)$_q$Y$R^{7'}$, —(CH$_2$)$_q$N($R^7$)Y$R^{7'}$, —(CH$_2$)$_q$OY$R^{7'}$, —(CH$_2$)$_q$ON═C$R^7R^{7'}$, —P(═O)(O$R^7$)(O$R^{7'}$), —P(═O)N$R^7R^{7'}$, and —P(═O)$R^8{}_2$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^3$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^4$ is independently selected from H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^{4'}$ is independently selected from H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, in Formula I, atoms $R^{4'}$ and $R^6$ are not present and atoms 1 and 2 form a double bond with a trans configuaration relative to the $CR^{14}R^{14})_z$-A and the bicyclic ring.

In another embodiment, in Formula I, atoms $R^{4'}$ and $R^6$ are not present and atoms 1 and 2 form a double bond with a cis configuration relative to the $—CR^{14}R^{14})_z$-A and the bicyclic ring.

In another embodiment, in Formula I, atoms 1 and 2 do not form a double bond and $R^{4'}$ exists.

In another embodiment, $R^5$ is independently selected from H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5) of halo, —OH, —CN, —NO$_2$, —NR$^7$R$^{7'}$, and —S(O)$_p$R$^7$ substituents.

In another embodiment, $R^6$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents, and —C(=O)R$^7$, —C(=O)OR$^7$, —C(=O)NR$^7$R$^{7'}$, —SO$_2$R$^7$ and —SO$_2$NR$^7$R$^{7'}$.

In another embodiment, Z is —(CH$_2$)—.

In another embodiment, $R^7$ or $R^{7'}$ is independently selected from H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$, and —S(O)$_p$R$^{11}$ substituents.

In another embodiment, when a variable is —NR$^7$R$^{7'}$, —(CH$_2$)$_q$NR$^7$R$^{7'}$, —P(O)NR$^7$R$^{7'}$, —C(O)NR$^7$R$^{7'}$ or —SO$_2$NR$^7$R$^{7'}$, R$^7$ and R$^{7'}$ together with the N atom to which they are attached form a aziridine, azetidine, pyrrole, pyrrolidine, piperidine, piperazine or morpholine ring, each of which are optionally substituted by $R^5$.

In another embodiment, $R^8$ is independently selected from alkyl, alkenyl, alkynyl, cycloalkyl, aryl, arylalkyl, heterocyclyl, heteroaryl, and heteroarylalkyl groups, each of which is optionally substituted with at least one (preferably 1 to 5) of halo, alkoxy, —OH, —CN, —NO$_2$, —N(R$^{11}$)$_2$, and —S(O)$_p$R$^{11}$ substituents.

In another embodiment $R^{12}$ is independently selected from the group consisting of alkyl, halo, haloalkyl, nitro, cyano, hydroxyl, amino, alkylamino, dialkylamino and alkoxy.

In another embodiment $R^{14}$ is independently selected from H or alkyl.

In another embodiment A is unsubstituted imidazole, $J^1$-$J^2$ are —C(H)—, $J^3$ is —N— or —C(H)—, $R^3$ is H, $R^4$ is H, halo or alkyl, $R^6$ is H, n is 1 or 2, and z is 0.

In another embodiment A is unsubstituted imidazole, $J^1$-$J^2$ are —C(H)—, $J^3$ is —N— or —C(H)—, $R^3$ is H, $R^4$ is H, halo or alkyl, $R^6$ is H, $R^{14}$ is H, alkyl or halo, n is 1 or 2, and z is 1-3.

In another embodiment A is unsubstituted imidazole, $J^1$-$J^2$ are —C(H)—, $J^3$ is —N— or —C(H)—, $R^3$ is H, $R^6$ is H, $R^{13}$ is H or alkyl, m is 1, n is 1 or 2, and z is 0.

In another embodiment A is unsubstituted imidazole, $J^1$-$J^2$ are —C(H)—, $J^3$ is —N— or —C(H)—, $R^3$ is H, $R^6$ is H, $R^{13}$ is H or alkyl, $R^{14}$ is H, alkyl or halo, m is 1, n is 1 or 2, and z is 1-3.

In another embodiment, m is 1.
In another embodiment, n is 1.
In another embodiment, p is 0-2.
In another embodiment, q is 0-3.
In another embodiment, A is imidazolyl.

In another embodiment, the present invention discloses compounds which are represented by structural Formula Ia

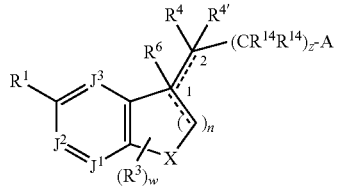

Formula Ia or a pharmaceutically acceptable salt, ester, or solvate thereof wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl) groups;

$J^1$, $J^2$, and $J^3$ are independently —N—, —N(O)— or —C(R$^2$)—;

X is —O— or —S—;

----- is a single or double bond provided that there cannot be two continuous double bonds and further provided that when position 1 and 2 form a double bond in Formula Ia, $R^{4'}$ and $R^6$ are not present;

$R^1$ is selected from the group consisting of —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$PYR$^{7'}$, —[C(R$^a$)(R$^b$)]$_q$N(YR$^7$)(YR$^{7'}$), —[C(R$^a$)(R$^b$)]$_q$ON=CR$^7$R$^{7'}$, —P(=O)(OR$^7$)(OR$^7$), —P(=O)(NR$^7$R$^{7'}$)$_2$, and —P(=O)R$^8{}_2$;

Y is selected from the group consisting of a bond, —C(=O)—, —C(=O)NR$^7$—, —C(=O)O—, —C(=O)—[C(R$^a$)(R$^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)NR$^7$O—, —S(O)$_p$—, —SO$_2$NR$^7$—, and —C(=S)NR$^7$—;

wherein $R^a$ and $R^b$ are independently selected from the group consisting of H, alkyl, alkoxy, and halo, and $R^c$ is H or alkyl;

$R^2$ is independently selected from the group consisting of H, —OH, halo, —CN, —NO$_2$, —S(O)$_p$R$^7$, —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]=$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^4$ is independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or independently selected from the group consisting of H, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O);

$R^6$ is absent or independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$; or a) when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7''}$, —(CH$_2$)$_q$NR$^7$R$^{7'}$, —C(O)NR$^7$R$^{7'}$ or —SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^5$ moieties and/or 1 or 2 (=O);

$R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O);

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by $R^{11}$;

$R^{14}$ is independently selected from the group consisting of H, alkyl, halo, —CN, and alkoxy;

m is 0 or 1;
n is independently 1, 2, or 3;
p is independently 0, 1, or 2;
q is independently an integer from 0-10;
w is 0, 1, 2, or 3; and
z is 0, 1, 2, 3, 4, or 5,
with the following provisos:

(a) if $J^1$-$J^3$ are —C(H)—, $R^1$ is —[C($R^a$)($R^b$)]$_q$OY$R^{7'}$, q is 0, and A is unsubstituted imidazolyl, then Y is other than a bond;

(b) if $J^1$-$J^3$ are —C(H)—, $R^1$ is —[C($R^a$)($R^b$)]$_q$OY$R^{7'}$, q is 0, and A is unsubstituted imidazolyl, then Y is other than a bond;

(c) if m is 0 then z cannot be zero;

(d) if A is unsubstituted imidazolyl, $R^1$ is —[C($R^a$)($R^b$)]$_q$Y$R^{7'}$, q is 0, Y is —C(=O)— or C(=O)O—, then $R^{7'}$ is other than H or alkyl;

(e) if $R^1$ is —[C($R^a$)($R^b$)]$_q$Y$R^{7'}$, q=0, and Y=—C(=N$R^7$)—, —C(=NO$R^7$)—, —C(=N$R^7$)N$R^7$—, or —C(=N$R^7$)N($R^c$)O—, then $R^7$ and $R^{7'}$ may not be taken together to form a 3- to 8-membered heterocyclyl, heterocyclenyl or heteroaryl ring; and (f) if $R^1$ is —[C($R^a$)($R^b$)]$_q$N($R^7$)Y$R^{7'}$ or —[C($R^a$)($R^b$)]$_q$N$R^7R^{7'}$ and q=0, then $R^7$ and $R^{7'}$ may not be taken together to form a 3- to 8-membered heterocyclyl, heterocyclenyl or heteroaryl ring.

In another embodiment of Formula Ia, the present invention discloses compounds which are represented by structural Formula II

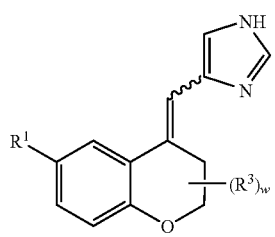

II or a pharmaceutically acceptable salt, ester, or solvate thereof, wherein the definitions are the same as in Formula I and "~~~" indicates a cis or trans double bond configuration between the imidazole ring and the bicyclic chroman ring.

Preferred compounds of Formula II are those wherein:

$R^1$ is —(CH$_2$)$_q$Y$R^{7'}$, —(CH$_2$)$_q$N$R^7$Y$R^{7'}$ or —(CH$_2$)$_q$N(Y$R^7$)(Y$R^{7'}$);

Y is a bond —C(=O)—, —C(=O)N$R^7$—, —C(=O)O—, or —S(O)$_p$—;

$R^7$ is H, alkyl (preferably $C_1$-$C_5$), cycloalkyl, cycloalkylalkyl, optionally substituted phenyl, optionally substituted benzyl, optionally substituted pyridyl, optionally substituted pyrimidyl, optionally substituted tetrahydropyranyl, wherein the optional substituents are halogen, cyano, alkyl, alkoxy, nitro, amino, alkylamino, dialkylamino and —S(O)$_p$alkyl, where p is 0, 1, or 2;

$R^{7'}$ is H, alkyl (preferably $C_1$-$C_5$), cycloalkyl, cycloalkylalkyl, optionally substituted phenyl, optionally substituted benzyl, optionally substituted pyridyl, optionally substituted pyrimidyl, optionally substituted tetrahydropyranyl, wherein the optional substituents are halogen, cyano, alkyl, nitro, amino, alkylamino, dialkylamino and —S(O)$_p$alkyl, where p is 0, 1, or 2

In another embodiment, the present invention discloses compounds which are represented by structural Formula Ib

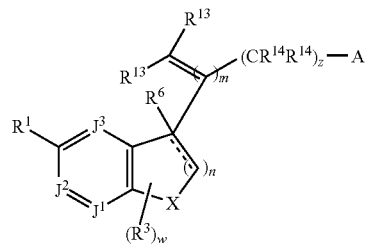

Formula Ib or a pharmaceutically acceptable salt, ester, or solvate thereof wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl) groups;

$J^1$, $J^2$, and $J^3$ are independently —N—, —N(O)— or —C($R^2$)—;

X is —O— or —S—;

⁃ ⁃ ⁃ ⁃ ⁃ is a single or double bond provided that there cannot be two continuous double bonds and further provided that when position 1 and 2 form a double bond in Formula Ia, $R^{4'}$ and $R^6$ are not present;

$R^1$ is selected from the group consisting of —[C($R^a$)($R^b$)]$_q$Y$R^{7'}$, —[C($R^a$)($R^b$)]$_q$N($R^7$)Y$R^{7'}$, —[C($R^a$)($R^b$)]$_q$N$R^7R^{7'}$, —[C($R^a$)($R^b$)]$_q$OY$R^{7'}$, —[C($R^a$)($R^b$)]$_q$N(Y$R^7$)(Y$R^{7'}$), —[C($R^a$)($R^b$)]$_q$ON=C$R^7R^{7'}$, —P(=O)(O$R^7$)(O$R^{7'}$), —P(=O)(N$R^7R^{7'}$)$_2$, and —P(=O)$R^8_2$;

Y is selected from the group consisting of a bond, —C(=O)—, —C(=O)N$R^7$—, —C(=O)O—, —C(=O)—[C($R^a$)($R^b$)]$_n$—O—C(=O)—, —C(=O)N($R^c$)—O—, —C(=N$R^7$)—, —C(=NO$R^7$)—, —C(=N$R^7$)N$R^7$—, —C(=N$R^7$)N$R^7$O—, —S(O)$_p$—, —SO$_2$N$R^7$—, and —C(=S)N$R^7$—;

wherein $R^a$ and $R^b$ are independently selected from the group consisting of H, alkyl, alkoxy, and halo, and $R^c$ is H or alkyl;

$R^2$ is independently selected from the group consisting of H, —OH, halo, —CN, —NO$_2$, —S(O)$_p$$R^7$, —N$R^7R^{7'}$, —[C($R^a$)($R^b$)]$_q$Y$R^{7'}$, —[C($R^a$)($R^b$)]$_q$N($R^7$)Y$R^{7'}$, —[C($R^a$)($R^b$)]=$_q$OY$R^{7'}$, and —(CH$_2$)$_q$ON=C$R^7R^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^5$ is independently selected from the group consisting of H, halo, —OH, —CN, —NO$_2$, —N$R^7R^{7'}$, and —S(O)$_p$$R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —N$R^7R^{7'}$, and —S(O)$_p$$R^7$ substituents and/or 1 or 2 (=O);

$R^6$ is absent or independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

R$^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetroclenyl, hetrocyclenylalkyl, heteroaryl, and heteroarylalkyl groups, each of which is optionally substituted one or more times (preferably 1 to 5, more preferably 1 to 3) by R$^{12}$;

R$^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetroclenyl, hetrocyclenylalkyl, heteroaryl, and heteroarylalkyl groups, each of which is optionally substituted one or more times (preferably 1 to 5, more preferably 1 to 3) by R$^{12}$; or when a) when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —(CH$_2$)$_q$NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O);

R$^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O), R$^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

R$^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11}$ substituents and/or 1 or 2 (=O);

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

R$^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

R$^{14}$ is independently selected from the group consisting of H, alkyl, halo, —CN, and alkoxy;

m is 0 or 1;
n is independently 1, 2, or 3;
p is independently 0, 1, 2, or 2;
q is independently an integer from 0-10;
w is 0, 1, 2, or 3; and
z is 0, 1, 2, 3, 4, or 5, with the following provisos:

(a) if J$^1$-J$^3$ are —C(H)—, R$^1$ is —[C(R$^a$)(R$^b$)]$_q$PYR$^{7'}$, q is 0, and A is unsubstituted imidazolyl, then Y is other than a bond;

(b) if J$^1$-J$^3$ are —C(H)—, R$^1$ is —[C(R$^a$)(R$^b$)]$_q$YR$^{7'}$, q is 0, and A is unsubstituted imidazolyl, then Y is other than a bond;

(c) if m is 0 then z cannot be zero;

(d) if A is unsubstituted imidazolyl, R$^1$ is —[C(R$^a$)(R$^b$)]$_q$YR$^{7'}$, q is 0, Y is —C(=O)— or —C(=O)O—, then R$^{7'}$ is other than H or alkyl;

(e) if R$^1$ is —[C(R$^a$)(R$^b$)]$_q$YR$^{7'}$, q=0, and Y=—C(=NR$^7$)—, —C(=NOR$^7$)—, —C(=NR$^7$)NR$^7$—, or —C(=NR$^7$)N(R$^c$)O—, then R$^7$ and R$^{7'}$ may not be taken together to form a 3- to 8-membered heterocyclyl, heterocyclenyl or heteroaryl ring; and (f) if R$^1$ is —[C(R$^a$)(R$^b$)]$_q$N(R$^7$)YR$^{7'}$ or —[C(R$^a$)(R$^b$)]$_q$NR$^7$R$^{7'}$ and q=0, then R$^7$ and R$^{7'}$ may not be taken together to form a 3- to 8-membered heterocyclyl, heterocyclenyl or heteroaryl ring.

Preferred compounds of formulae Ia and Ib are those wherein:

R$^1$ is —(CH$_2$)$_q$YR$^{7'}$, —(CH$_2$)$_q$NR$^7$YR$^{7'}$ or —(CH$_2$)$_q$N(YR$^7$)(YR$^{7'}$);

Y is a —C(=O)—, —C(=O)NR$^7$—, —C(=O)O—, —S(O)$_p$—, and —SO$_2$NR$^7$;

$R^7$ is H, alkyl (preferably $C_1$-$C_5$), cycloalkyl, cycloalkylalkyl, optionally substituted phenyl, optionally substituted benzyl, optionally substituted pyridyl, optionally substituted pyrimidyl, optionally substituted tetrahydropyranyl, wherein the optional substituents are halogen, cyano, alkyl, alkoxy, nitro, amino, alkylamino, dialkylamino and —S(O)$_p$alkyl, where p is 0, 1, or 2;

$R^{7'}$ is H, alkyl (preferably $C_1$-$C_5$), cycloalkyl, cycloalkylalkyl, optionally substituted phenyl, optionally substituted benzyl, optionally substituted pyridyl, optionally substituted pyrimidyl, optionally substituted tetrahydropyranyl, wherein the optional substituents are halogen, cyano, alkyl, nitro, amino, alkylamino, dialkylamino and —S(O)$_p$alkyl, where p is 0, 1, or 2.

In another embodiment, the present invention discloses compounds which are represented by structural formulae III or IV or a pharmaceutically acceptable salt, solvate or ester thereof, wherein the various moieties are as described above:

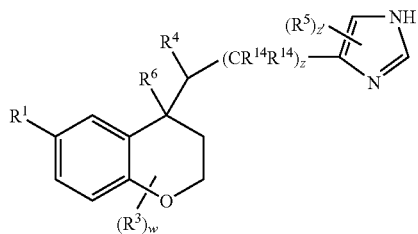

Formula III

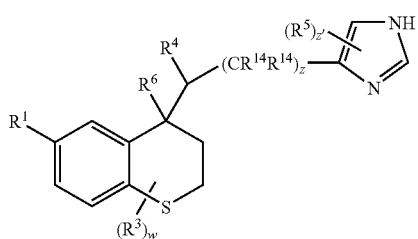

Formula IV wherein the individual variables are defined above and z' is 0, 1, 2 or 3.

Preferred compounds of formulae III and IV are those wherein:

$R^1$ is —(CH$_2$)$_q$YR$^{7'}$, —(CH$_2$)$_q$NR$^7$YR$^{7'}$ or —(CH$_2$)$_q$N(YR$^7$)(YR$^{7'}$);

Y is a —C(=O)NR$^7$—, —C(=O)O—, —S(O)$_p$—, and —SO$_2$NR$^7$—;

$R^7$ is H, optionally substituted alkyl (preferably $C_1$-$C_5$-alkyl), optionally substituted alkoxy (preferably methoxy or ethoxy), optionally substituted cycloalkyl (e.g., cyclopropyl), optionally substituted alkynyl, optionally substituted phenyl, optionally substituted benzyl, optionally substituted heteroaryl (e.g., optionally substituted pyridyl, thienyl, or pyrimidinyl) optionally substituted-$C_1$-$C_3$-alkyl (e.g., optionally substituted pyridylmethyl, optionally substituted pyridylethyl, optionally substituted thiazolylmethyl, optionally substituted thiazolylethyl, optionally substituted isothiazolylmethyl, or optionally substituted isothiazolylethyl), amino, alkylamino, dialkylamino, or optionally substituted heterocyclyl (e.g., optionally substituted morpholino, thiomorpholino, or piperidino), $R^{7'}$ is H or alkyl;

z is 0-5 q is 0-5, preferably 0 or 1; and z' is 0-3 and

Preferred optional substituents include alkyl, halo, —CN, —NO$_2$, alkoxy, amino, alkylamino, or dialkylamino.

An especially preferred group of compounds are those of formula II wherein Z is zero.

In another embodiment, the present invention discloses compounds which are represented by structural Formula V or a pharmaceutically acceptable salt, solvate or ester thereof

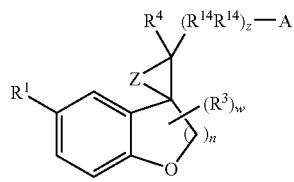

Formula V wherein the individual groups are the same as those listed for Formula I.

In another embodiment for Formula V, A is an optionally substituted imidazole, wherein the optional substitutents are those listed for $R^5$.

In another embodiment, A is imidazole, z is (CH$_2$)—, n is 2 and $R^1$ is —(CH$_2$)$_q$N(YR$^7$)(YR$^{7'}$), where Y is independently a bond, —C(=O)NR$^7$—, and —C(=O)O—, and $R^7$ and $R^{7'}$ are independently H, alkyl, cycloalkyl, optionally substituted phenyl, or optionally substituted phenylalkyl, wherein the optional substitutents are alkyl, halo, —CN, —NO$_2$, alkoxy, amino, alkylamino, or dialkylamino.

A group of compounds is shown below:

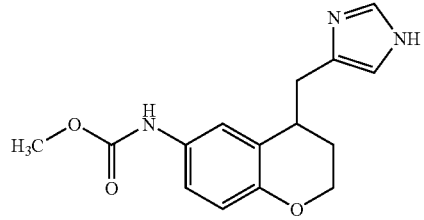

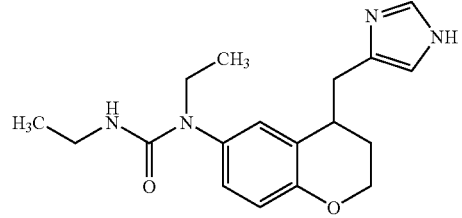

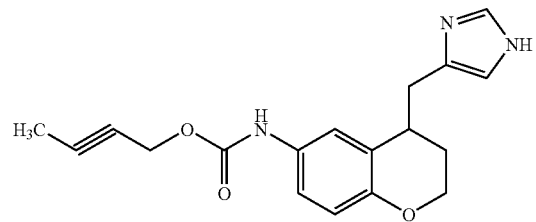

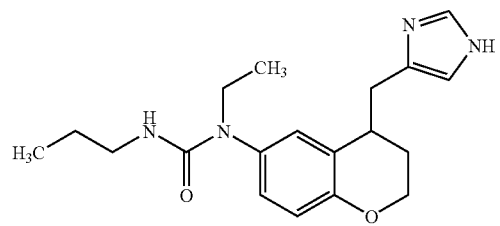
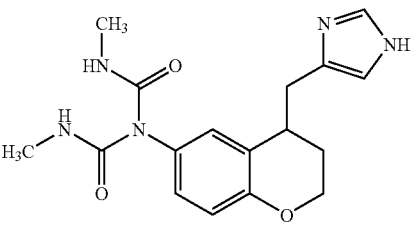
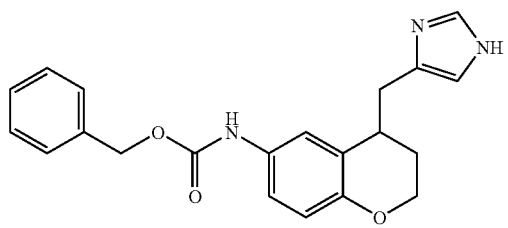
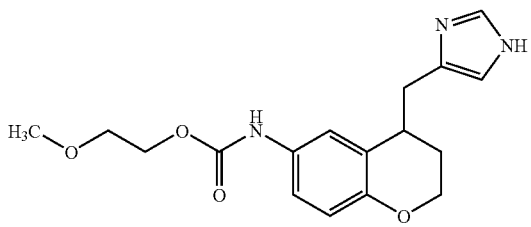
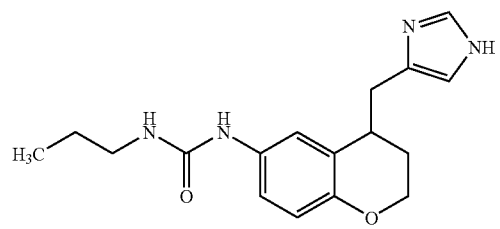
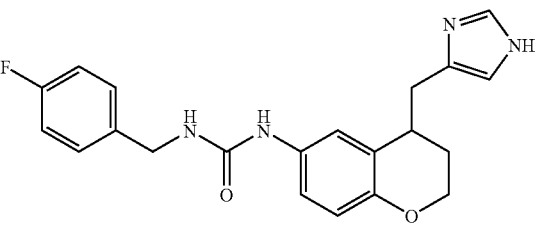
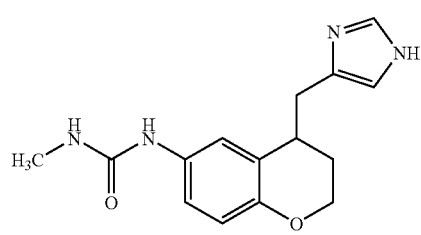
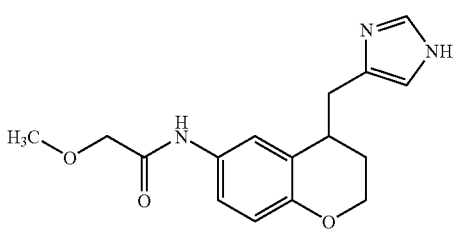
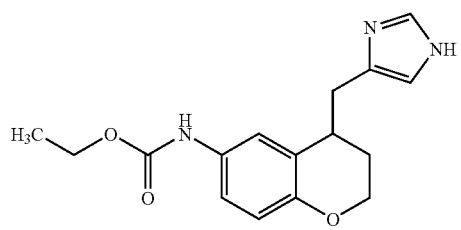
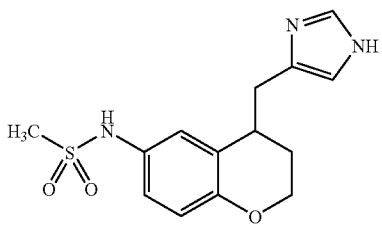
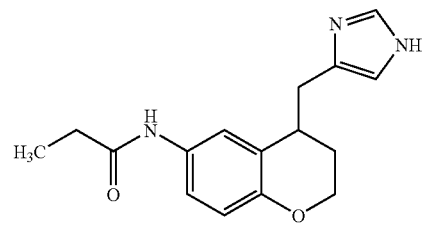
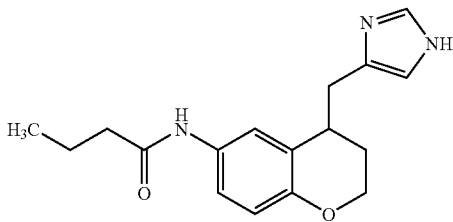
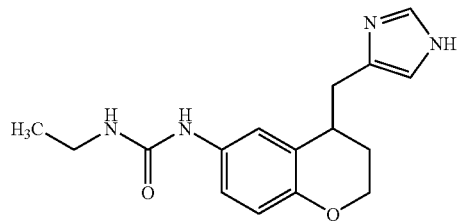
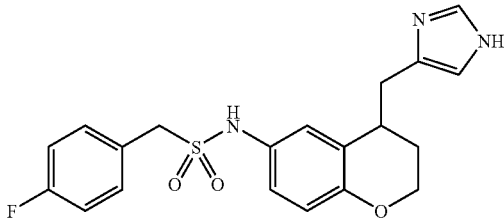

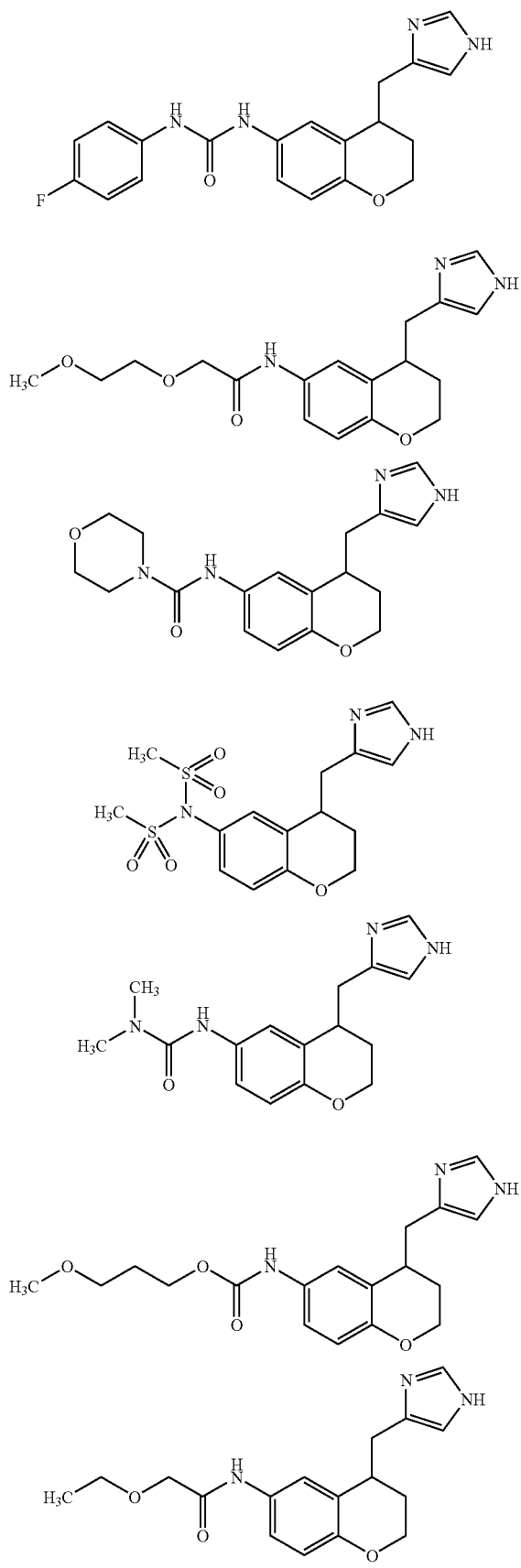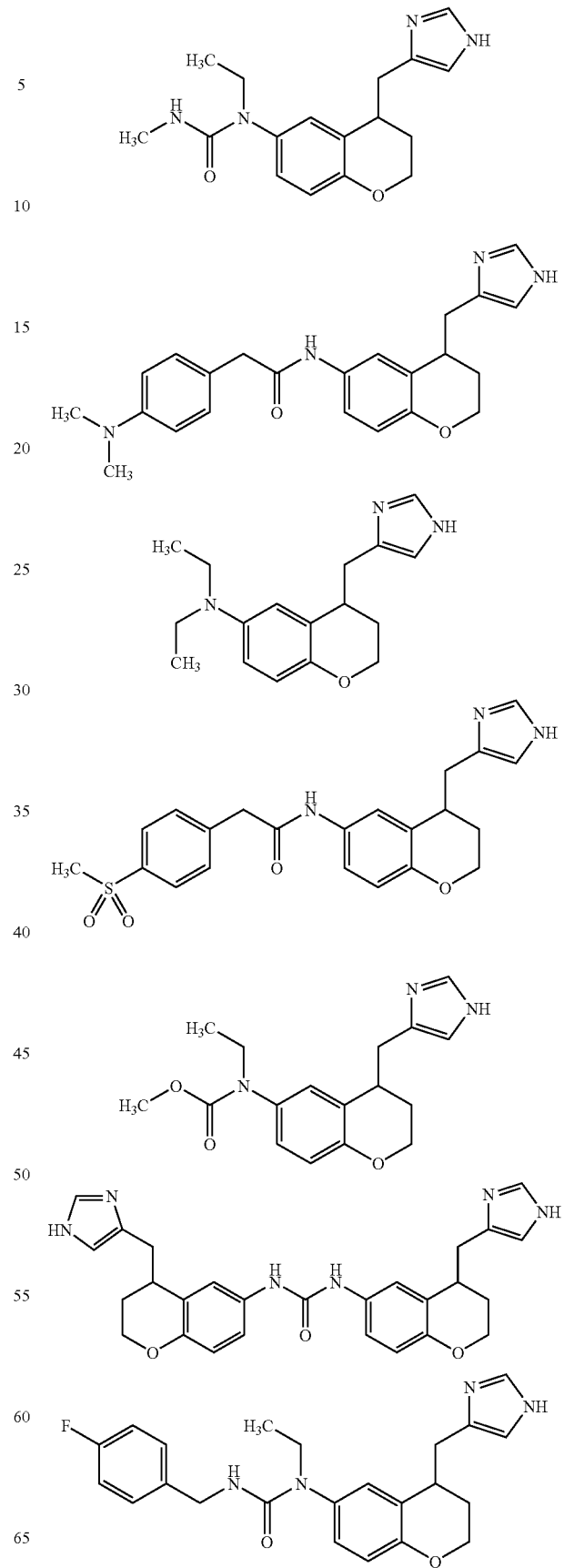

27
-continued
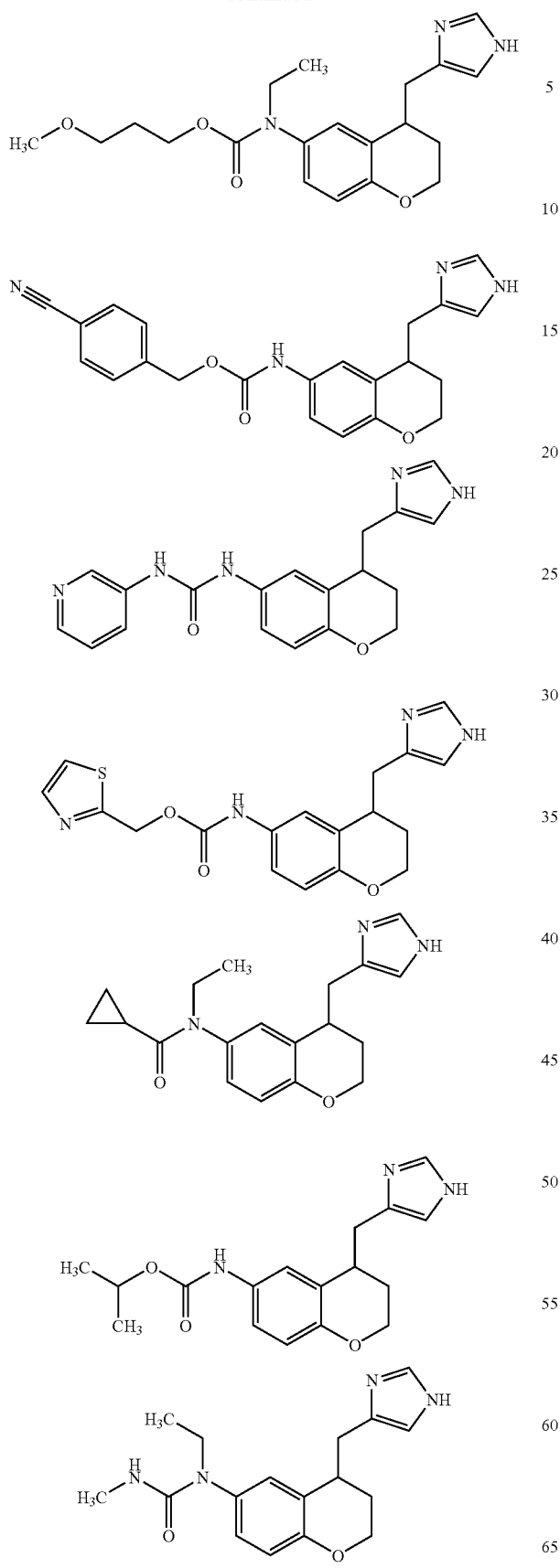
28
-continued
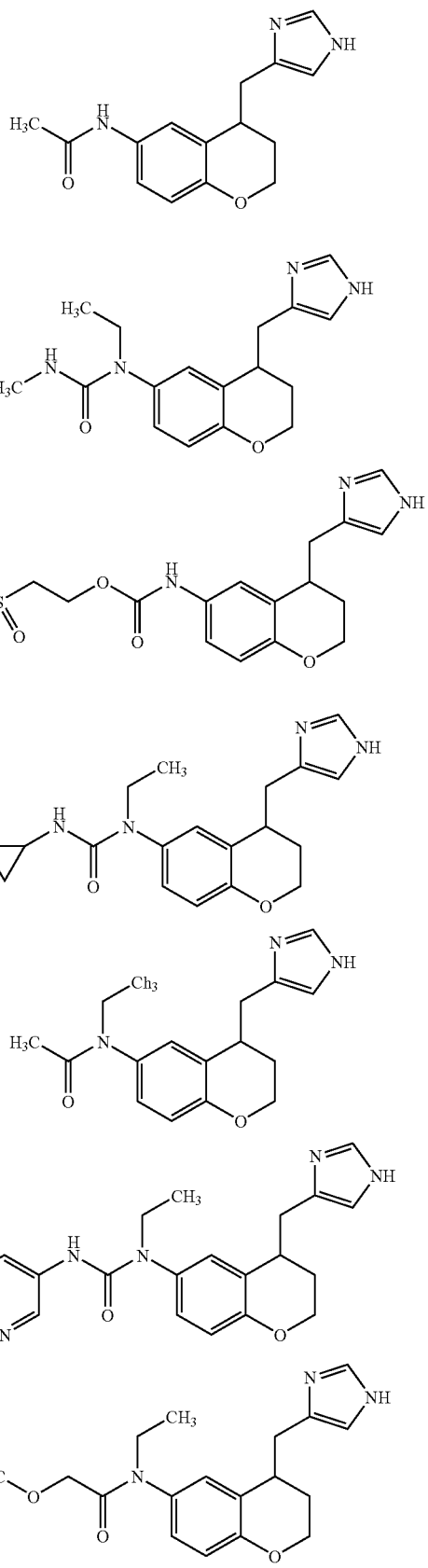

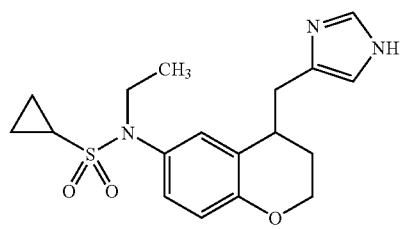
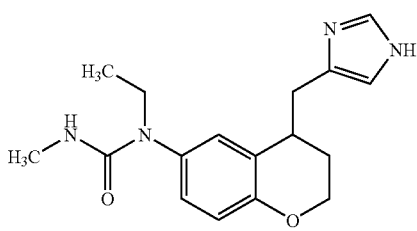
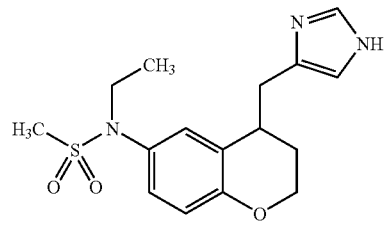
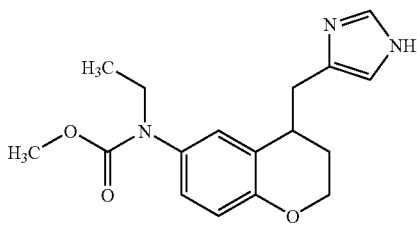
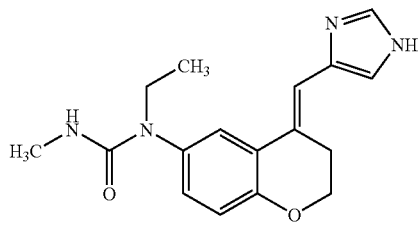
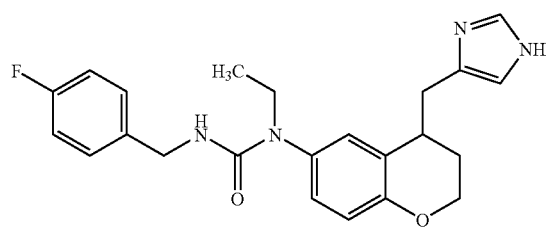
An especially preferred group of compounds of the invention is shown below:
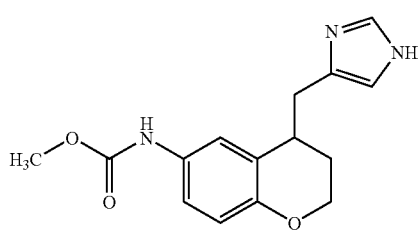
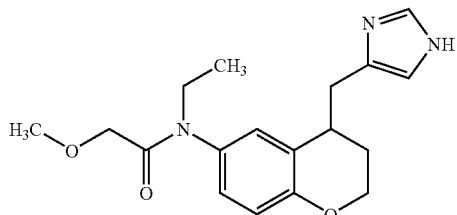
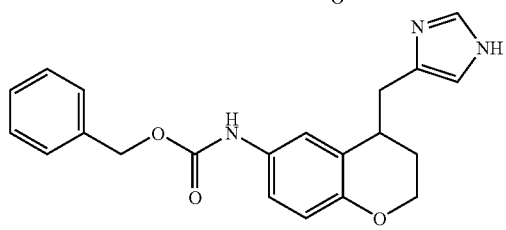
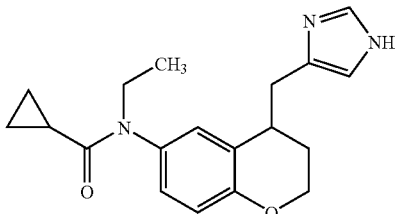
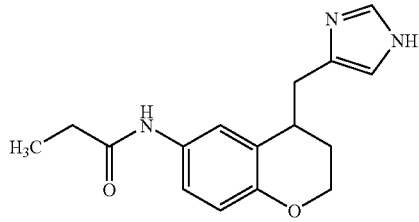
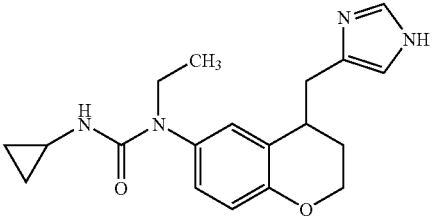
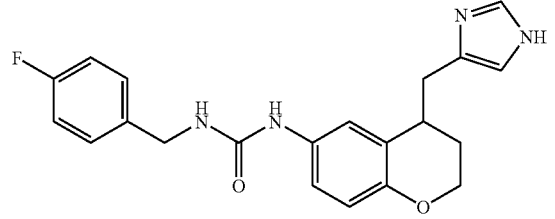
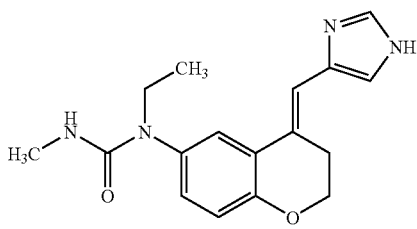

-continued
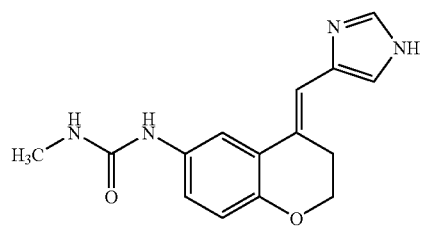
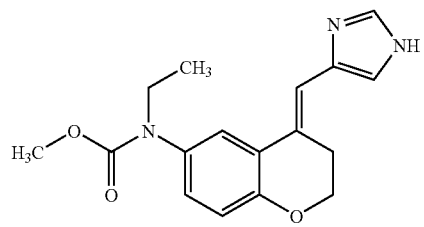
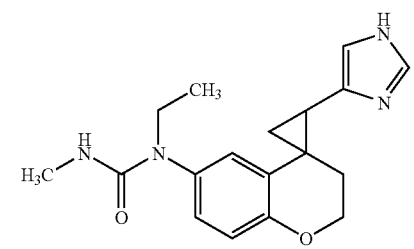
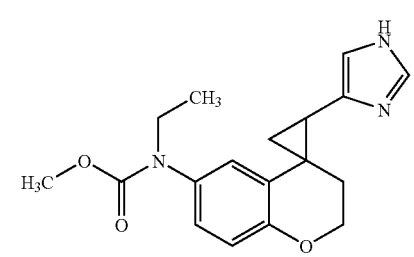
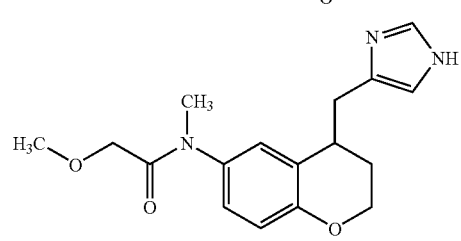
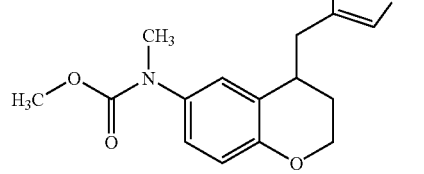
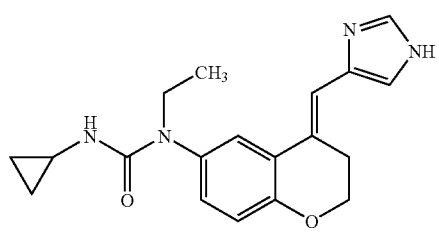
-continued
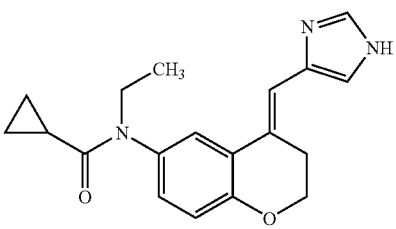
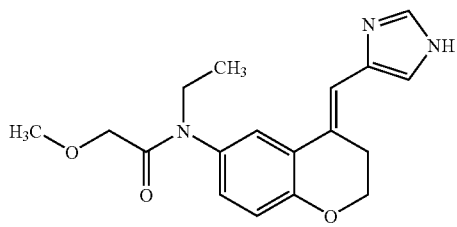
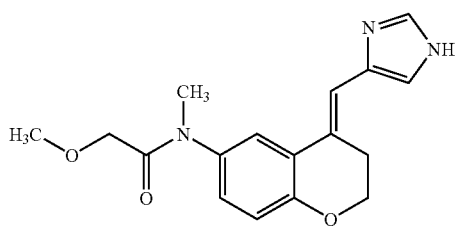
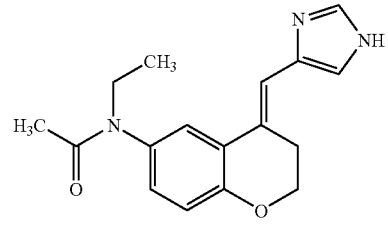
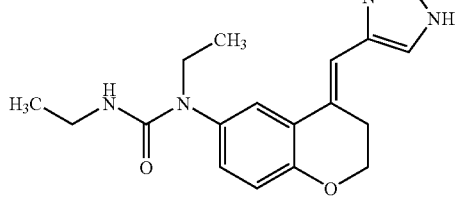
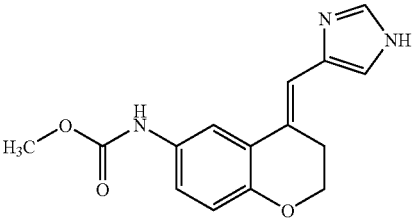
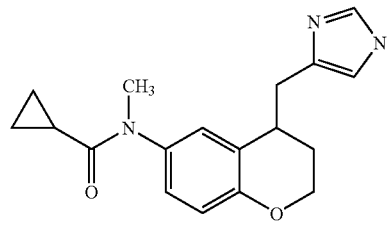

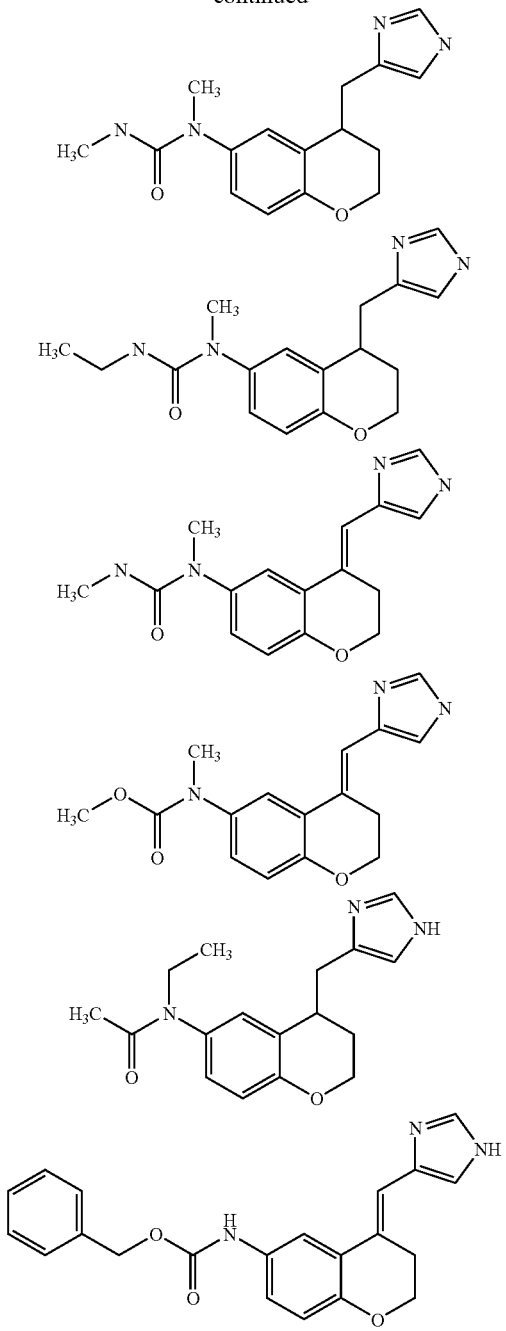

In another embodiment, the present invention discloses a pharmaceutical composition of the compounds of the present invention further comprising one or more additional therapeutic agents provided that the additional therapeutic agents do not include alpha-1 receptor antagonists.

In another embodiment, the additional therapeutic agents are selected from the group consisting of steroids, glucocorticosteroids, PDE-4 inhibitors, anti-muscarinic agents, muscle relaxant, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, sedatives, NMDA receptor antagonist, alpha-adrenergics, anticonvulsants, tachykinin (NK) antagonists such as NK-3, NK-2 and NK-1, COX-2 inhibitors, neuroleptics, vanilloid receptor agonist or antagonist, beta-adrenergics, local anaesthetic, corticosteroid, serotonin receptor agonist or antagonist, PDEV inhibitor, alpha-2-delta ligand, canabinoid and therapeutic agents suitable for treating heart conditions, psychotic disorders, glaucoma.

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

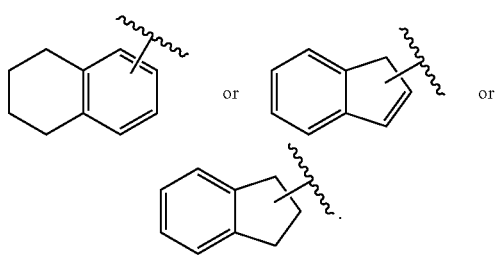

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of hetreroaryl multicyclic ring systems include:

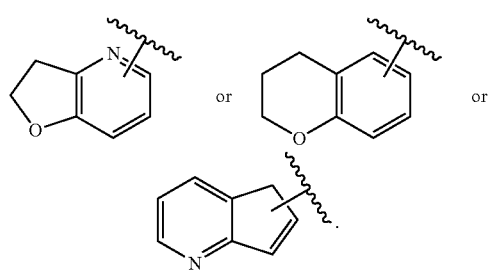

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, imidazolidinyl, pyrazolidinyl, piperazinyl, morpholinyl, thiomorpholinyl, thiazolidinyl, 1,4-dioxanyl, tetrahydrofuranyl, tetrahydrothiophenyl, and the like.

Compounds of Formula I and salts, esters, solvates and prodrugs thereof, may exist in their tautomeric form (for example, as an amide or imino ether). All such tautomeric forms are contemplated herein as part of the present invention. Non-limiting examples of tautomeric forms that are part of this invention are as follows:

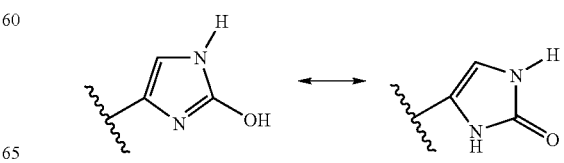

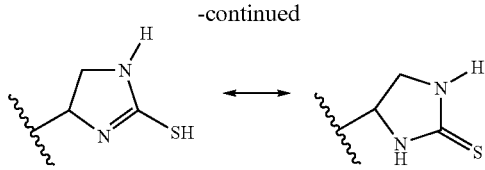

It should be noted that in saturated heterocyclyl containing systems of this invention, there are no hydroxyl, amino, or thiol groups on carbon atoms adjacent to a N, O or S atom. Thus, for example, in the ring:

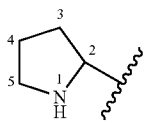

there is no —OH attached directly to carbons marked 2 and 5. It should also be noted that this definition does not preclude (═O), (═S), or (═N) substitutions, or their tautomeric forms, on C atoms adjacent to a N, O or S. Thus, for example, in the above ring, (═O) substitution on carbon 5, or its imino ether tautomer is allowed.

Non-limiting examples which illustrate the present invention are as follows:

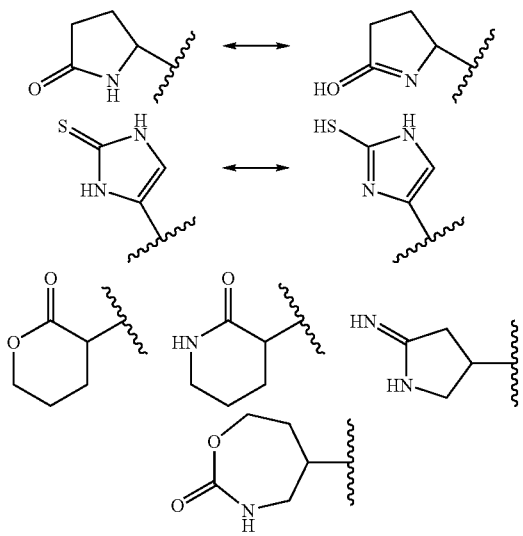

The following non-limiting examples serve to illustrate radicals not contemplated by the present invention:

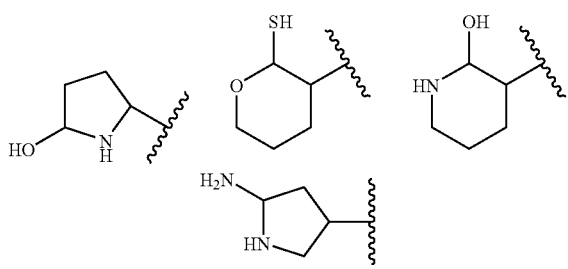

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclenylalkyl" means a heterocyclenyl-alkyl group in which the heterocyclenyl and the alkyl are as previously described.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O-group in which the heteroarylalkyl group is as previously described.

"Heterocyclylalkoxy" means a heterocyclylalkyl-O group in which the hetrocyclylalkyl group is as previously described.

"Heterocyclenylalkoxy" means a heterocyclenylalkyl-O group in which the heterocyclenylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

It is noted that carbons of Formula I can be replaced with 1-3 silicon atoms, provided all valency requirements are satisfied.

The term "optionally substituted" means optional substitution with the specified groups, radicals or moieties.

The term "continuous double bonds" means two adjacent double bonds; i.e., —C=C=C—.

The straight line ——— as a bond generally indicates a mixture of, or either of, the possible isomers, non-limiting example(s) include, containing (R)- and (S)-stereochemistry. For example,

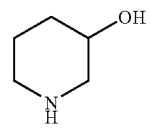

means containing both

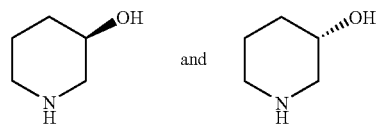 [SMILES: O[C@@H]1CCCNC1 ; O[C@H]1CCCNC1]

A dashed line (-----) represents an optional bond.
Lines drawn into the ring systems, such as, for example:

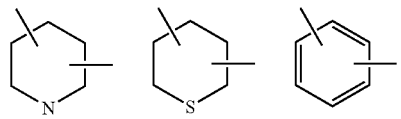

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

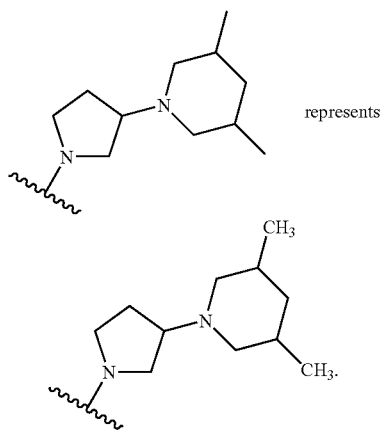

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or formula, its definition on each occurrence is independent of its definition at every other occurrence.

Unless defined otherwise, all definitions for the variables follow the convention that the group to the right forms the point of attachement to the molecule; i.e., if a definition is arylalkyl, this means that the alkyl portion of the definition is attached to the molecule.

Further, all divalent variable are attached from left to right. For example when $R^1$ is $-(CH_2)_qN(R^7)YR^{7'}$, and Y is $-C(=O)-[C(R^a)(R^b)]_n-O-C(=O)-$, then $R^1$ forms the group $-(CH_2)_qN(R^7)-C(=O)-[C(R^a)(R^b)]_n-O-C(=O)-R^{7'}$.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as ẞ-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $-P(O)(OH)_2$, $-P(O)(O(C_1-C_6)$alkyl$)_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, $-C(OH)C(O)OY^1$ wherein $Y^1$ is H, $(C_1-C_6)$alkyl or benzyl, $-C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, $-C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formula I are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula I or may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formulae Ia or Ib may be atropisomers (e.g., substituted biaryls) and are considered as part of this invention. Enantiomers can also be separated by use of chiral HPLC column.

Polymorphic forms of the compounds of Formula I, and of the salts, solvates and prodrugs of the compounds of Formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination with one or more additional therapeutic agents provided that the other therapeutic agents does not include alpha-1 receptor antagonists.

The compounds of this invention may be administered together or sequentially with one or more additional therapeutic agents such as, for example, steroids, glucocorticosteroids, PDE-4 (phosphodiesterase 4) inhibitors anti-muscarinic agents, muscle relaxants, cromolyn sodium, $H_1$ receptor antagonists, 5-$HT_1$ agonists, NSAIDs (non-steroidal anti-inflammatory drugs), angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, sedatives, NMDA (N-methyl-D-aspartic acid) receptor antagonists, alpha-adrenergics not including alpha-1 receptor antagonists, anticonvulsants, tachykinin (NK) antagonists such as NK-3, NK-2 and NK-1, COX-2 inhibitors, neuroleptics, vanilloid receptor agonists or antagonists, beta-adrenergics, local anaesthetic, corticosteroids, serotonin receptor agonists or antagonists, PDEV inhibitors, alpha-2-delta ligands, canabinoids.

Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, cortisone.

Suitable PDE-4 inhibitors include roflumilast, theophylline, rolipram, piclamilast, cilomilast and CDP-840.

Suitable antiimuscarinic agents include ipratropium bromide, tiatropium bromide, oxybutin, tolterodine, propiverine, tropsium chloride and darifenacin.

Suitable skeletal muscle relaxants include baclofen, carisoprodol, chlorzoxazone, cyclobenzprine, methocarbamol and orphenadine.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine, triprolidine and chlorcyclizine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, tolmetin, fenbufen, fenoprofen, flufenisal, phenylbutazone, and zomepirac.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, amitriptyline, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, percocet, morphine sulfate, dilaudid, stadol, stadol NS, acetaminophen with codeine, acetaminophen with codeine #4, Lidoderm® patches, ziconotide, duloxetine, roboxetine, gabapentin, pregabalin and opioid analgesic such as morphine, heroin, hydromorphone, oxymorphone, levorphanol, levallorphan, methadone, meperidine, fentanyl, cocaine, codeine, dihydrocodeine, oxycodone, hydrocodone, propolyphene, nalmefene, nalorphine, naloxone, naltrexone, buprenorphine, butorphanol, nalbuphine, coal tar such as paracetamol, cholinergic (nicotinic) analgesic and pentazocine.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, trimipramine maleate and imipramine.

Suitable barbiturate sedatives include amobarbital, aprobarbital, butabarbital, butabital, mephobarbital, metharbital, methohexital, pentobarbital, phenobartital, secobarbital, talbutal, theamylal and thiopental.

Suitable benzodiazepines with sedative action include chlordiazepoxide, clorazepate, diazepam, flurazepam, lorazepam, oxazepam, temazepam and triazolam.

Suitable NMDA receptor antagonists includedextromethorphan ((+)-3-hydroxy-N-methylmorphinan) or its metabolite dextrorphan ((+)-3-hydroxy-N-methylmorphinan), ketamine, memantine, pyrroloquinoline quinone and cis-4-(phosphonomethyl)-2-piperidinecarboxylic acid.

Suitable alpha-adrenergics include doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline and does not include alpha-1 receptor antagonists.

Suitable anticonvulsants include carbamazepine and vaiproate.

Suitable tachykinin (NK) antagonists such as NK-3, NK-2 and NK-1 include (aR,9R)-7-[3,4-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-627), 5-[[(2R,3S)-2-[(1R)-1-[3,5-bis(trifluoromethyl)phenyl]ethoxy-3-(4-fluorophenyl)-4-mmorpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S).

Suitable COX-2 inhibitors include celecoxib, rofecoxib and valdecoxib.

Suitable non-selective COX inhibitors, preferably with G1 protection, include nitroflurbiprofen (HCT-1026).

Suitable neuroleptics include droperidol.

Suitable vanilloid receptor agonists include resinferatoxin or antagonist include capsazepine.

Suitable beta-adrenergics include propranolol.

Suitable local anaestheics include mexiletine.

Suitable corticosteroids include dexamethasone.

Suitable PDEV inhibitors include sildenafil, vardenafil, and taladafil.

Suitable alpha-2-delta ligands include gabapentin and pregabalin.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be anyalyzed for their composition and purity as well as characterized by standard analytical techniques such as, for example, elemental anyalysis, NMR, mass spectroscopy and IR spectra.

One skilled in the art will recognize that reagents and solvents actually uised may be selected from several reagents and solvents well known in the art to be effective equivalents. Hence, when a specific solvent or reagent is mentioned, it is meant to be an illustrative example of the conditions deserible for that particular reactionscheme and in the proparations and examples described below.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; Ph=phenyl, and Ac=acetyl
μl=microliters
AcOEt or EtOAc=ethyl acetate
AcOH or HOAc=acetic acid
ACN=acetonitrile
atm=atmosphere
Boc or BOC=tert-butoxycarbonyl
DCM or $CH_2Cl_2$: dichloromethane:
DIPEA=diisopropylethylamine
DMAP=4-dimethylaminopyridine
DMF=dimethylformamide
DMS=dimethylsulfide
DMSO=dimethyl sulfoxide
EDCI=1-(3-dimethylaminopropyl)-3-ethylcarbodiimide
Fmoc=9-fluorenylmethoxycarbonyl
g=grams
h=hour
HATU=O-(7-azabenzotriazol-1-yl)-N,N,N',N'-tetramethyluronium hexafluorophosphate
HOBt=1-hydroxybenzotriazole
LAH=lithium aluminum hydride
LCMS=liquid chromatography mass spectrometry
min=minute
mg=milligrams
mL=milliliters
mmol=millimoles
MCPBA=3-chloroperoxybenzoic acid
MeOH: methanol
MS=mass spectrometry
NMR=nuclear magnetic resonance spectroscopy
RT or rt=room temperature (ambient, about 25° C.).
TEA or $Et_3N$=triethylamine
TFA=trifluoroacetic acid
THF=tetrahydrofuran
TLC=thin layer chromatography
TMS=trimethylsilyl
Tos or tosyl=p-toluenesulfonyl
Tr=triphenylmethyl

EXAMPLES

The compounds of this invention can be prepared through the general approach outlined in the schemes provided below. These schemes are being provided illustrate the present invention. While group A is exemplified as an imidazole, other optionally substituted heteroaryl, heterocyclyl and heterocyclenyl rings containing one to three heteroatoms may be used in place of imidazole.

In Scheme 1, 6-nitrochroman-4-one S1 can be homologated to aldehyde S2 via one of numerous methodologies known to those skilled in the art, including a Wittig-hydrolysis sequence. Compound S3, protected with BOC, trityl, Bn, —SO$_2$NMe$_2$ or other appropriate group, may be activated via Grignard or other metal-faciliated process, and reacted with S2. This step is followed by an elimination to provide alkene S4, which may be further reduced to aniline S5 by hydrogenation or other appropriate method. Upon treatment with a variety of acid chlorides, chloroformates, sulfonyl chlorides or isocyanates, S5 can be converted to target compounds S6. Alternatively, S4 is mono-alkylated under various conditions including alkylation, an acylation-reduction sequence or hydrogenation in the presence of various nitriles. The resulting compound S7 can react with a variety of acid chlorides, chloroformates, sulfonyl chlorides or isocyanates to give target compounds S8.

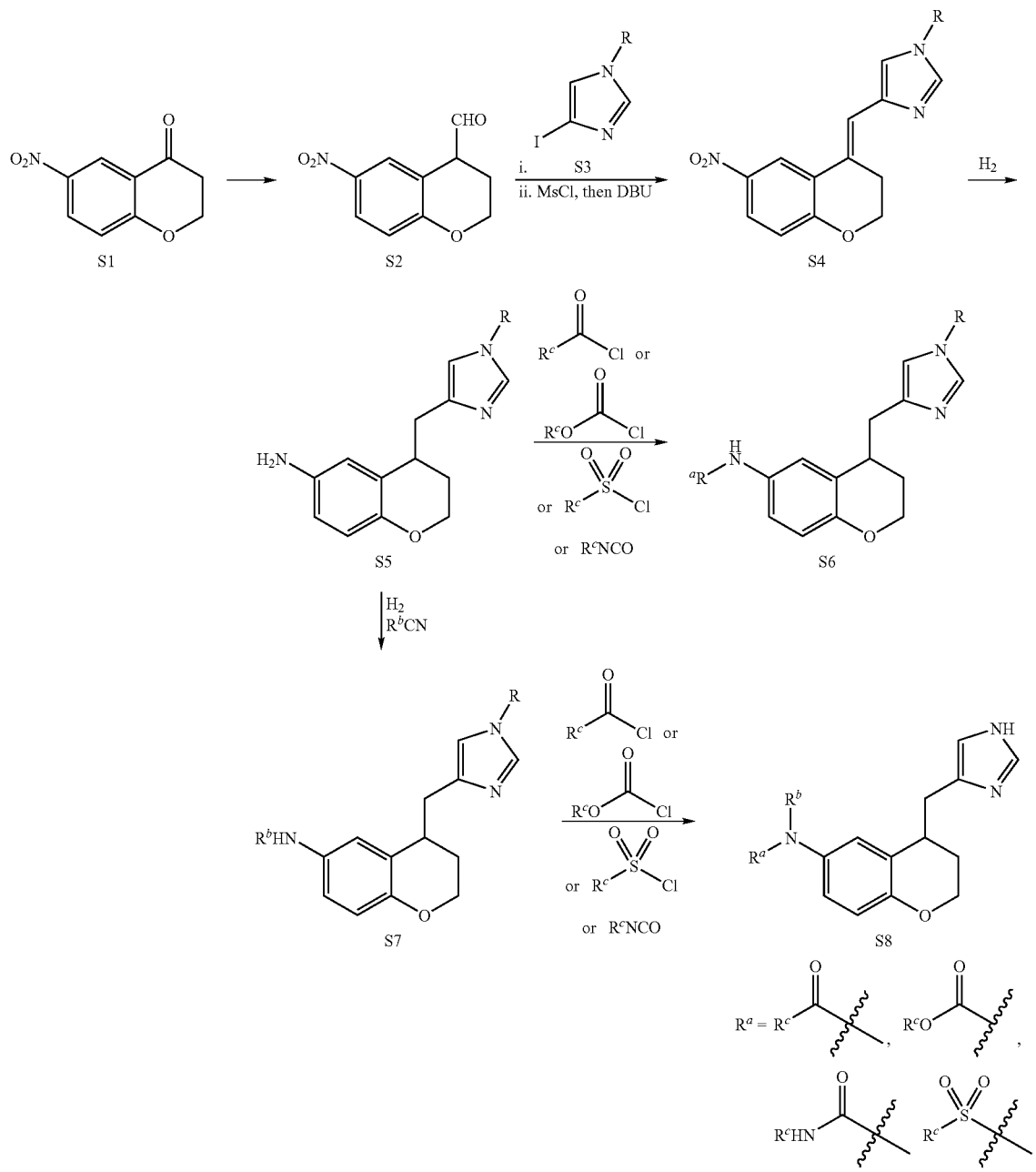

SCHEME 1

According to another embodiment, compound S4 may be selectively reduced by numerous methods including Cu(OAc)-2-NaBH$_2$ to provide S9 (Scheme 2). Subsequent alkyation, acylation, or sulfonylation, as described above, followed by deprotection affords S10.

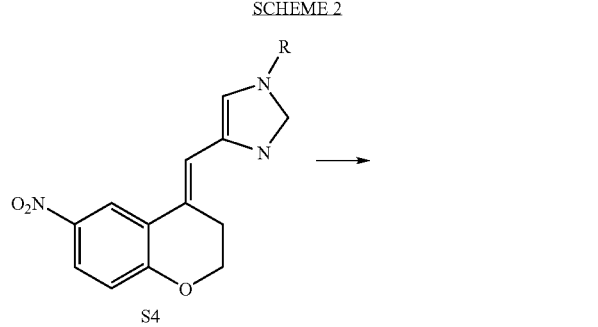

According to another embodiment (Scheme 3), benzofuran or benzothiophene S11 (X=O or S, respectively) may be alkylated with S12, wherein Y is an appropriate leaving group (such as Cl, Br, I, or OH) under Lewis acid conditions, such as ZnCl$_2$ or SnCl$_4$. The resulting compound S13 (Scheme 3) may be derived via methods described above.

According to another embodiment, 3,4-dihydro-7-nitrobenzoxepin-5-one (S15, PCT application WO 89/11477) may be converted to S16 or S17 (Scheme 4) via methods described in Scheme 1 or 2.

According to another embodiment (Scheme 5), 4-nitrothiophenol (S18) is reacted with S19, wherein Y is an appropriate leaving group (such as Cl, Br, I, or activated alcohol). The resulting compound S20, is cyclized to S21, under various conditions including acidic or Lewis acidid, and then further substituted to S22 as described in Scheme 1 or 2.

SCHEME 5

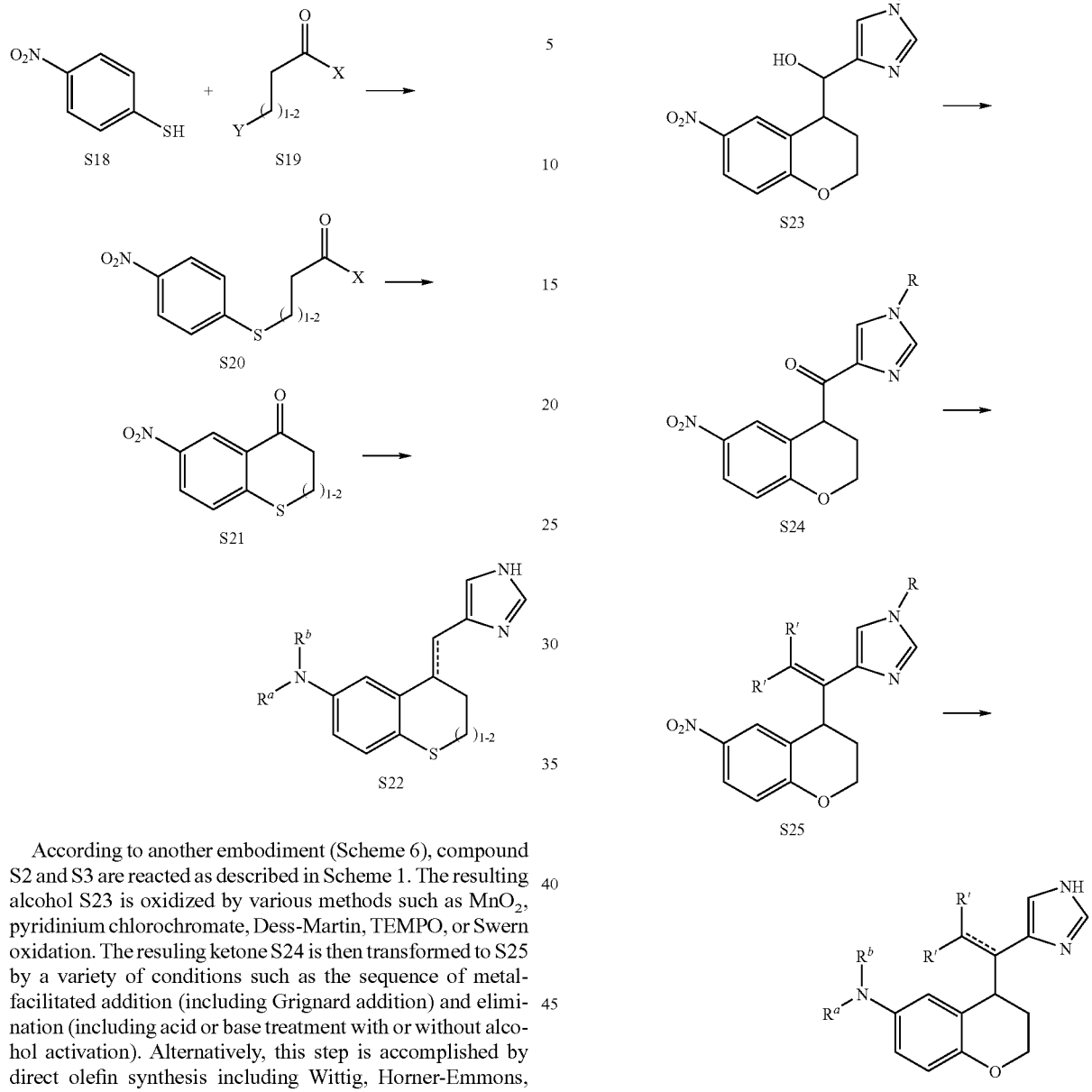

According to another embodiment (Scheme 6), compound S2 and S3 are reacted as described in Scheme 1. The resulting alcohol S23 is oxidized by various methods such as MnO$_2$, pyridinium chlorochromate, Dess-Martin, TEMPO, or Swern oxidation. The resuling ketone S24 is then transformed to S25 by a variety of conditions such as the sequence of metal-facilitated addition (including Grignard addition) and elimination (including acid or base treatment with or without alcohol activation). Alternatively, this step is accomplished by direct olefin synthesis including Wittig, Horner-Emmons, Peterson, or other reatled methods. Compound S25 is converted to S26, as detailed previously, wherein the benzylic double bond may or may not be reduced by methods such as catalytic hydrogenation.

SCHEME 6

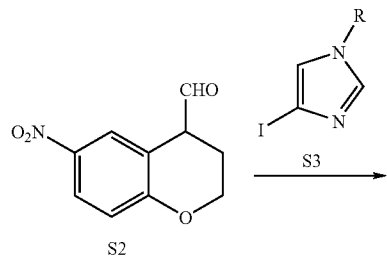

According to another embodiment (Scheme 7), compound S27 (in which X=O or S and Y=H, I, Br, or Cl) and S28 (in which Z is an appropriate leaving group such as I, Br, Cl or activated alcohol) are condensed under basic conditions to afford S29. Subsequent ring cyclization is conducted under a variety of conditions including, for example, radical (i.e. Bu$_3$SnH), metal-facilitated, or metal-catalyzed. The resulting dihydrobenzofuran or dihydrobenzothiophene S30 may be converted to aldehyde S31 by direct reduction or by a reduction-oxidation sequence. Compound S31 is treated with TosMIC/NaCN followed by NH$_3$ to afford imidazole S32, which may be furthered functionalized to S33, as detailed previously.

SCHEME 7

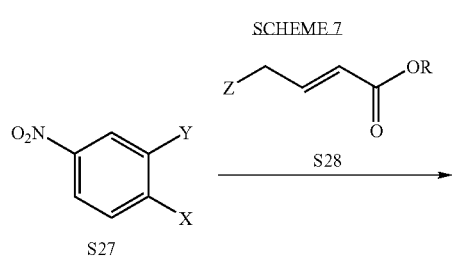

starting materials known in the art. These examples are being provided to further illustrate the present invention. They are for illustrative purposes only; the scope of the invention is not to be considered limited in any way thereby.

Preparative Example 1

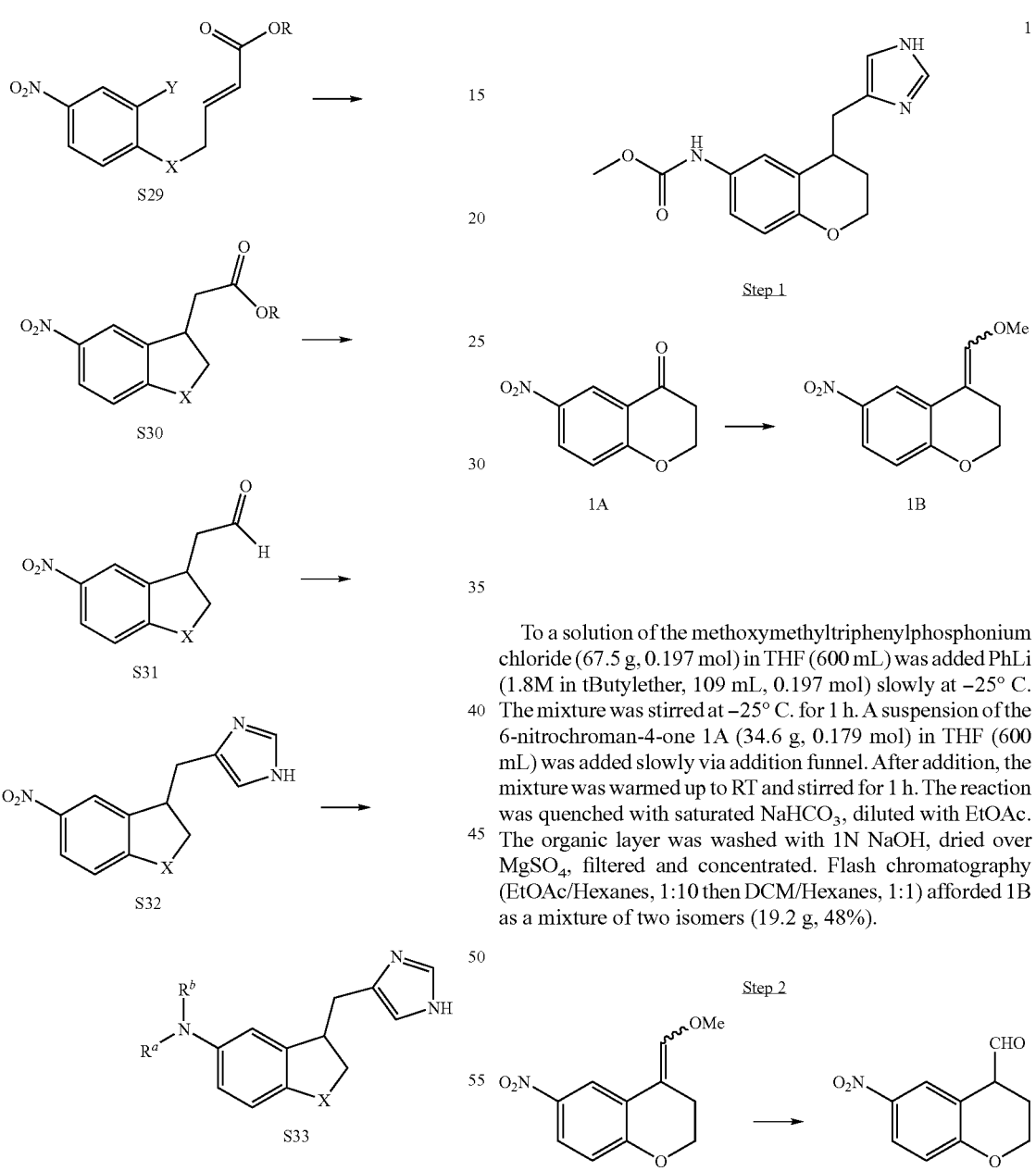

To a solution of the methoxymethyltriphenylphosphonium chloride (67.5 g, 0.197 mol) in THF (600 mL) was added PhLi (1.8M in tButylether, 109 mL, 0.197 mol) slowly at −25° C. The mixture was stirred at −25° C. for 1 h. A suspension of the 6-nitrochroman-4-one 1A (34.6 g, 0.179 mol) in THF (600 mL) was added slowly via addition funnel. After addition, the mixture was warmed up to RT and stirred for 1 h. The reaction was quenched with saturated NaHCO$_3$, diluted with EtOAc. The organic layer was washed with 1N NaOH, dried over MgSO$_4$, filtered and concentrated. Flash chromatography (EtOAc/Hexanes, 1:10 then DCM/Hexanes, 1:1) afforded 1B as a mixture of two isomers (19.2 g, 48%).

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formulae S6 and S8 can be prepared by the general methods outlined above. Exemplary compounds were prepared as described in the examples below or from 1B (23.5 g, 0.114 mol) was stirred in HCOOH (88%, 300 mL) at 90° C. for 2 h. The mixture was cooled down to RT, diluted with DCM and H$_2$O. The DCM layer was separated, washed with saturated NaHCO$_3$ 2X, brine, dried and concentrated to give 1C (20.5 g, 87%).

Step 3

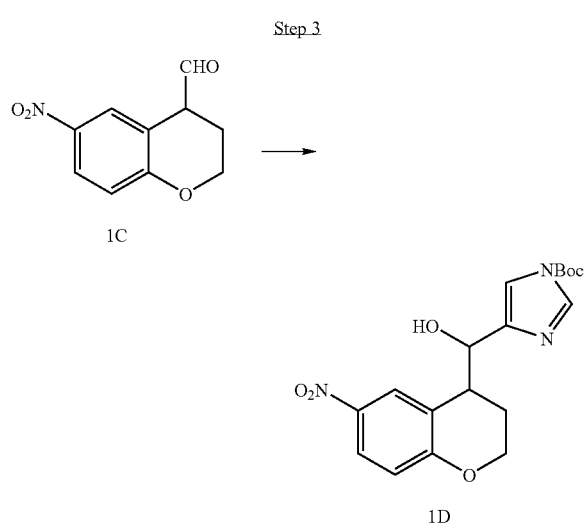

To a solution of 4-iodo-Boc-imidazole (12.95 g, 0.044 mol) in DCM (450 mL) was added EtMgBr (3.0M in Et₂O, 14.1 mL, 0.0423 mol) slowly at −20° C. The mixture was stirred at −20° C. for 1 h. A solution of 1C (6.8 g, 0.035 mol) in DCM (150 mL) was added dropwise. The mixture was stirred at RT for 30 min, quenched with saturated NaHCO₃, diluted with DCM. The DCM layer was washed with brine, dried and concentrated. Flash chromatography (EtOAc/Hexanes, 4:1) afforded 1D (9.1 g, 69%).

Step 4

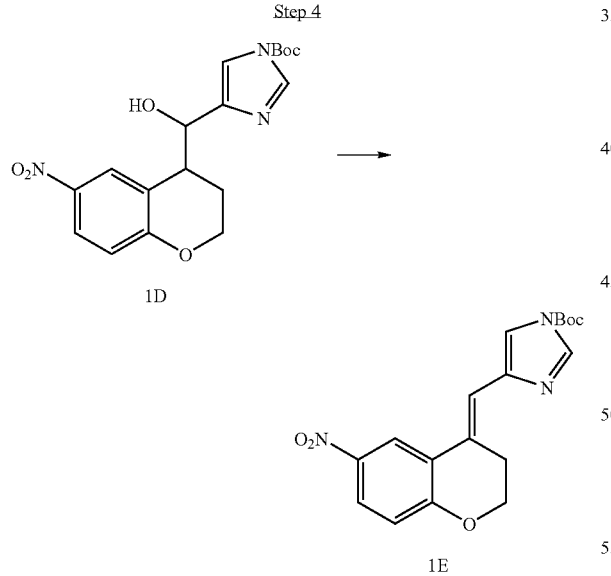

To a solution of 1D (7.83 g, 0.021 mol) in DCM (250 mL) was added DIPEA (4.04 g, 0.031 mol), followed by dropwise addition of MsCl (2.76 g, 1.87 mL, 0.024 mol) at 0° C. The mixture was stirred at RT for 1 h. DBU (15.9 g, 0.105 mol) was added in one portion. The mixture was stirred in a pressure flask at 65° C. for 1.5 h. The mixture was cooled down to RT, diluted with DCM, washed with saturated NaHCO₃, brine, dried and concentrated. Flash chromatography (EtOAc/Hexanes, 1:4) afforded 1E (5.5 g, 73%)

Step 5

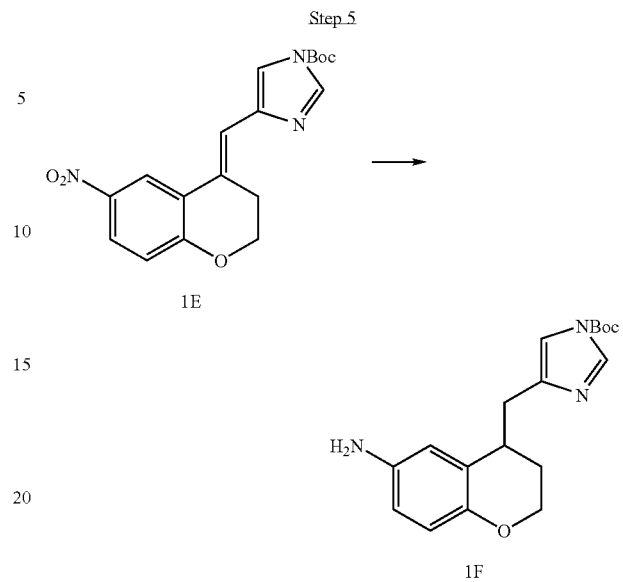

A mixture of 1E (5.5 g, 0.015 mol), Pd(OH)₂/C (10%, 500 mg) in MeOH (150 mL) was hydrogenated in the par system at 40 psi for 12 h. The mixture was degassed, filtered and concentrated. Flash chromatography (EtOAc/Hexanes, 4:1) afforded 1F (4.7 g, 92%)

Step 6

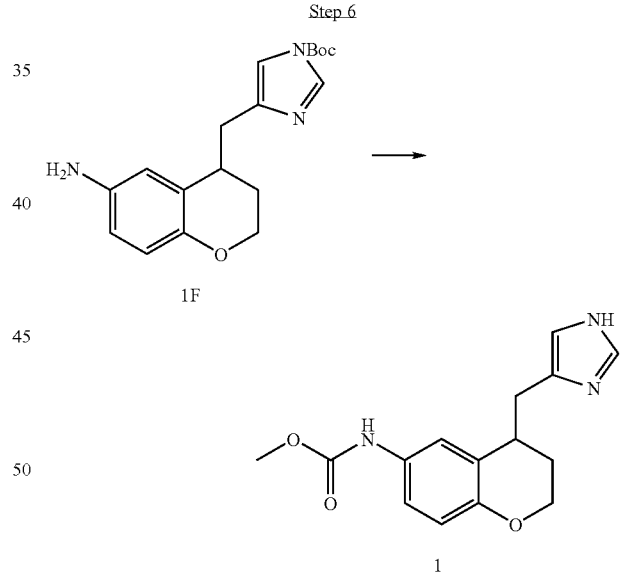

To a solution of 1F (400 mg, 1.216 mmol) in DCM (10 mL) was added DIPEA (314 mg, 2.432 mmol), followed by dropwise addition of a solution of methylchloroformate (127 mg, 1.338 mmol) in DCM (1 mL). The reaction mixture was allowed to stir at RT for 30 min, diluted with DCM, washed with 1N NaOH, brine, dried and concentrated. Flash chromatography (EtOAc/Hexanes, 4:1) afforded the carbamate. The residue was stirred in DCM (3 mL) and TFA (3 mL) at RT for 1.5 h. The TFA and DCM was removed in vacuo. Preparative TLC [MeOH(7N NH3)/DCM, 1:10] afforded 1 (202 mg, 58%). MS m/z 288 (MH⁺).

Examples 2-22

Examples 2-22 were prepared from 1F following the procedure set forth in preparative example 1, step 6, except that the reagent(s) listed in Table 1 below were used.

TABLE 1

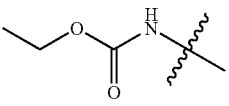 [SMILES: *NC(=O)OCC]

| Example No. | Reagents | R | MH+ |
|---|---|---|---|
| 2 | Ethylchloroformate<br>Et₃N | 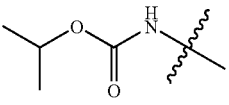 [SMILES: *NC(=O)OC(C)C] | 302 |
| 3 | Isopropylchloroformate<br>Et₃N | 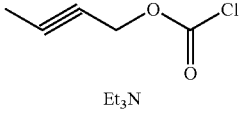 | 316 |
| 4 | 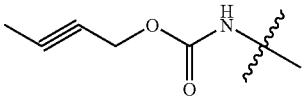 [SMILES: *NC(=O)OCC#CC]<br>Et₃N | 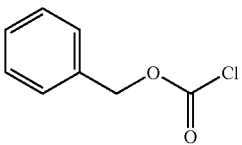 | 326 |
| 5 | 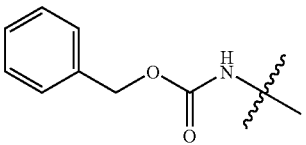 [SMILES: *NC(=O)OCc1ccccc1]<br>Et₃N | 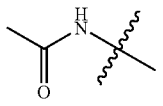 [SMILES: *NC(C)=O] | 364 |
| 6 | Acetyl chloride<br>Et₃N | 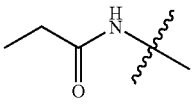 [SMILES: *NC(=O)CC] | 272 |
| 7 | Propionyl chloride<br>Et₃N | 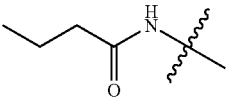 [SMILES: *NC(=O)CCC] | 286 |
| 8 | Butyryl chloride<br>Et₃N | 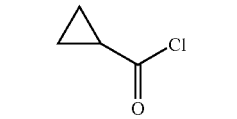 | 300 |
| 9 | 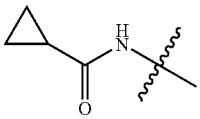 [SMILES: *NC(=O)C1CC1]<br>Et₃N | 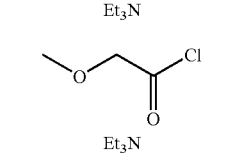 | 298 |
| 10 | 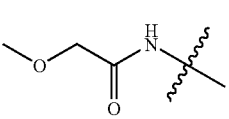 [SMILES: *NC(=O)COC]<br>Et₃N | | 302 |

TABLE 1-continued
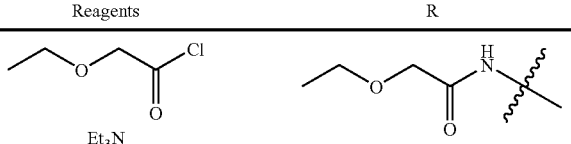
| Example No. | Reagents | R | MH+ |
|---|---|---|---|
| 11 | 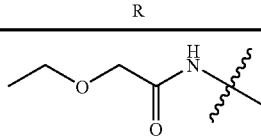 Et₃N | 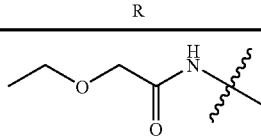 | 316 |
| 12 | 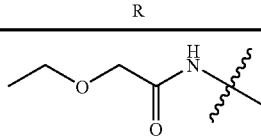 Et₃N | 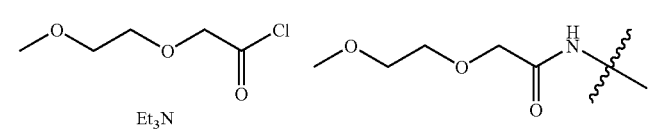 | 346 |
| 13 | MeNCO | 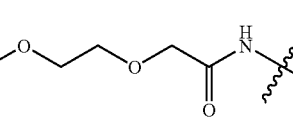 | 287 |
| 14 | EtNCO | 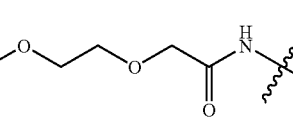 | 301 |
| 15 | PrNCO | 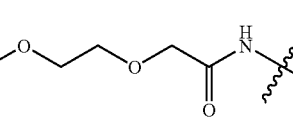 | 315 |
| 16 | 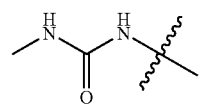 [SMILES: *NC(=O)NC] | 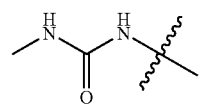 [SMILES: *NC(=O)NC] | 381 |
| 17 | 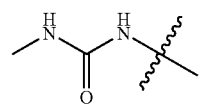 [SMILES: *NC(=O)NC] | 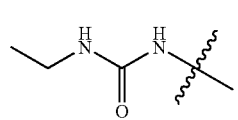 [SMILES: *NC(=O)NCC] | 367 |
| 18 | 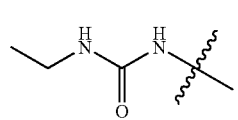 [SMILES: *NC(=O)NCC] | 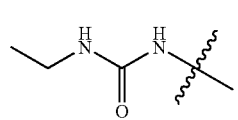 [SMILES: *NC(=O)NCC] | 350 |

TABLE 1-continued

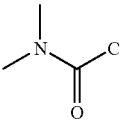

| Example No. | Reagents | R | MH+ |
|---|---|---|---|
| 19 | 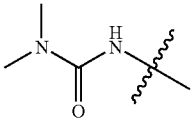 Et₃N | 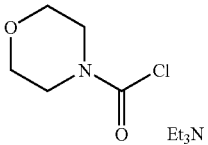 | 301 |
| 20 | 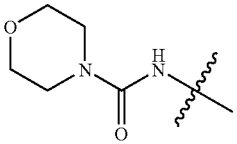 [SMILES: *NC(=O)N1CCOCC1] Et₃N | 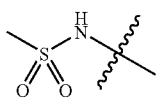 [SMILES: *NS(C)(=O)=O] | 343 |
| 21 | Methanesulfonyl chloride Et₃N | 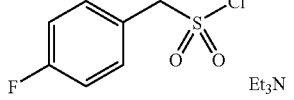 | 308 |
| 22 | 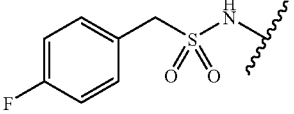 Et₃N | 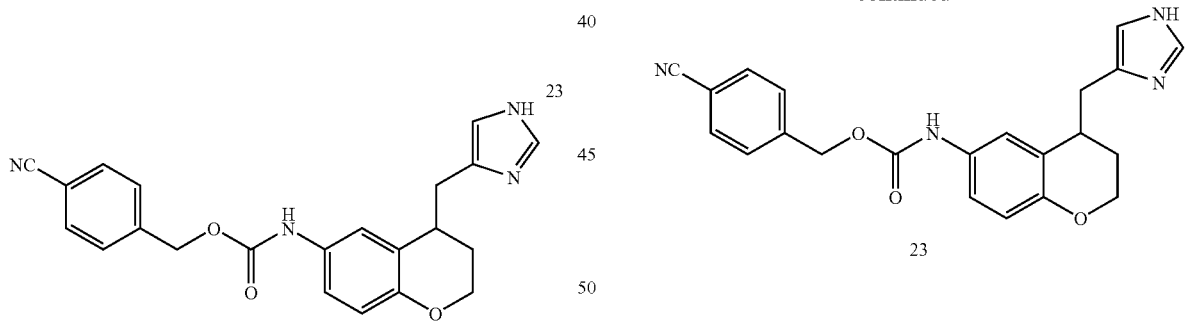 | 402 |

Preparative Example 23

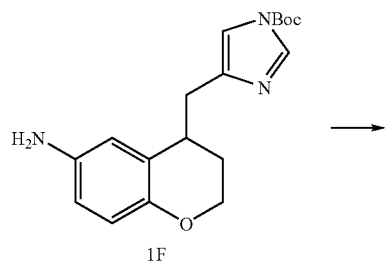

Step 1

23

-continued

23

To a stirred solution of 1F (200 mg, 0.608 mmol) in DCM (2 mL) and saturated NaHCO₃ (3 mL) at RT was added a solution of triphosgene (72 mg, 0.243 mmol) in DCM (1 mL) in one portion. The mixture was stirred for 30 min, diluted with DCM, washed with saturated NaHCO₃, brine, dried and concentrated to give the crude isocyanate. The residue was dissolved in dry toluene (4 mL). 4-cyanobenzyl alcohol (323 mg, 2.432 mmol) was added. The mixture was stirred at 80° C. for 30 min, cooled to RT, concentrated in vacuo. Preparative TLC (EtOAc/Hexanes, 8:1) afforded the carbamate. The residue was stirred in DCM (2 mL) and TFA (2 mL) at RT for 1.5 h. The TFA and DCM were removed in vacuo. Preparative TLC (MeOH(7N NH3)/DCM, 1:15) afforded 23 (81 mg, 34%). MS m/z 389 (MH+).

Examples 24-26

Examples 24-26 were prepared from 1F following the procedure set forth in preparative example 23, except that the reagent(s) listed in Table 2 below were used.

TABLE 2

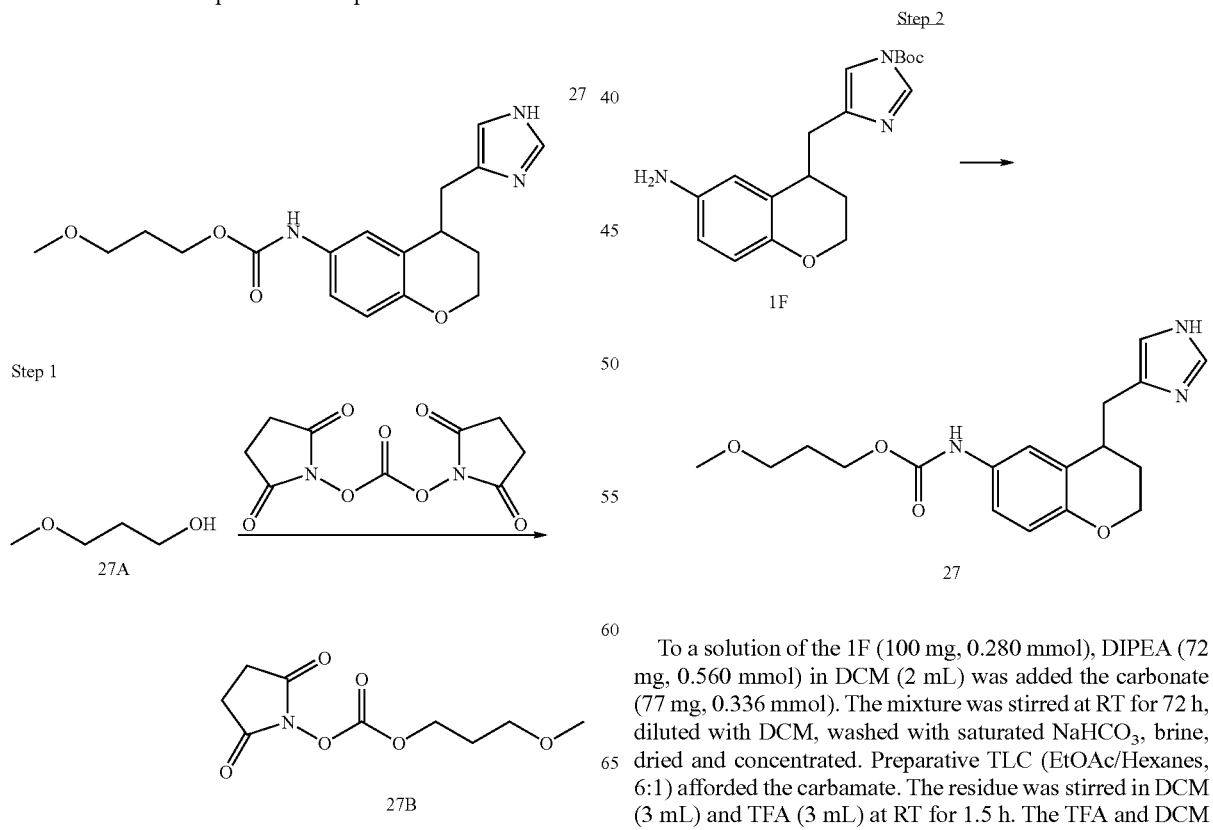

Preparative Example 27

To a solution of 27A (235 mg, 2.61 mmol), disuccinmidyl carbonate (1.0 g, 3.90 mmol) in CH₃CN (10 mL) was added Et₃N (527 mg, 5.22 mmol). The mixture was stirred at RT for 30 min, concentrated in vacuo. Flash chromatography (EtOAc/Hexanes, 1:9) afforded 27B (400 mg).

To a solution of the 1F (100 mg, 0.280 mmol), DIPEA (72 mg, 0.560 mmol) in DCM (2 mL) was added the carbonate (77 mg, 0.336 mmol). The mixture was stirred at RT for 72 h, diluted with DCM, washed with saturated NaHCO₃, brine, dried and concentrated. Preparative TLC (EtOAc/Hexanes, 6:1) afforded the carbamate. The residue was stirred in DCM (3 mL) and TFA (3 mL) at RT for 1.5 h. The TFA and DCM were removed in vacuo. Preparative TLC [MeOH(7N NH3)/DCM, 1:10] afforded 27 (52 mg, 54%). MS m/z 346 (MH+).

Preparative Example 28

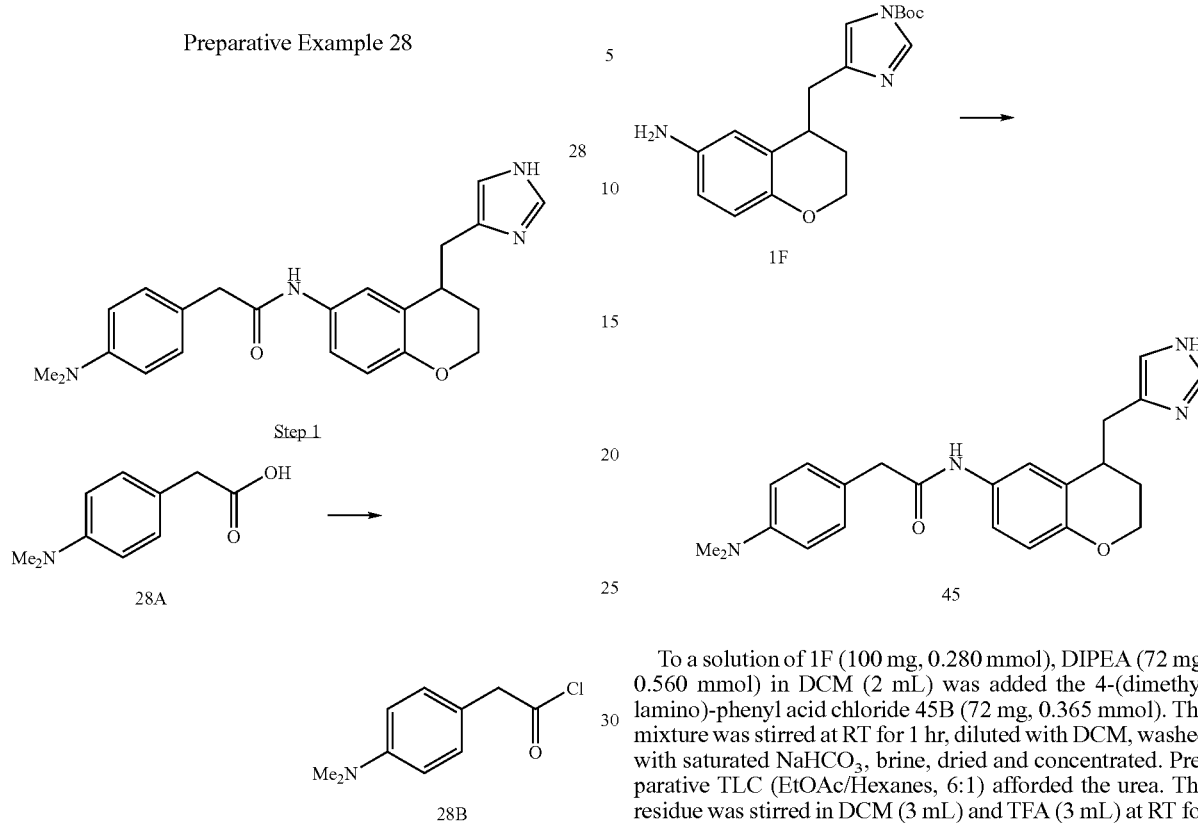

To a solution of 4-(dimethylamino)-phenylacetic acid 28A (155 mg, 0.862 mmol) in DCM (2 mL) was added oxalyl chloride (115 mg, 0.905 mmol) and catalytic amount of DMF. The mixture was stirred at RT for 30 min. Without further work-up, the mixture was concentrated in vacuo to give 28B (used directly in Step 2).

To a solution of 1F (100 mg, 0.280 mmol), DIPEA (72 mg, 0.560 mmol) in DCM (2 mL) was added the 4-(dimethylamino)-phenyl acid chloride 45B (72 mg, 0.365 mmol). The mixture was stirred at RT for 1 hr, diluted with DCM, washed with saturated NaHCO3, brine, dried and concentrated. Preparative TLC (EtOAc/Hexanes, 6:1) afforded the urea. The residue was stirred in DCM (3 mL) and TFA (3 mL) at RT for 1.5 h. The TFA and DCM were removed in vacuo. Preparative TLC (MeOH(7N NH3)/DCM, 1:10) afforded 45 (87 mg, 73%). MS m/z 391 (MH+).

Example 46

Example 46 was prepared following the procedure set forth in preparative example 45, except that the reagents listed in Table 4 below were used.

TABLE 4

| Ex. No. | Reagents | R | MH+ |
|---|---|---|---|
| 46 | ![4-(methylsulfonyl)phenylacetic acid, (COCl)2] | ![4-(methylsulfonyl)phenylacetamide R group] | 426 |

Preparative Example 47

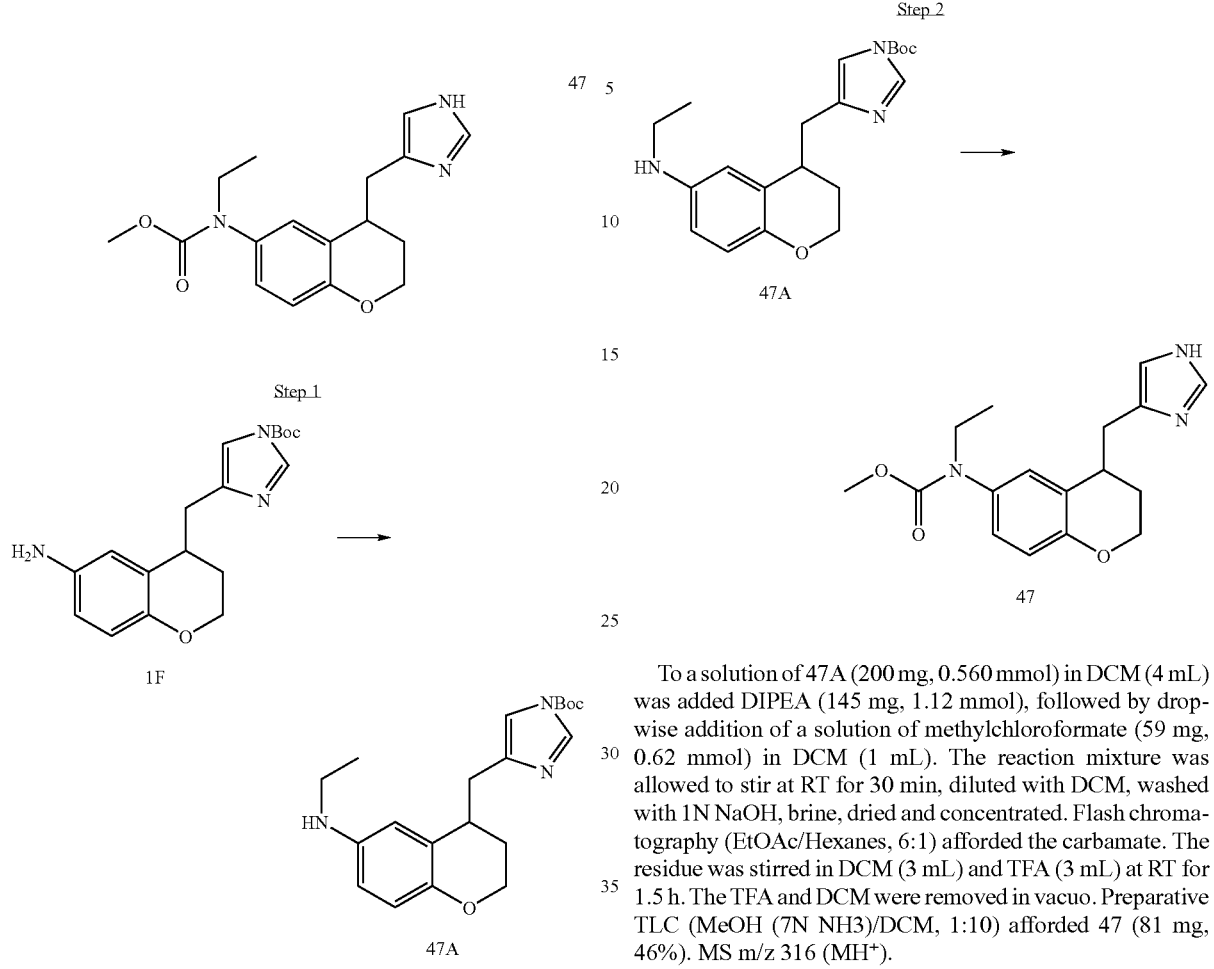

A mixture of 1F (1.1 g, 3.34 mmol) in MeOH (10 mL) and CH₃CN (10 mL) in presence of Pd/C (10%, 300 mg) was sirred at RT under H₂. The reaction was monitored with TLC. After 3 h, the starting material was consumed. The mixture was degassed, diluted with DCM, filtered and concentrated to give 47A (1.1 g, 96%)

To a solution of 47A (200 mg, 0.560 mmol) in DCM (4 mL) was added DIPEA (145 mg, 1.12 mmol), followed by dropwise addition of a solution of methylchloroformate (59 mg, 0.62 mmol) in DCM (1 mL). The reaction mixture was allowed to stir at RT for 30 min, diluted with DCM, washed with 1N NaOH, brine, dried and concentrated. Flash chromatography (EtOAc/Hexanes, 6:1) afforded the carbamate. The residue was stirred in DCM (3 mL) and TFA (3 mL) at RT for 1.5 h. The TFA and DCM were removed in vacuo. Preparative TLC (MeOH (7N NH3)/DCM, 1:10) afforded 47 (81 mg, 46%). MS m/z 316 (MH⁺).

Examples 48-57

Examples 48-57 were prepared following the procedure set forth in preparative example 47, except that the reagent(s) listed in Table 5 below were used.

TABLE 5

| Example No. | Reagents | R | MH⁺ |
|---|---|---|---|
| 48 | Acetyl chloride Et₃N | 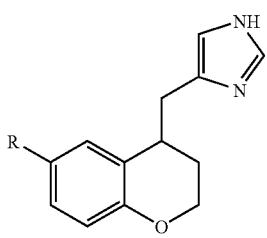 | 300 |

TABLE 5-continued

| Example No. | Reagents | R | MH+ |
|---|---|---|---|
| 49 | Cyclopropanecarbonyl chloride, Et₃N | N-ethyl-N-(cyclopropylcarbonyl) | 326 |
| 50 | Methoxyacetyl chloride, Et₃N | N-ethyl-N-(methoxyacetyl) | 330 |
| 51 | MeNCO | N-ethyl-N'-methyl urea | 315 |
| 52 | EtNCO | N-ethyl-N'-ethyl urea | 329 |
| 53 | PrNCO | N-ethyl-N'-propyl urea | 343 |
| 54 | 3-pyridyl NCO | N-ethyl-N'-(3-pyridyl) urea | 378 |
| 55 | 4-fluorobenzyl NCO | N-ethyl-N'-(4-fluorobenzyl) urea | 409 |
| 56 | Methanesulfonyl chloride, Et₃N | N-ethyl methanesulfonamide | 336 |

TABLE 5-continued

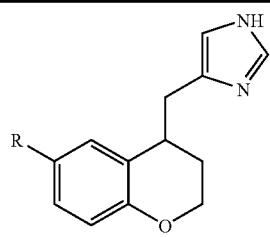

| Example No. | Reagents | R | MH+ |
|---|---|---|---|
| 57 | cyclopropanesulfonyl chloride, Et3N | cyclopropyl-S(O)2-N(Et)- | 362 |

Preparative Example 58

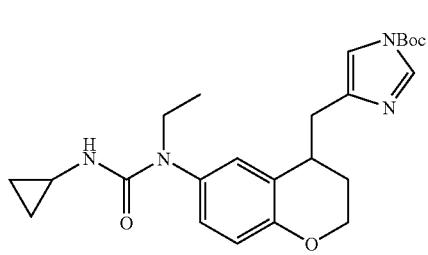

58

Step 1

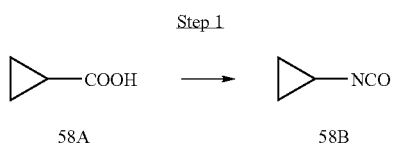

To a solution of cyclopropanecarboxylic acid 58A (868 mg, 10.1 mmol) in toluene (5 mL) was added TEA (1.33 g, 13.1 mmol) and DPPA (2.77 g, 10.1 mmol). The mixture was stirred at 100° C. for 1 hr. Without further work-up, the mixture was concentrated in vacuo to give 58B.

Step 2

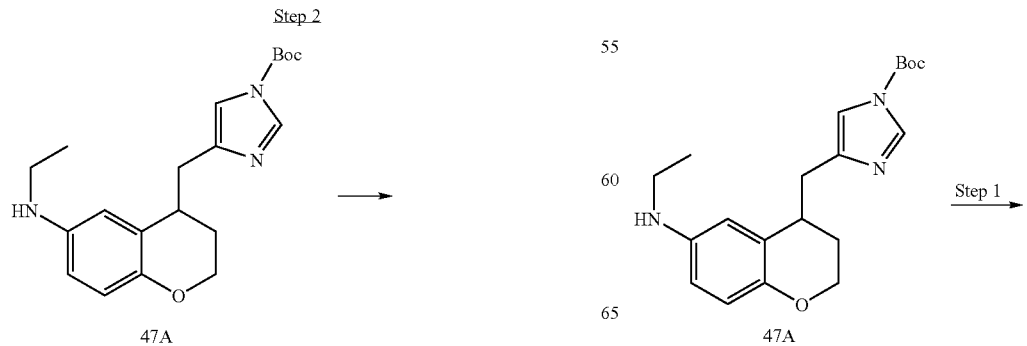

-continued

58

To a solution of 47A (100 mg, 0.280 mmol) in DCM (2 mL) was added the cyclopropane isocyanate (70 mg, 0.839 mmol). The mixture was stirred at RT for 1 hr, destroyed excess isocyanate with MeOH and concentrated. Preparative TLC (EtOAc/Hexanes, 6:1) afforded the urea. The residue was stirred in DCM (3 mL) and TFA (3 mL) at RT for 1.5 h. The TFA and DCM were removed in vacuo. Preparative TLC (MeOH(7N NH3)/DCM, 1:10) afforded 58 (86 mg, 90%). MS m/z 341 (MH+).

Preparative Example 59

Step 1

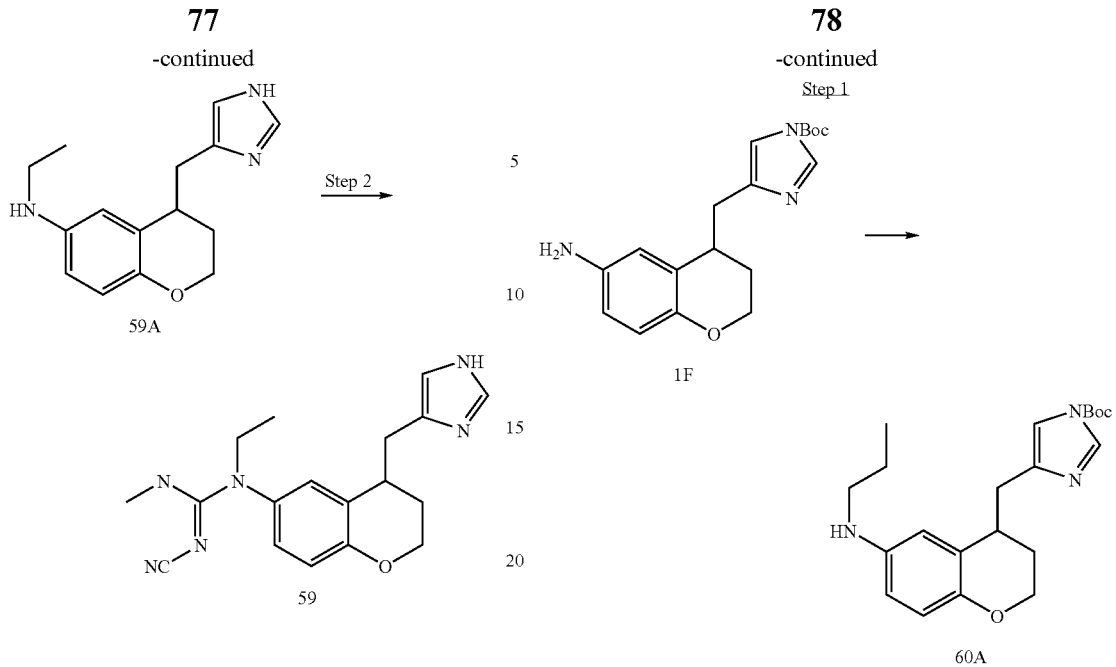

Step 1

To a stirred solution of aniline 47A (100 mg, 0.28 mmol), available from Preparative Example 47, step A, in 2 mL of $CH_2Cl_2$ was added 0.5 mL of trifluoroacetic acid. Reaction was continuted at room temperature for 2.5 h. Volatiles were removed in vacuo. The oily residue was dissolved in 50 mL of $CH_2Cl_2$, washed with a sat. $NaHCO_3$ aqueous solution and brine, dried over $Na_2SO_4$, and concentrated in vacuo to give 65 mg of the deprotected aniline 59A (90%, $MH^+$=258.05) as an oily solid.

Step 2

Aniline 59A (65 mg, 0.253 mmol), prepared from Step 1 above, was dissolved in 5 mL of acetonitrile, and added with diphenyl cyanocarbonimidate (90 mg, 0.378 mmol). The mixture was stirred at room temperature for 5 minutes. Solvent was removed in vacuo. The oily residue was heated at 70° C. over night. After cooling to room temperature, 2.5 mL of $CH_2Cl_2$ was added followed by a 2.0 M solution of methyl amine in THF (2.5 mL, 5 mmol). Reaction was continued at room temperature for 3 h. The mixture was concentrated, and separated by preparative TLC eluting with $CH_2Cl_2$-7N $NH_3$ in MeOH (20:1, v/v) to afford 55 mg of the titled product 59 (64%, $MH^+$=339.2)

Preparative Example 60

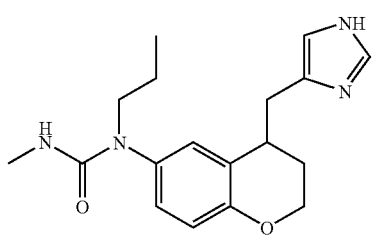

A mixture of 1F (300 mg, 0.912 mmol) in MeOH (10 mL) and $CH_3CH_2CN$ (10 mL) in presence of Pd/C (10%, 80 mg) was sirred at RT under $H_2$. The reaction was monitored with TLC. After 4 h, the starting material was consumed. The mixture was degassed, diluted with DCM, filtered and concentrated to give 60A (1.1 g, 96%)

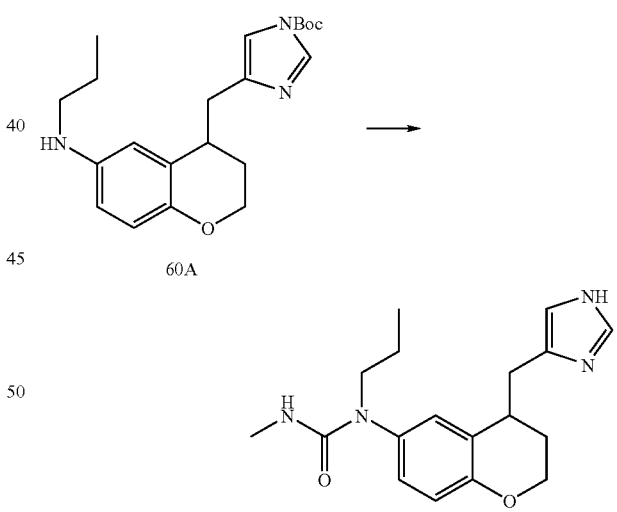

To a solution of 60A (90 mg, 0.243 mmol) in DCM (2 mL) was added MeNCO (42 mg, 0.727 mmol). The reaction mixture was allowed to stir at RT for 1 h. MeOH (1 mL) was added and the mixture was concentrated in vacuo. Preparative TLC (EtOAc/Hexanes, 4:1) afforded the urea. The residue was stirred in DCM (3 mL) and TFA (3 mL) at RT for 1.5 h. The TFA and DCM were removed in vacuo. Preparative TLC [MeOH (7N $NH_3$)/DCM, 1:10] afforded 60 (46 mg). MS m/z 329 ($M^+$).

Example 61

Example 61 was prepared following the procedure set forth in preparative example 60, except that the reagents listed in Table 8 below were used.

TABLE 8

| Example No. | Reagents | R | MH+ |
|---|---|---|---|
| 61 | Methylchloroformate Et₃N | (methyl carbamate group) | 316 |

Preparative Example 62

To a solution of 4-iodo-trityl-imidazole (6.77 g, 15.5 mmol) in DCM (100 mL) was added EtMgBr (3.0M in Et₂O, 4.96 mL, 14.9 mmol) slowly at −20° C., stirred at −20° C. for 30 min. A solution of 1C (2.8 g, 13.5 mol) in DCM (20 mL) was added very slowly. The mixture was stirred at RT for 1 h, quenched with saturated NH₄Cl, diluted with DCM. The DCM layer was washed with brine, dried and concentrated. Flash chromatography (EtOAc/Hexanes, 1:2 then 10:1) afforded 62A (5.0 g, 72%).

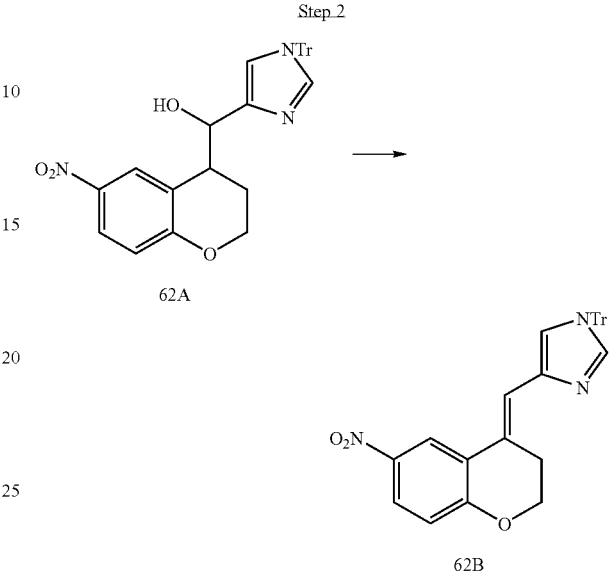

To a solution of 62A (3.0 g, 5.803 mmol) in DCM (120 mL) was added Et₃N (880 mg, 8.704 mmol), followed by dropwise addition of MsCl (800 mg, 6.963 mmol) in DCM (3 mL) at RT. The mixture was stirred at RT for 1 h. DBU (7.06 g, 46.4 mmol) was added in one portion. The mixture was stirred in a pressure flask at 65° C. for 2 h. The mixture was cooled down to RT, concentrated to 40 mL. Flash chromatography (EtOAc/DCM, 1:4) afforded 62B (1.75 g, 60%).

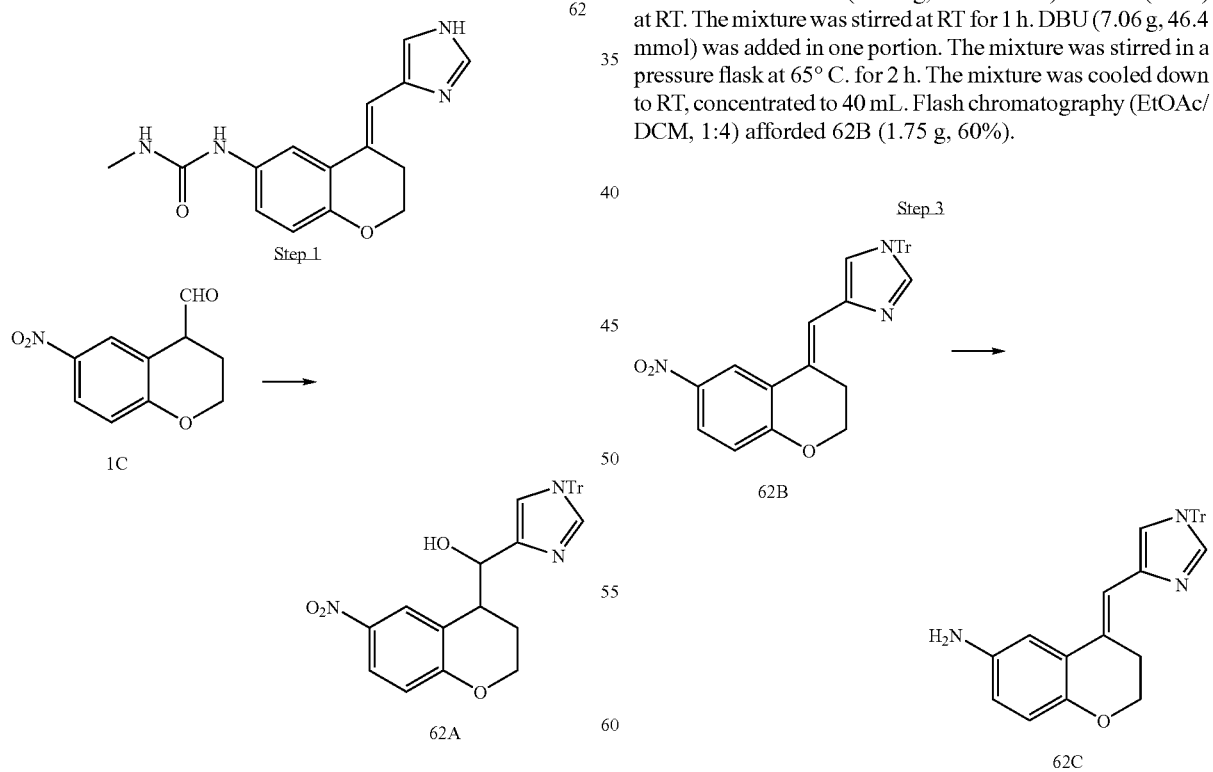

To a solution of 62B (1.3 g, 2.61 mmol) in DCM (20 mL) and THF (10 mL) was added Cu(OAc)₂ (1.6 g mg, 8.704 mmol). The mixture was stirred at RT for 15 min. Five portions of NaBH₄ (300 mg, 7.83 mmol) were added every 5 min.

The mixture was stirred at RT for 10 min, filtered through a pad of celite, washed with DCM. The filtrate was concentrated. Flash chromatography (EtOAc/DCM, 2:1) afforded 62C (700 mg, 60%).

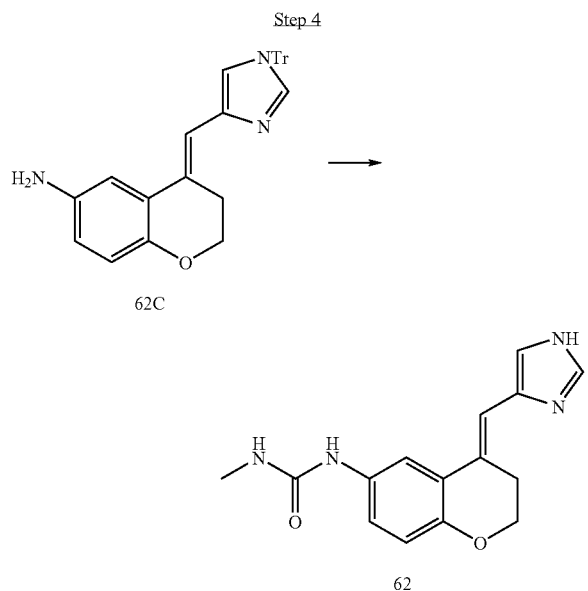

To a solution of 62C (90 mg, 0.192 mmol) in DCM (2 mL) was added MeNCO (246 mg, 2.431 mmol). The reaction mixture was stirred at RT for 1 h. MeOH (1 mL) was added. The mixture was stirred for 20 min and concentrated. Preparative TLC (MeOH/DCM, 1:10) afforded the urea. The residue was stirred in DCM (3 mL), TFA (3 mL) and Et3SiH (0.2 mL) at RT for 1.5 h. The mixture was concentrated in vacuo. Preparative TLC (MeOH (7N NH$_3$)/DCM, 1:10) afforded 62 (30 mg). MS m/z 285 (MH$^+$).

Preparative Example 63

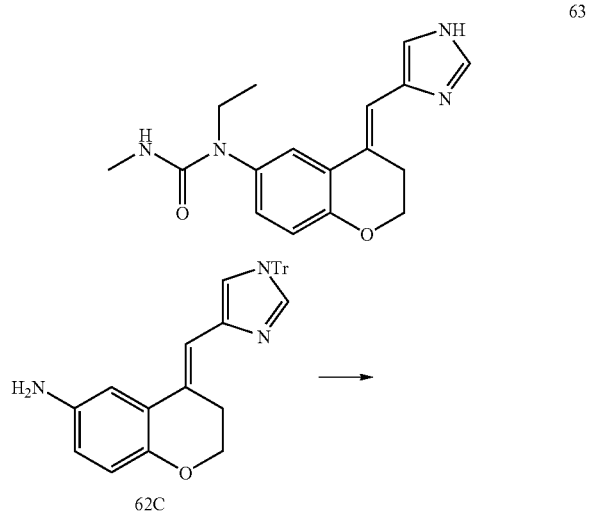

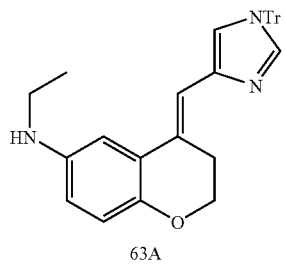

To a solution of 62C (600 mg, 1.28 mmol) in DCM (10 mL) was added Et$_3$N (646 mg, 6.40 mmol), followed by Ac$_2$O (392 mg, 3.84 mmol). The reaction mixture was allowed to stir at RT for 12 h, diluted with DCM, washed with 1N NaOH, brine, dried and concentrated. Flash chromatography (EtOAc/DCM, 6:1) afforded the acetylated intermediate. The residue was dissolved in THF (20 mL). LAH (1.0 M in Et$_2$O, 3.84 mL, 3.84 mmol) was added. The mixture was stirred at RT for 1 h. Additional LAH (1.0 M in Et$_2$O, 3.84 mL, 3.84 mmol) was added. The reaction mixture was stirred at RT for 12 h and then cooled to 0° C. MeOH (2 mL) was added very slowly followed by dropwise addition of H$_2$O to quench the reaction. The mixture was then diluted with DCM, washed with 1N NaOH, dried and concentrated. Flash chromatography (EtOAc/DCM, 2:1) afforded 63A (310 mg).

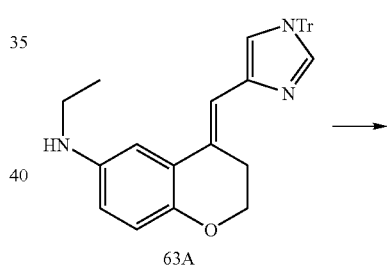

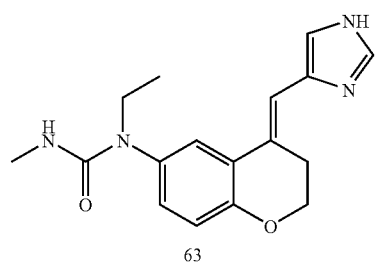

To a solution of 63A (160 mg, 0.322 mmol) in DCM (5 mL) was added MeNCO (1.0 M in DCM, 1.60 mL, 1.60 mmol). The reaction mixture was stirred at RT for 1 h. MeOH (1 mL) was added. The mixture was stirred for 20 min and concentrated. Preparative TLC (MeOH/DCM, 1:10) afforded the urea. The residue was stirred in DCM (3 mL), TFA (3 mL) and Et$_3$SiH (0.1 mL) at RT for 1.5 h. The mixture was concentrated in vacuo. Preparative TLC (MeOH (7N NH$_3$)/DCM, 1:10) afforded 63 (48 mg, 48%). MS m/z 313 (MH$^+$).

83

Alternatively, 63 Could be Prepared from 1A:

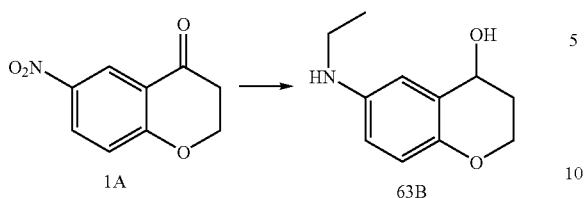

A mixture of compound 1A (6.0 g, 3.1 mmol) and catalytic 10% Pd/C in EtOH (70 mL) was hydrogenated at 45 psi $H_2$ overnight. The reaction was filtered through celite and concentrated. The resulting 6-aminochroman-4-ol (3.26 g, 2.0 mmol) was dissolved in MeOH (40 mL), treated with $CH_3CN$ (20 mL) and 10% Pd/C (100 mg), and then hydrogenated under 1 atm of hydrogen. After 3.5 h, the mixture was filtered and concentrated to provide 63B (quantitative yield).

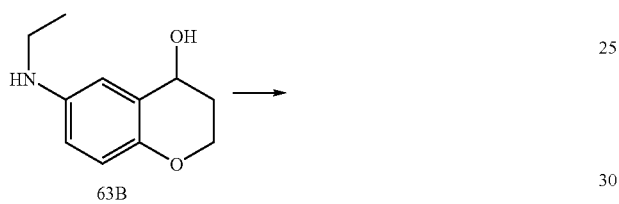

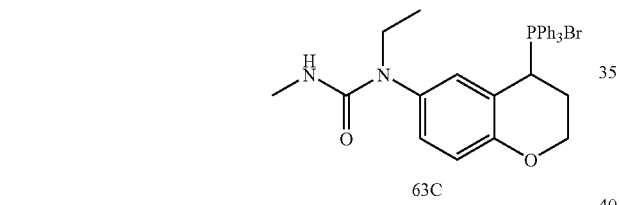

A solution of 63B (2.6 g, 13.6 mmol) in DCM (30 mL) was cooled in an ice bath and treated dropwise with MeNCO (1.0 g, 17.5 mmol). The reaction was stirred at 0° C. for 4 h and then quenched with MeOH. After 10 minutes, the mixture was diluted with water and extracted with EtOAc (3×). The combined organic extracts were washed with brine, dried over $Na_2SO_4$, and concentrated (82% yield).

The resulting methyl urea (1.5 g, 6.0 mmol) was combined with triphenylphosphine-HBr (2.06 g, 6.0 mmol) and suspended in benzene (5 mL, sealed tube). The mixture was heated at 100° C. overnight and then cooled to RT. The top liquid layer was removed. The bottom solid material was washed with benzene and then dried under vacuum to give the crude phosphonium salt 63C.

A mixture of imidazole-4-carboxaldehyde (96 mg, 1.0 mmol) in EtOH (2 mL) as treated with KOtBu (1N in THF, 1 mL), warmed until homogeneous, and then treated dropwise with a solution of phosphonium salt 63C (440 mg, 0.77 mmol) in EtOH (2 mL). The mixture was stirred at 50° C. for 3 h and then treated with another portion of imidazole-4-carboxaldehyde (96 mg, 1.0 mmol) and KOtBu (1N in THF, 1 mL). After stirring an additional 3 h at 50° C., the mixture was cooled, diluted with water and extracted with EtOAc (3×). The combined organic extracts were washed with brine,

84 dried over $Na_2SO_4$, and concentrated to give the E-olefinic isomer 63 and a minor Z-isomer (86 mg, 36% total yield).

Preparative Example 64

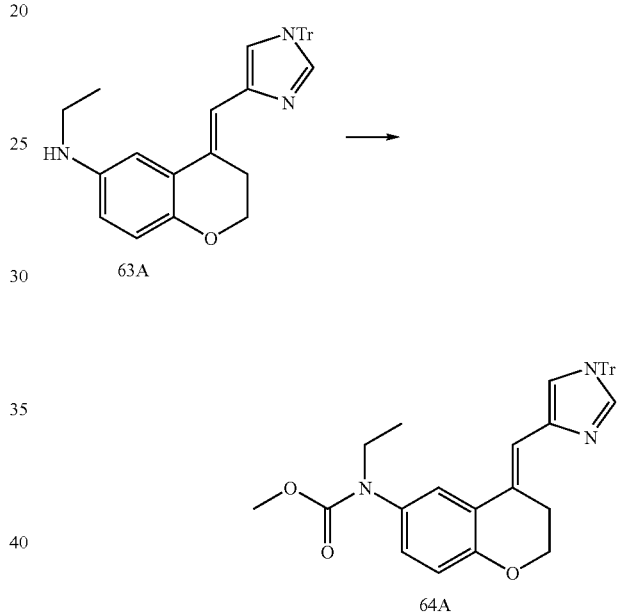

To a solution of 63A (800 mg, 1.61 mmol) in DCM (5 mL) at −78° C. was added DIPEA (415 mg, 3.22 mmol), followed by dropwise addition of a solution of methylchloroformate (167 mg, 1.77 mmol) in DCM (1 mL). The reaction mixture was allowed to stir for 10 min at −78° C., then RT for 30 min, diluted with DCM, washed with 1N NaOH, brine, dried and concentrated. Flash chromatography (EtOAc/Hexanes, 4:1) afforded the carbamate 64A (620 mg).

Alternatively, 64A Could be Prepared from 62C

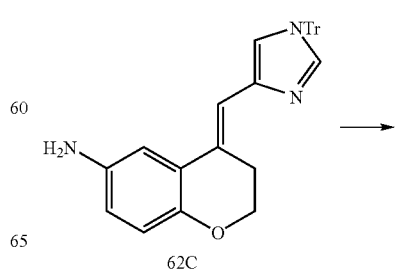

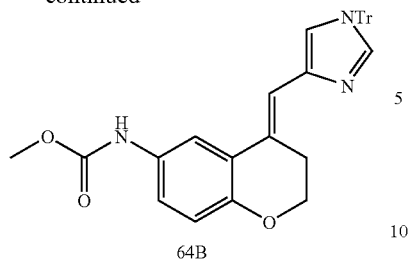

64B

To a solution of 62C (1.0 g, 2.0 mmol) in dry DCM at −78° C. was added diisopropylethylamine (0.83 g, 0.6.4 mmol), followed by dropwise addition of methyl chloroformate (0.23 g, 2.4 mmol). The reaction mixture was warmed to 0° C. slowly, quenched with saturated NaHCO₃ and diluted with DCM. The organic layer was washed with NaHCO₃ (sat.), dried over MgSO₄, filtered, and concentrated in vacuo. Flash chromatography (EtOAc:Hex, 1:2 then 1:1) afforded 64B (800 mg, 71%).

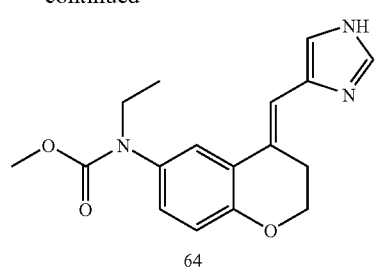

64

The carbamate 64A was stirred in DCM (10 mL), TFA (10 mL) and Et₃SiH (0.1 mL) at RT for 2 h. The TFA and DCM was removed in vacuo. Flash chromatograpy [MeOH(7N NH3)/DCM, 1:20 then 1:15] afforded 64 (330 mg, 66%). MS m/z 314 (MH⁺).

Preparative Example 65

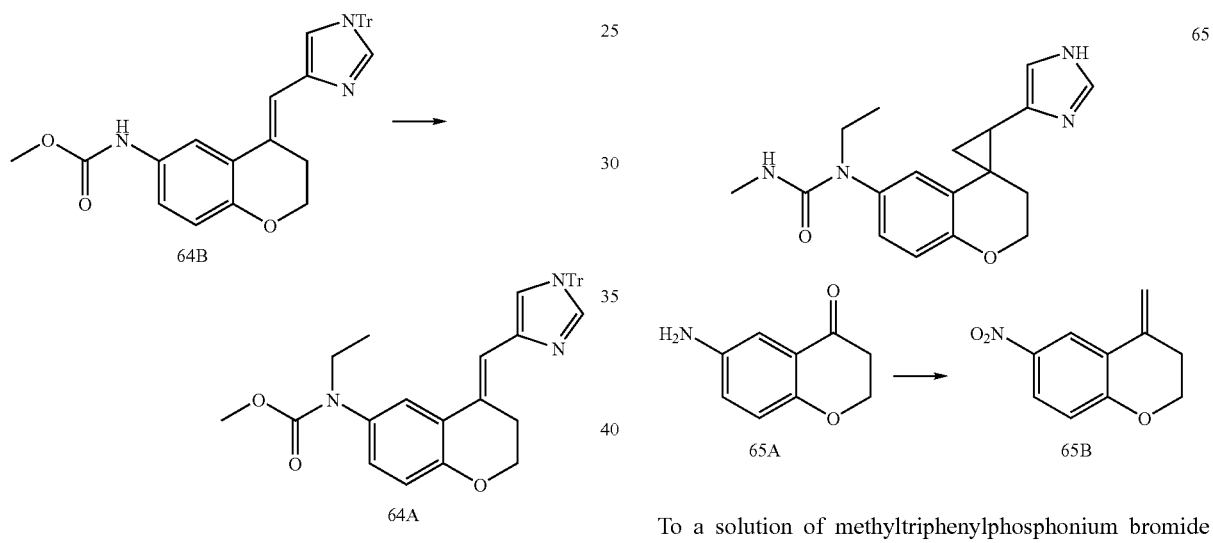

To a solution of 64B (500 mg, 0.95 mmol) in acetone was added Cs₂CO₃ (1.85 g, 5.7 mmol) and EtI (296 mg, 1.9 mmol) at room temperature. The reaction mixture was stirred at 50° C. for 14 h, cooled to room temperature. The mixture was diluted with DCM, filtered through a pad of celite and concentrated in vacuo. The residue was dissolved with DCM, washed with H₂O and concentrated in vacuo. Flash chromatography (EtOAc:Hex 1:3 then 1:1) afforded 64A (360 mg, 68%).

To a solution of methyltriphenylphosphonium bromide (66.6 g, 0.186 mol) in THF (600 mL) was added phenyllithium (1.8M in Et₂O, 103 mL, 0.186 mol) slowly at −30° C. via an addition funnel. Reaction mixture was stirred at 0° C. for 30 min. A suspension of 65A 6-nitrochroman-4-one (30.0 g, 0.155 mmol) in THF was added slowly to the reaction mixture at −30° C. using an additional funnel. Stir reaction mixture at room temperature for 30 min. Quenched reaction mixture with 1N NaOH and diluted with Et₂O. Et₂O layer is washed with 1N NaOH, dried with MgSO₄, filtered, and concentrated in vacuo. Flash chromatography (EtOAc/Hexanes, 1:9 then 1:6) afforded 65B (17.7 g, 59%).

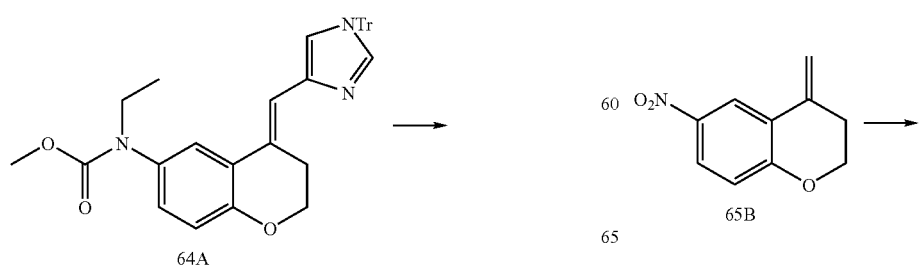

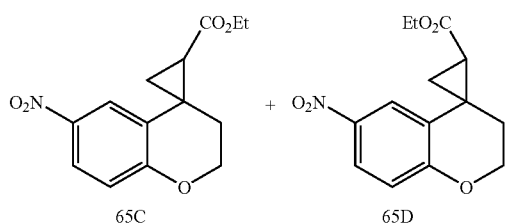

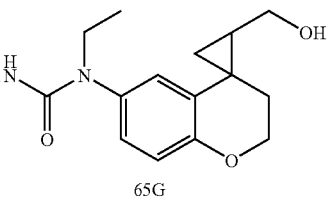

To a solution of 65B (17.7 g, 92.6 mmol) in DCM (200 mL) was added rhodium(II) acetate dimer (2.21 g, 5.0 mmol). A solution of ethyldiazoacetate (21.1 g, 0.185 mol) in DCM (50 mL) was added to the reaction mixture via a syringe pump over 12 hrs. Once the reaction was complete, reaction mixture was diluted with DCM. The DCM layer was washed with 1N NaOH twice, dried with MgSO₄, filtered, and concentrated in vacuo. Flash chromatography (EtOAc/Hexanes, 1:9 then 1:4) afforded the trans isomer 65C (10.6 g, 41%) and the cis isomer 65D (11.0 g, 43%).

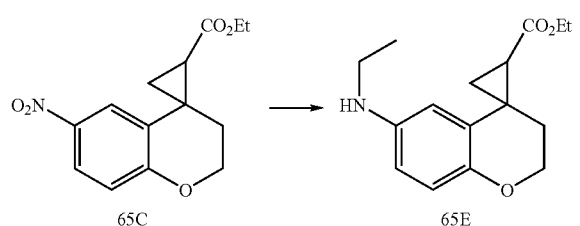

To a solution of 65F (1.6 g, 4.82 mmol) in THF (50 mL) at −78° C. was added DIBAL (1.0M in DCM, 16.9 mL, 16.9 mmol). The mixture was stirred at −78° C. for 30 min and warmed up to −0° C. slowly. The reaction mixture was quenched with 1N NaOH, diluted with DCM. The organic phase was dried and concentrated. Flash chromatography (EtOAc) afforded 65G (1.4 g, 100%).

A solution of 65C (4.0 g, 0.014 mol) in MeOH (25 mL) and CH₃CN (15 mL) with Pd/C (10%, 300 mg) was stirred under H₂ at atmospheric pressure. The reaction was monitored closely with TLC. After 3 h, the mixture was degassed, filtered through a pad of celite and concentrated. Flash chromatography (EtOAc/Hexanes, 1:4) afforded 65E (3.2 g, 80%).

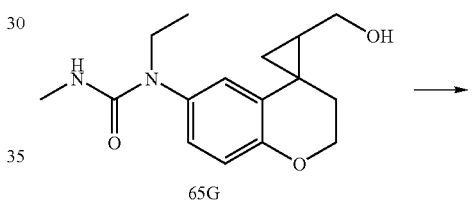

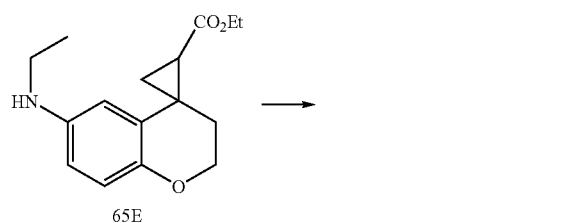

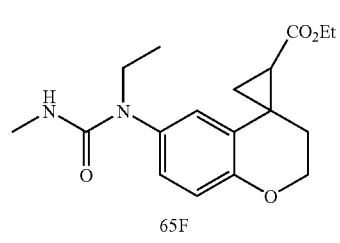

To a solution of 65E (1.6 g, 5.82 mmol) in DCM (30 mL) was added MeNCO (500 mg) in one portion. The solution was stirred at RT for 10 min. MeOH (2 mL) was added. The mixture was stirred for 5 min and concentrated. Flash chromatography (EtOAc/Hexanes, 1:1) afforded 65F (1.6 g, 83%).

To a solution of alcohol 65G (1.4 g, 4.878 mmol) in DCM (30 mL) was added pyridine (578 mg, 7.317 mmol), followed by Dess-Martin Periodinane (2.9 g, 6.829 mmol). The mixture was stirred at RT for 30 min, quenched with saturated Na₂S₂O₃ and 1N NaOH, diluted with DCM. The organic phase was dried and concentrated. Flash chromatography (EtOAc/Hexanes, 1:2) afforded 65H (1.0 g, 72%).

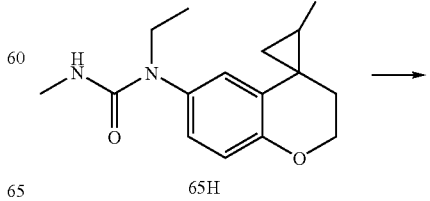

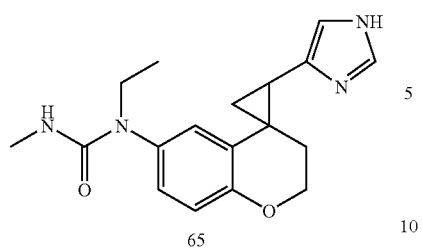

65

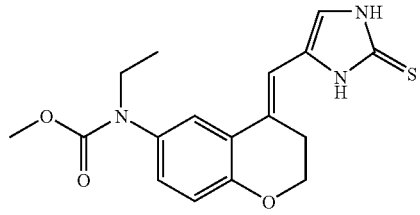

68

To a solution of 65H (400 mg, 1.39 mmol) in EtOH (10 mL) was added p-toluenesulfonylmethyl isocyanide (271 mg, 1.39 mmol) in one portion, followed by catalytic amount of NaCN. The mixture was stirred at RT for 30 min and then concentrated in vacuo. The residue was dissolved in MeOH (7N $NH_3$, 5 mL). The solution was heated in a sealed tube at 90° C. for 18 h. The mixture was cooled to RT and concentrated in vacuo. Prep TLC M:C=1:15 afforded 65 (95 mg, 21%). LMCS m/z 327 ($MH^+$).

A mixture of compound 64 (0.50 g, 1.6 mmol) and $NaHCO_3$ (1.34 g, 16.0 mmol) in 1:1 THF-$H_2O$ (40 mL) was stirred for 20 min at 20° C. min and then treated with phenyl chlorothionoformate (0.55 mL, 4.0 mmol). The reaction was stirred at 20° C. for 2 h and then diluted with EtOAc. The organic layer was isolated, dried over $Na_2SO_4$ and concentrated. The resulting residue was dissolved in MeOH, treated with $Et_3N$ (1.1 mL, 8.0 mmol), and stirred overnight. at 20° C. The solution was concentrated and diluted with water, and extracted with DCM (3×). The combined organic layer was dried over $Na_2SO_4$, concentrated and subjected to chromatography (2-5% of 7N $NH_3$-MeOH/DCM) to provide the title compound 68. LMCS m/z 346 ($MH^+$).

Preparative Example 69

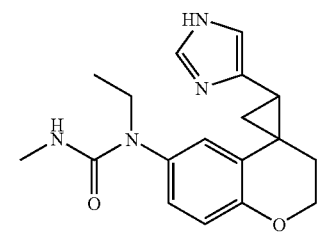

66

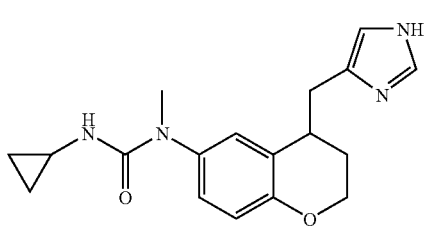

69

Steps 1-2

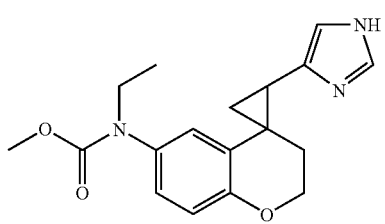

67

Examples 66 and 67 were prepared in analogous manner from 65D/MeNCO and 65C/$ClCO_2Me$, respectively. LMCS for 66 m/z 327 ($MH^+$). LMCS for 67 m/z 328 ($MH^+$).

Preparative Example 68

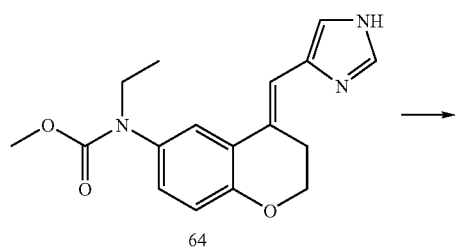

64

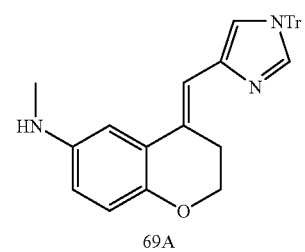

69A

A sample of $Ac_2O$ (1.0 g, 9.78 mmol) was cooled at 0° C. and treated with $HCO_2H$ (0.45 g, 9.78 mmol). After stirring for 5 min at 0° C. for 5 min, the temperature was raised to 55° C. for 2 h. The reaction was then cooled to 0° C. and treated with a solution of 62A (1.7 g, 3.62 mmol) in THF (50 mL). After stirring for 30 min at 0° C., the reaction was diluted with EtOAc. This mixture was then washed with 1N NaOH, dried over $Mg_2SO_4$, filtered and concentrated.

The resulting formamide (1.5 g, 3.0 mmol) was dissolved in THF (35 mL), and treated with LAH (3.0 mL., 1 M in Et₂O) at 0° C. After stirring for 1 h at 20° C., the reaction was cooled to 0° C., and treated with additional LAH (4.0 mL., 1 M in Et₂O). Upon complete reaction, the mixture was sequentially quenched with MeOH and 1 N aq. NaOH and then extracted with EtOAc. The combined organic layer was dried (MgSO₄), filtered and concentrated. Chromatography (40-60% EtOAc/hexanes) provided 69A (1.2 g).

Steps 3-4

In a manner similar to that described in Example 58, compound 69A was reacted with isocyanate 58B and then deprotected with TFA to provide compound 69. LMCS m/z 327 (MH⁺).

Preparative Example 70

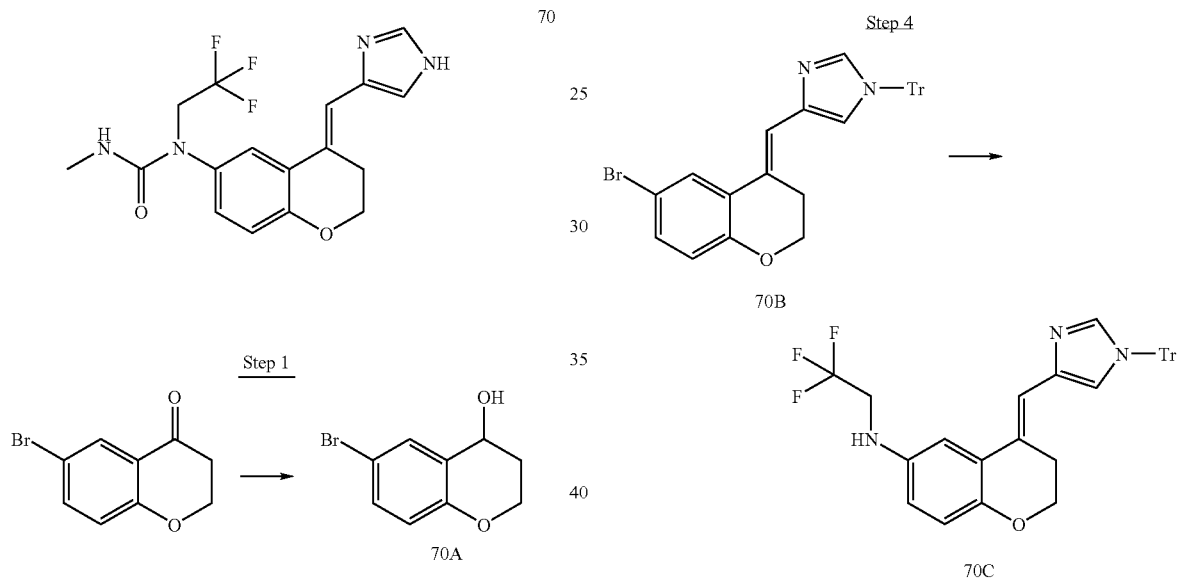

In a manner similar to that described in the literature (J. Med. Chem. 2205, 48, 1796), a solution of 6-bromo-chroman-4-one (10 g) in 1:1 MeOH:DCM (100 mL) was cooled an ice bath, treated with NaBH₄ (1.63 g), and then stirred at RT. After 2 h, the reaction was then worked up with water and EtOAc to provide compound 70A in nearly quantitative yield. The product was used in the next step without chromatographic purification.

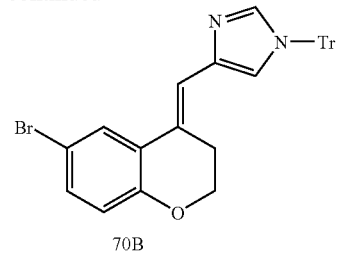

In a manner similar to that described in Example 63, compound 70A was sequentially treated with triphenylphosphine-HBr in benzene (refluxed 2d). As described in Example 65, the resulting phosphonium salt was sequentially treated with phenyllithium (THF, −78° C., 45 min) and trityl-imidazole-4-carboxaldehyde (THF, warmed to RT overnight) to afford compound 70B.

A sealed tube was charged with 70B (1.06 g, 2.0 mmol), K₃PO₄ (0.8 g, 2 eq), CuI (0.38 g, 1.0 eq), 2,2,2-trifluoroethylamine (400 mg, 2 eq), 2-acetylcyclohexanone (0.26 mL) and DMF (10 mL). The reaction was heated at 100° C. for one day and then concentrated. DCM and H₂O were added and the layers were separated. The organic layer was washed with brine (3×), dried over Na₂SO₄, filtered and concentrated. Chromatography (7N NH₃-MeOH in DCM) provided 70C.

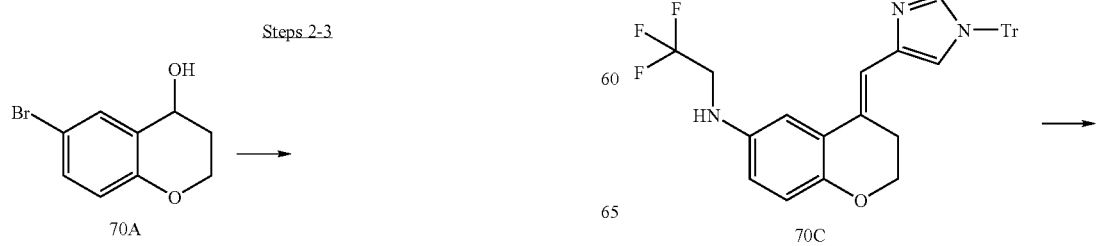

-continued

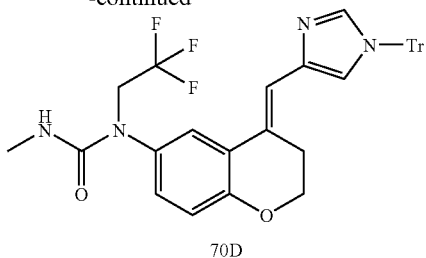
70D

In a manner similar to that found in Example 60 (Step 2), compound 70C was treated with MeNCO (100° C., toluene, 2d) to afford 70D.

Compound 70D was deprotected with TFA/Et₃SiH as described in Example 63 to afford the title compound 70. MS m/z 367 (MH⁺).

The following compounds were prepared following essentially the same procedures as in the examples above.

| Cpd | Structure | Spectral Data MS (MH+) unless noted |
|---|---|---|
| 100 | 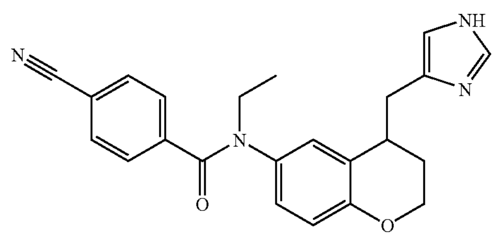 [SMILES: CCN(C(=O)c1ccc(C#N)cc1)c1ccc2c(c1)C(Cc1c[nH]cn1)CCO2] | 387 |
| 101 | 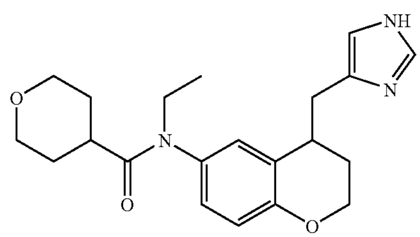 [SMILES: CCN(C(=O)C1CCOCC1)c1ccc2c(c1)C(Cc1c[nH]cn1)CCO2] | 370 |
| 102 | 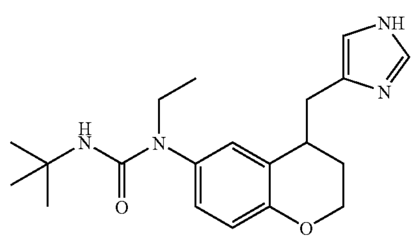 [SMILES: CCN(C(=O)NC(C)(C)C)c1ccc2c(c1)C(Cc1c[nH]cn1)CCO2] | 357 |
| 103 | 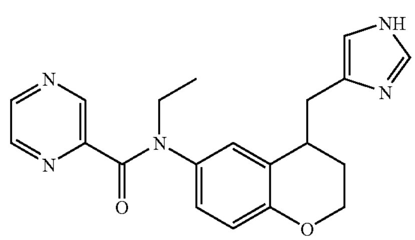 [SMILES: CCN(C(=O)c1cnccn1)c1ccc2c(c1)C(Cc1c[nH]cn1)CCO2] | 364 |
| 104 | 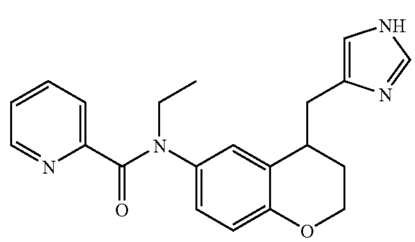 [SMILES: CCN(C(=O)c1ccccn1)c1ccc2c(c1)C(Cc1c[nH]cn1)CCO2] | 363 |

-continued

| Cpd | Structure | Spectral Data MS (MH+) unless noted |
|---|---|---|
| 105 | 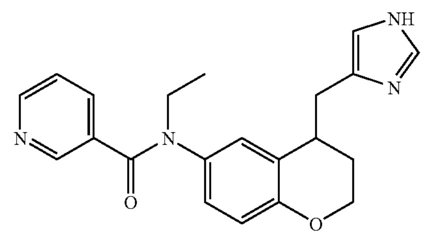 [SMILES: CCN(C(=O)c1cccnc1)c1ccc2c(c1)C(Cc1c[nH]cn1)CCO2] | 363 |
| 106 | 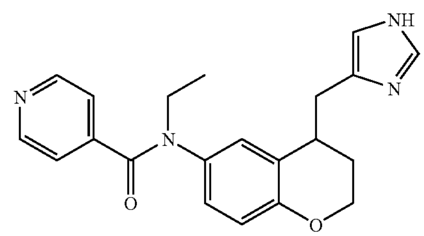 [SMILES: CCN(C(=O)c1ccncc1)c1ccc2c(c1)C(Cc1c[nH]cn1)CCO2] | 363 |
| 107 | 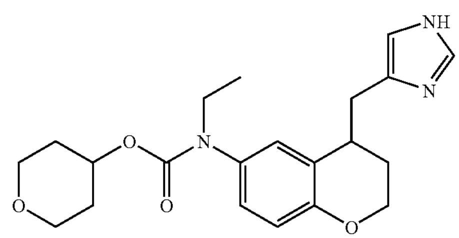 [SMILES: CCN(C(=O)OC1CCOCC1)c1ccc2c(c1)C(Cc1c[nH]cn1)CCO2] | 386 |
| 108 | 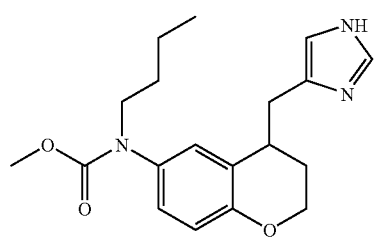 [SMILES: CCCCN(C(=O)OC)c1ccc2c(c1)C(Cc1c[nH]cn1)CCO2] | 344 |
| 109 | 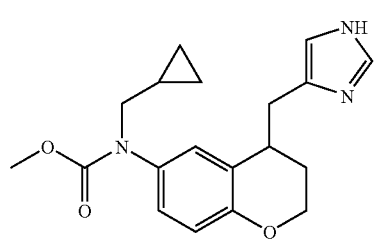 [SMILES: COC(=O)N(CC1CC1)c1ccc2c(c1)C(Cc1c[nH]cn1)CCO2] | 342 |
| 110 | 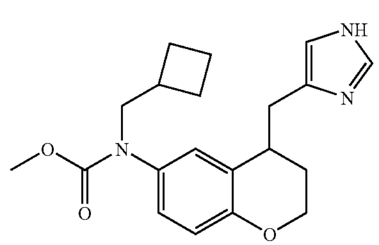 [SMILES: COC(=O)N(CC1CCC1)c1ccc2c(c1)C(Cc1c[nH]cn1)CCO2] | 356 |

-continued

| Cpd | Structure | Spectral Data MS (MH+) unless noted |
|---|---|---|
| 111 | 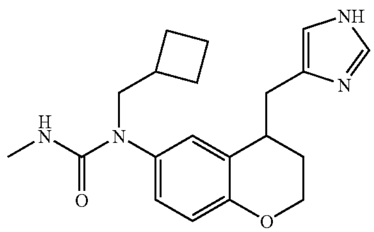 [SMILES: CNC(=O)N(CC1CCC1)c1ccc2c(c1)C(Cc1c[nH]cn1)CCO2] | 355 |
| 112 | 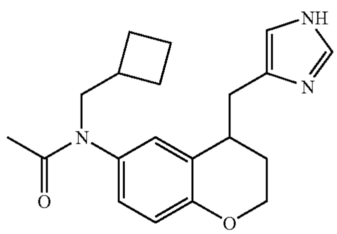 [SMILES: CC(=O)N(CC1CCC1)c1ccc2c(c1)C(Cc1c[nH]cn1)CCO2] | 340 |
| 113 | 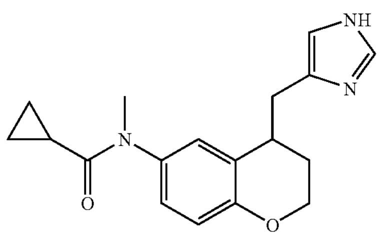 [SMILES: CN(C(=O)C1CC1)c1ccc2c(c1)C(Cc1c[nH]cn1)CCO2] | 312 |
| 114 | 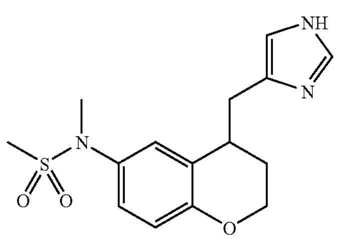 [SMILES: CN(c1ccc2c(c1)C(Cc1c[nH]cn1)CCO2)S(C)(=O)=O] | 322 |
| 115 | 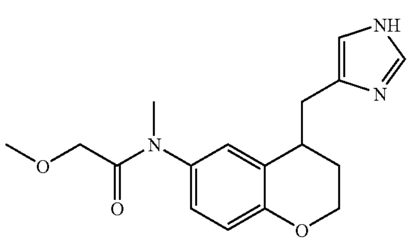 [SMILES: COCC(=O)N(C)c1ccc2c(c1)C(Cc1c[nH]cn1)CCO2] | 316 |
| 116 | 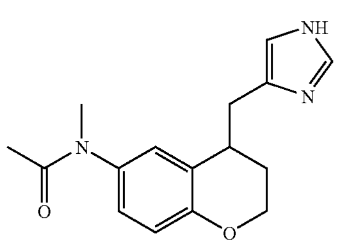 [SMILES: CC(=O)N(C)c1ccc2c(c1)C(Cc1c[nH]cn1)CCO2] | 286 |

-continued

| Cpd | Structure | Spectral Data MS (MH+) unless noted |
|---|---|---|
| 117 | 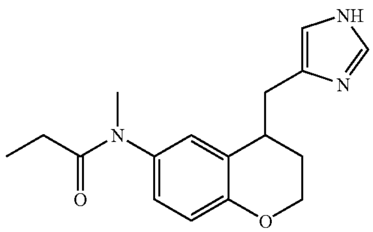 | 300 |
| 118 | 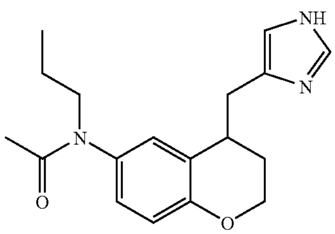 [SMILES: CCCN(C(C)=O)c1ccc2c(c1)C(Cc1c[nH]cn1)CCO2] | 314 |
| 119 | 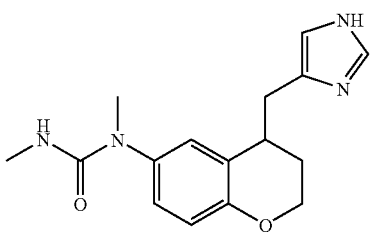 [SMILES: CNC(=O)N(C)c1ccc2c(c1)C(Cc1c[nH]cn1)CCO2] | 301 |
| 120 | 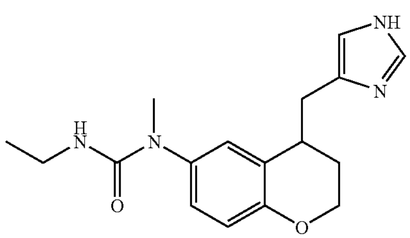 [SMILES: CCNC(=O)N(C)c1ccc2c(c1)C(Cc1c[nH]cn1)CCO2] | 315 |
| 121 | 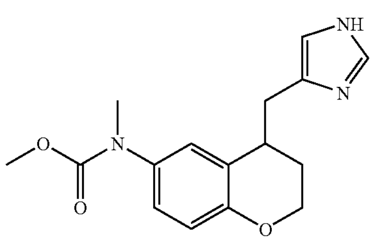 [SMILES: COC(=O)N(C)c1ccc2c(c1)C(Cc1c[nH]cn1)CCO2] | 302 |
| 122 | 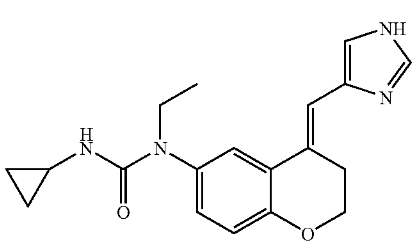 [SMILES: CCN(C(=O)NC1CC1)c1ccc2c(c1)/C(=C/c1c[nH]cn1)CCO2] | 339 |

-continued

| Cpd | Structure | Spectral Data MS (MH+) unless noted |
|---|---|---|
| 123 | 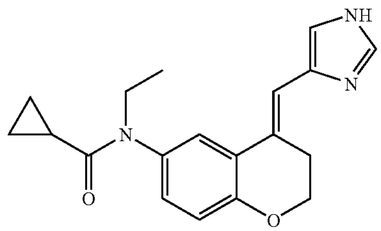 [SMILES: CCN(C(=O)C1CC1)c1ccc2c(c1)/C(=C/c1c[nH]cn1)CCO2] | 324 |
| 124 | 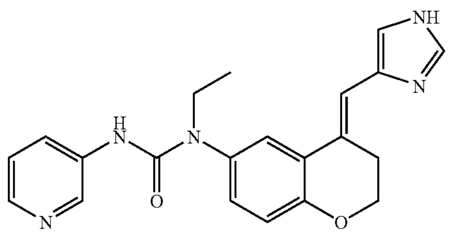 [SMILES: CCN(C(=O)Nc1cccnc1)c1ccc2c(c1)/C(=C/c1c[nH]cn1)CCO2] | 376 |
| 125 | 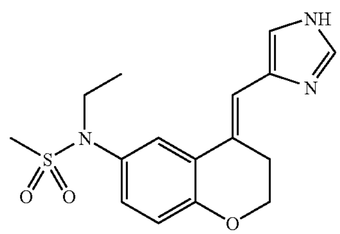 [SMILES: CCN(c1ccc2c(c1)/C(=C/c1c[nH]cn1)CCO2)S(C)(=O)=O] | 334 |
| 126 | 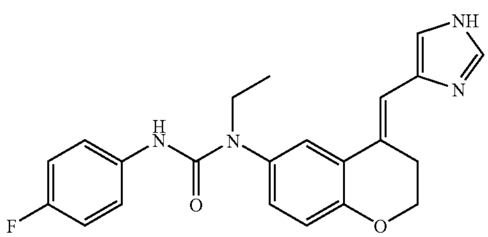 [SMILES: CCN(C(=O)Nc1ccc(F)cc1)c1ccc2c(c1)/C(=C/c1c[nH]cn1)CCO2] | 393 |
| 127 | 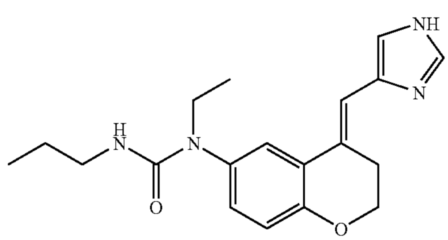 [SMILES: CCCNC(=O)N(CC)c1ccc2c(c1)/C(=C/c1c[nH]cn1)CCO2] | 341 |
| 128 | 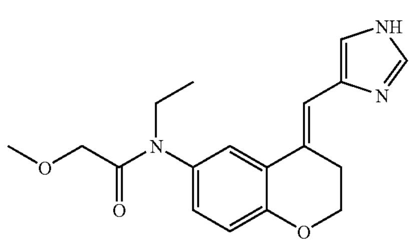 [SMILES: CCN(C(=O)COC)c1ccc2c(c1)/C(=C/c1c[nH]cn1)CCO2] | 328 |

-continued

| Cpd | Structure | Spectral Data MS (MH+) unless noted |
|---|---|---|
| 129 | 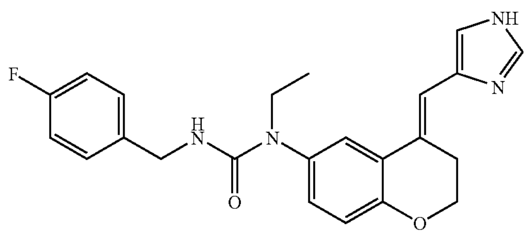 [SMILES: CCN(C(=O)NCc1ccc(F)cc1)c1ccc2c(c1)/C(=C/c1c[nH]cn1)CCO2] | 407 |
| 130 | 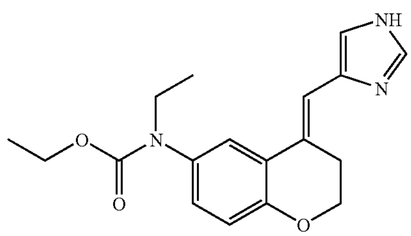 [SMILES: CCOC(=O)N(CC)c1ccc2c(c1)/C(=C/c1c[nH]cn1)CCO2] | 328 |
| 131 | 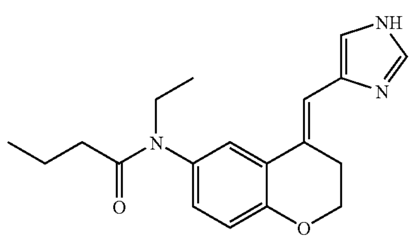 [SMILES: CCCC(=O)N(CC)c1ccc2c(c1)/C(=C/c1c[nH]cn1)CCO2] | 326 |
| 132 | 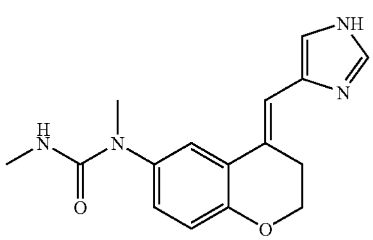 [SMILES: CNC(=O)N(C)c1ccc2c(c1)/C(=C/c1c[nH]cn1)CCO2] | 299 |
| 133 | 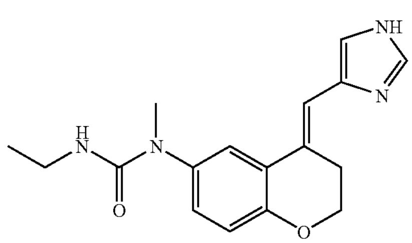 [SMILES: CCNC(=O)N(C)c1ccc2c(c1)/C(=C/c1c[nH]cn1)CCO2] | 313 |
| 134 | 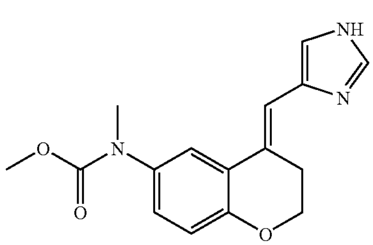 [SMILES: COC(=O)N(C)c1ccc2c(c1)/C(=C/c1c[nH]cn1)CCO2] | 300 |

-continued

| Cpd | Structure | Spectral Data MS (MH+) unless noted |
|---|---|---|
| 135 | 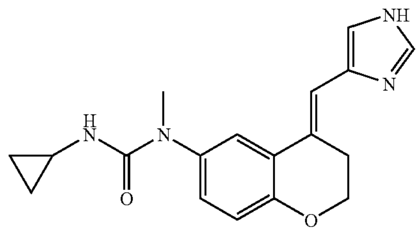 [SMILES: CN(C(=O)NC1CC1)c1ccc2c(c1)/C(=C/c1c[nH]cn1)CCO2] | 325 |
| 136 | 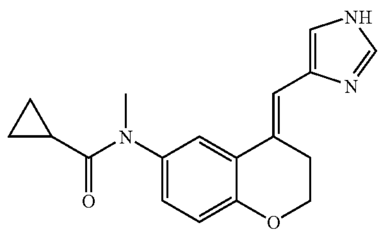 [SMILES: CN(C(=O)C1CC1)c1ccc2c(c1)/C(=C/c1c[nH]cn1)CCO2] | 310 |
| 137 | 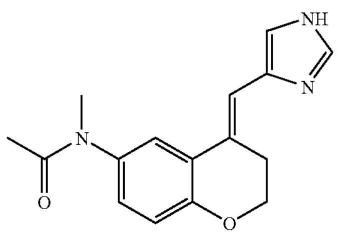 [SMILES: CC(=O)N(C)c1ccc2c(c1)/C(=C/c1c[nH]cn1)CCO2] | 284 |
| 138 | 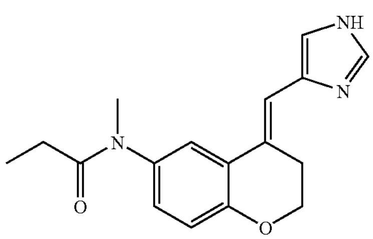 [SMILES: CCC(=O)N(C)c1ccc2c(c1)/C(=C/c1c[nH]cn1)CCO2] | 298 |
| 139 | 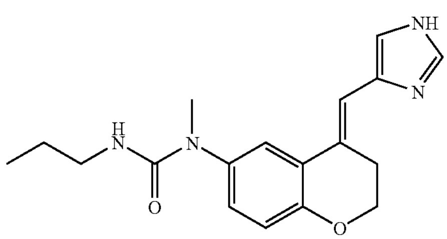 [SMILES: CCCNC(=O)N(C)c1ccc2c(c1)/C(=C/c1c[nH]cn1)CCO2] | 327 |
| 140 | 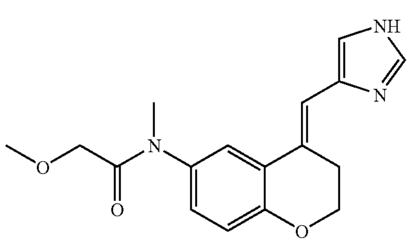 [SMILES: COCC(=O)N(C)c1ccc2c(c1)/C(=C/c1c[nH]cn1)CCO2] | 314 |

-continued

| Cpd | Structure | Spectral Data MS (MH+) unless noted |
|---|---|---|
| 141 | 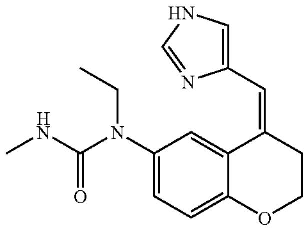 [SMILES: CCN(C(=O)NC)c1ccc2c(c1)/C(=C\c1c[nH]cn1)CCO2] | ¹H NMR (CD₃OD): 7.61 (s, 1H), 7.21 (s, 1H), 7.08 (s, 1H), 6.96 (dd, 1H), 6.87 (d, 1H), 6.26 (s, 1H), 4.40 (t, 2H), 3.49 (q, 2H), 2.65 (t, 2H), 2.64 (s, 3H), 0.98 (t, 3H) |
| 142 | 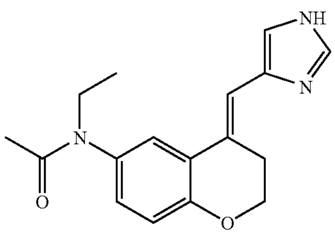 [SMILES: CCN(C(C)=O)c1ccc2c(c1)/C(=C/c1c[nH]cn1)CCO2] | 298 |
| 143 | 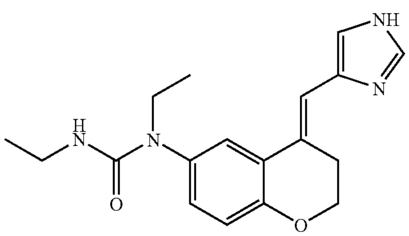 [SMILES: CCNC(=O)N(CC)c1ccc2c(c1)/C(=C/c1c[nH]cn1)CCO2] | 327 |
| 144 | 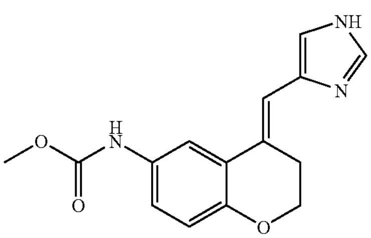 [SMILES: COC(=O)Nc1ccc2c(c1)/C(=C/c1c[nH]cn1)CCO2] | 286 |
| 145 | 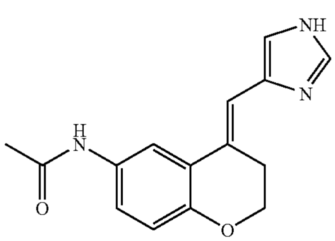 [SMILES: CC(=O)Nc1ccc2c(c1)/C(=C/c1c[nH]cn1)CCO2] | 270 |
| 146 | 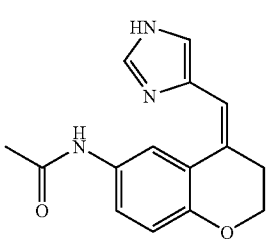 [SMILES: CC(=O)Nc1ccc2c(c1)/C(=C\c1c[nH]cn1)CCO2] | 270 |

-continued

| Cpd | Structure | Spectral Data MS (MH+) unless noted |
|---|---|---|
| 147 | 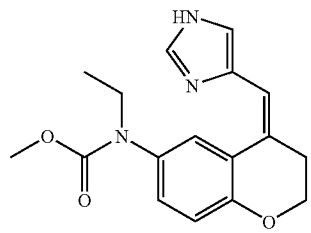 [SMILES: CCN(C(=O)OC)c1ccc2c(c1)/C(=C\c1c[nH]cn1)CCO2] | 314 |
| 148 | 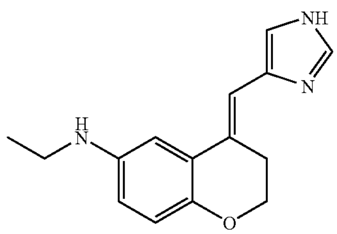 [SMILES: CCNc1ccc2c(c1)/C(=C/c1c[nH]cn1)CCO2] | 256 |
| 149 | 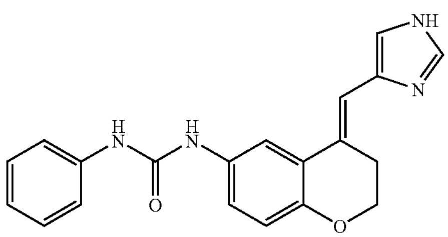 [SMILES: O=C(Nc1ccccc1)Nc1ccc2c(c1)/C(=C/c1c[nH]cn1)CCO2] | 347 |
| 150 | 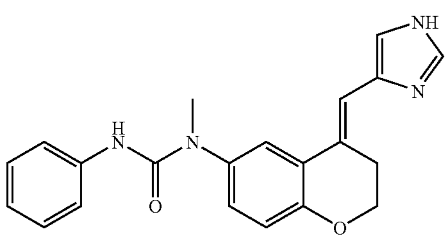 [SMILES: CN(C(=O)Nc1ccccc1)c1ccc2c(c1)/C(=C/c1c[nH]cn1)CCO2] | 361 |
| 151 | 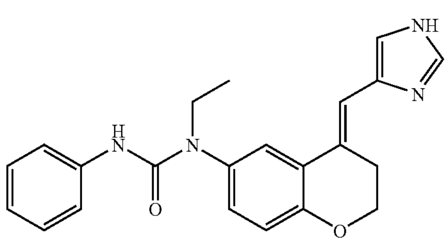 [SMILES: CCN(C(=O)Nc1ccccc1)c1ccc2c(c1)/C(=C/c1c[nH]cn1)CCO2] | 375 |
| 152 | 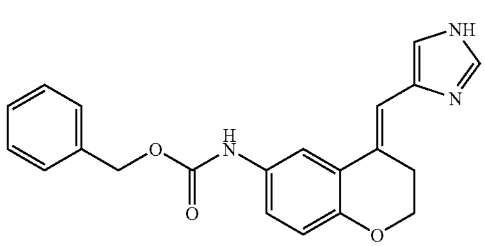 [SMILES: O=C(Nc1ccc2c(c1)/C(=C/c1c[nH]cn1)CCO2)OCc1ccccc1] | 362 |

-continued

| Cpd | Structure | Spectral Data MS (MH+) unless noted |
|---|---|---|
| 153 | 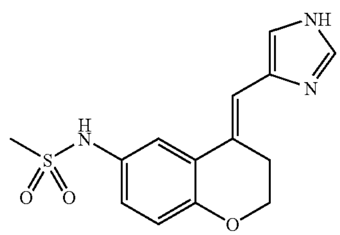 [SMILES: CS(=O)(=O)Nc1ccc2c(c1)/C(=C/c1c[nH]cn1)CCO2] | 306 |
| 154 | 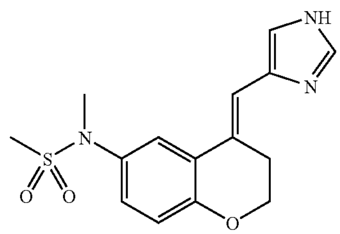 [SMILES: CN(c1ccc2c(c1)/C(=C/c1c[nH]cn1)CCO2)S(C)(=O)=O] | 320 |
| 155 | 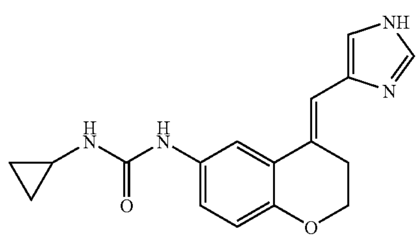 [SMILES: O=C(Nc1ccc2c(c1)/C(=C/c1c[nH]cn1)CCO2)NC1CC1] | 311 |
| 156 | 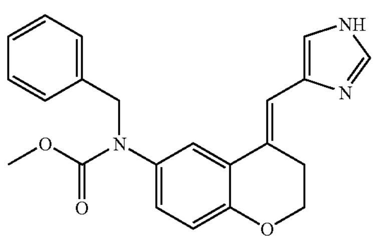 [SMILES: COC(=O)N(Cc1ccccc1)c1ccc2c(c1)/C(=C/c1c[nH]cn1)CCO2] | 376 |
| 157 | 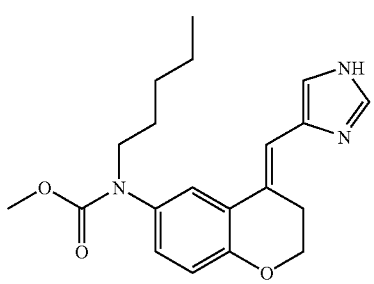 [SMILES: CCCCCN(C(=O)OC)c1ccc2c(c1)/C(=C/c1c[nH]cn1)CCO2] | 356 |
| 158 | 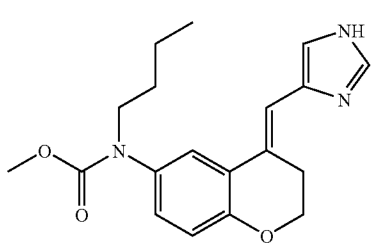 | 342 |

| Cpd | Structure | Spectral Data MS (MH+) unless noted |
|---|---|---|
| 159 | 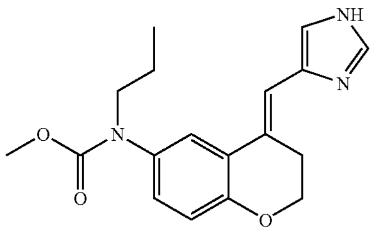 [SMILES: CCCN(C(=O)OC)c1ccc2c(c1)/C(=C/c1c[nH]cn1)CCO2] | 328 |
| 160 | 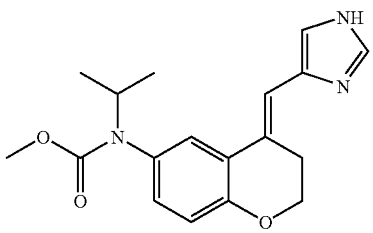 [SMILES: COC(=O)N(c1ccc2c(c1)/C(=C/c1c[nH]cn1)CCO2)C(C)C] | 328 |

The compounds of this invention may also be prepared through the approach outlined in the general schemes provided below. These schemes are being provided to illustrate the present invention.

Aza compounds of formula G1 can be prepared using the synthetic approach described in General Scheme 1. 2-Bromo-3-pyridinol reacts with alcohol G2 under Mitsunobu conditions to afford the intermediate G3, which undergoes intramolecular Heck cyclization to give pyridyl alkene intermediate G4. Dihydroxylation facilitated by osmium tetraoxide, and subsequent oxidative cleavage under sodium periodate conditions provides the ketone product G5. Compound G5 is then reduced using sodium borohydride, and converted subsequently to the corresponding bromide G7 using phosphorous tribromide. Oxidation of G7 by treatment with MCPBA affords N-oxide G8. The N-oxide G8 reacts with an imidoyl chloride, generated in situ from an amide and oxalyl chloride, mediated by 2,6-lutidine, to provide the intermediate G9. Under the refluxing conditions, G9 reacts with triphenylphosphine to form the phosphine salt G10. Under Wittig reaction conditions, such as those mediated by PhLi or LHMDS, phosphine salt G10 reacts with an aldehyde, for example 1-trityl-4-imidazole carboxaldehyde, to form the alkene adduct G11. The acetamide is removed via hydrolysis under heating condition (e.g. NaOH, EtOH, microwave heating) to generate amine G12, which would react with a variety of electrophiles under mild basic condition to afford advanced intermediate G13. Removal of trityl protection and hydrogenolysis will transform G13 to the aza compounds of formula G1.

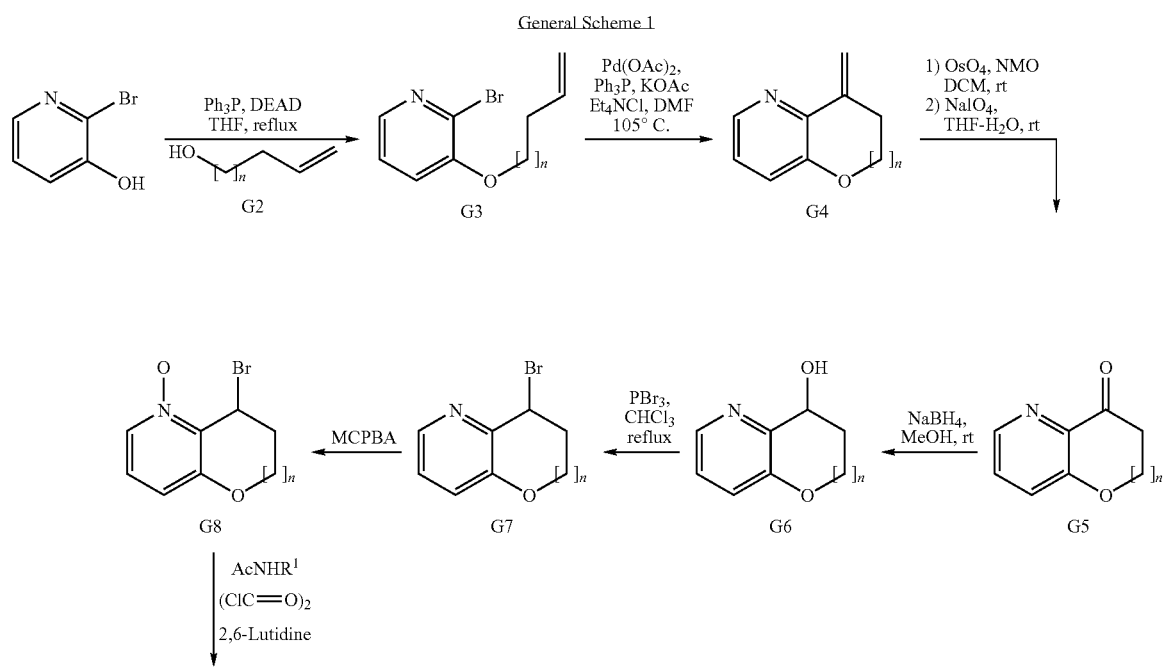

General Scheme 1

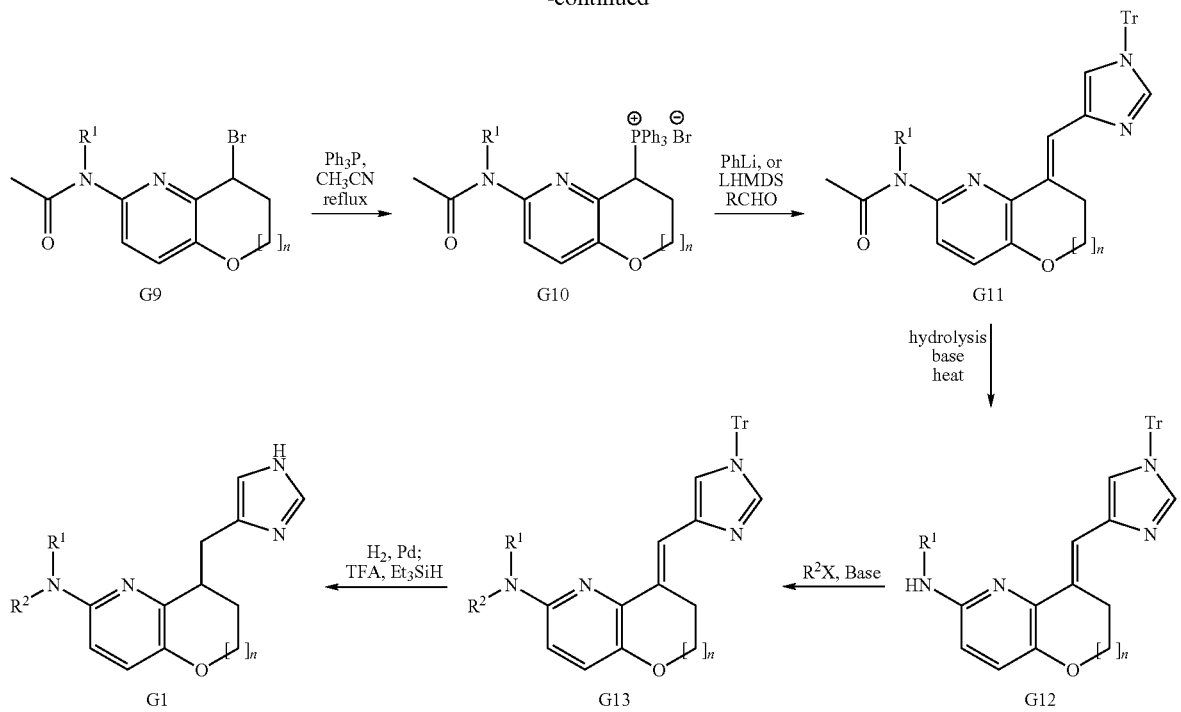

According to another embodiment wherein R¹ is a benzyl group, intermediate G12 can be converted to 2-amino-pyridine G14 under the hydrogenation conditions mediated by palladium hydroxide on carbon and with a catalytic amount of TFA for a few hours. Amino-pyridine G14 is reacted with phosgene at low temperature, and further elaborated to intermediate G15 by quenching the reaction with various alcohols (R³OH) and amines (R³NH₂). Direct removal of trityl group from G15 affords aza-compounds of formula G17 where R⁴ is H. Alternatively, intermediate G15 is alkylated with a variety of electrophiles R⁴X under mild basic conditions to afford G16. Removal of the trityl protection generates aza compounds of formula G17.

General Scheme 2

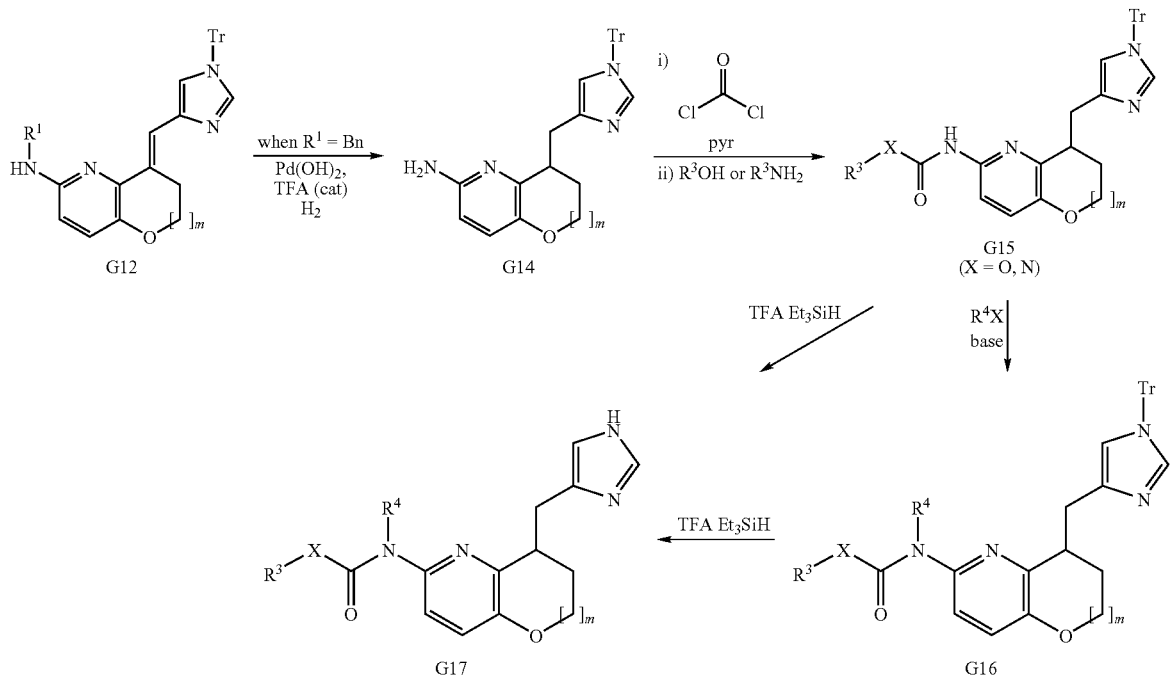

Preparative Example 200

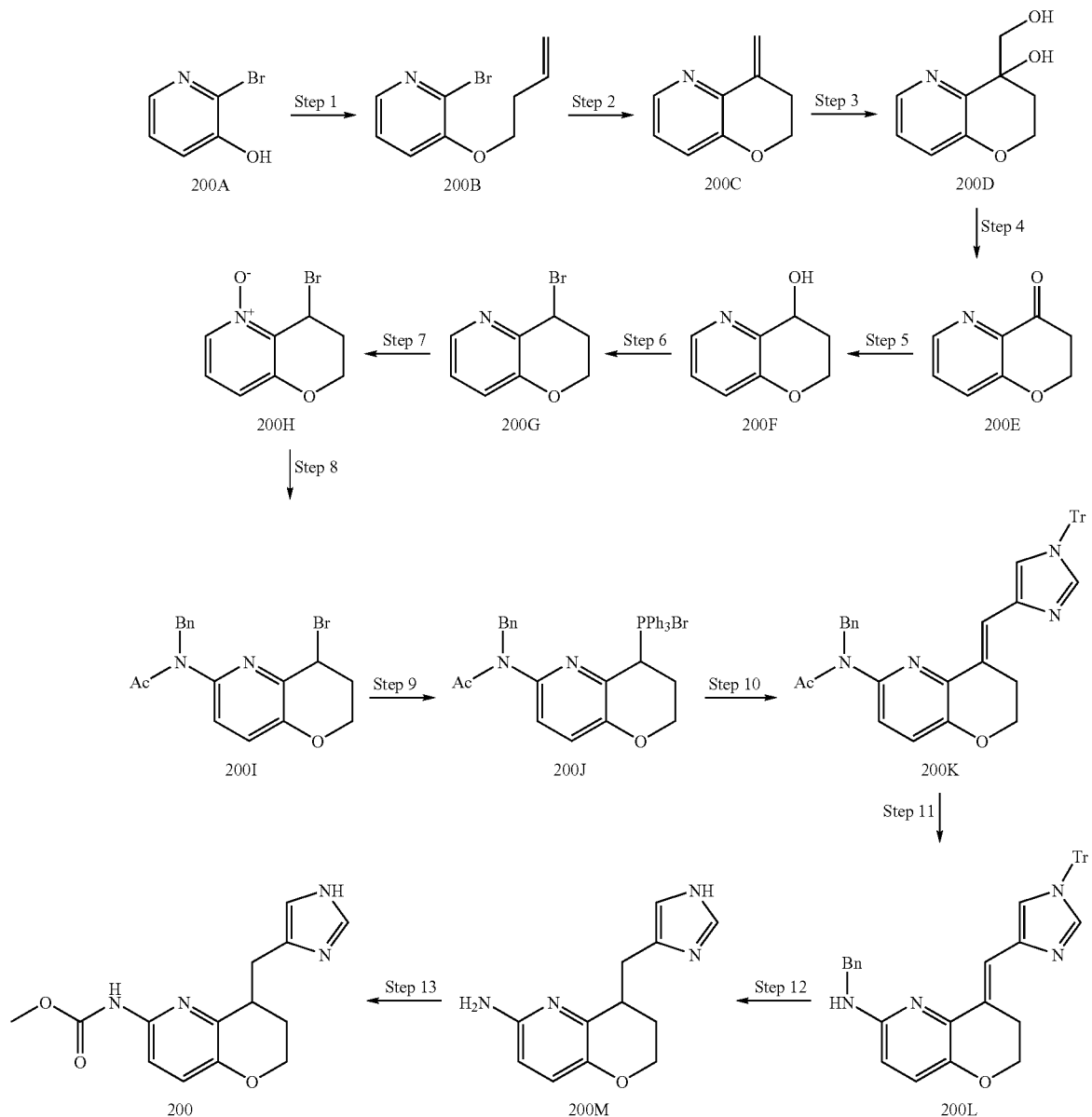

Step 1

To a stirred mixture of 2-bromo-3-pyridinol (20 g, 115 mmol, 200A) and 3-butenol (10 mL, 117 mmol) in 460 mL of anhydrous THF at 0° C. was added triphenylphosphine (36.14 g, 138 mmol) followed by diethylazodicarboxylate (19.9 mL, 126.4 mmol). The cooling bath was removed after 10 min. The mixture was heated at reflux overnight, and then concentrated in vacuo to dark brown oil. The oil was dissolved in 500 mL of ethyl acetate, washed with a sat. $NaHCO_3$ aq. solution and brine, dried with $Na_2SO_4$, and concentrated in vacuo to a mixture of oil and solid. The crude product mixture was dissolved in ~120 mL of $CH_2Cl_2$; the white solid was removed by filtration. The filtrate was purified by flash column chromatography eluting with 10% ethyl acetate in hexanes to afford 18.76 g of 200B (72%) as a near colorless oil.

Step 2

A solid mixture of triphenylphosphine (6.48 g, 24.7 mmol), palladium acetate (1.85 g, 8.22 mmol), potassium acetate (40.36 g, 411.2 mmol), and tetraethylammonium chloride hydrate (27.26 g, 164.5 mmol) in a sealed flask fitted with a septum was degassed via house vacuum and refilled with $N_2$. A solution of pyridyl bromide 200B (18.76 g, 82.246 mmol) in 330 mL of anhydrous DMF was added. The mixture was degassed again, and refilled with $N_2$. The septum was quickly replaced by a standard stopper, and the flask was sealed. The mixture was heated at 105° C. overnight. After cooling to room temperature, the mixture was poured into 500 mL of $H_2O$, extracted with ethyl acetate (400 mL×3). The combined organic extracts were filtered, and then washed with $H_2O$ then brine. The organic solution was dried over $Na_2SO_4$, concentrated to a dark brown oil, which was purified by flash column chromatography eluting with 5% ethyl acetate in hexanes to afford 7.75 g of pyridyl alkene 200C (64%) as a light yellow oil.

Step 3

To a stirred solution of pyridyl alkene 200C (7.75 g, 52.66 mmol) in 150 mL of $CH_2Cl_2$ at room temperature was added N-methyl-morpholinoxide (NMO, 18.5 g, 158 mmol). A 2.5 wt % solution of osmium tetraoxide in tert-butanol (14 mL, ~1.05 mmol) was added drop wise. The mixture was stirred overnight and then diluted with 200 mL of ethyl acetate. The small amount of solid precipitate present was removed via filtration through a celite pad. The filtrate was concentrated in vacuo to a dark brown oil, purified by flash column chromatography (eluting with $CH_2Cl_2$, $CH_2Cl_2$-7N $NH_3$ in MeOH, 25:1, v/v) to afford 10.39 g of diol 200D (~100%) as a yellow oil.

Step 4

Diol 200D (9.54 g, 52.66 mmol) was dissolved in 100 mL of THF and 100 mL of $H_2O$, Sodium periodate (33.73 g, 158.0 mmol) was added. The mixture was stirred for 2.5 h at room temperature. A sat. $NaHCO_3$ aq. solution was added (~400 mL); the mixture was further diluted with $H_2O$, and extracted with $CH_2Cl_2$ (400 mL×3). The organic extracts were filtered through a celite pad, and then washed with $H_2O$ and brine. The organic solution was dried with $Na_2SO_4$, and concentrated in vacuo to give 6.02 g of the ketone 200E (77% over two steps) as a light yellow solid.

Step 5

Sodium borohydride (2.29 g, 60.52 mmol) was added to a stirred solution of ketone 200E (6.02 g, 40.364 mmol) in 200 mL of methanol at room temperature. The mixture was stirred overnight. 200 mL of water was added, stirring was continued for 30 min. The mixture was concentrated in vacuo, and extracted with $CH_2Cl_2$ (200 mL×3). The combined organic extracts were washed with brine, dried over $Na_2SO_4$, and concentrated in vacuo to an oil, solidified on standing, providing 5.5 g of alcohol 200F (90%) as a yellow solid.

Step 6

Phosphorous tribromide (5.2 mL, 55.13 mmol.) was added drop wise to a stirred solution of alcohol 200F (5.5 g, 36.386 mmol) in 200 mL of $CHCl_3$. The mixture was heated at reflux for 3.5 h, cooled to room temperature, poured into a mixture of ice and sat. $NaHCO_3$ aq. solution (~400 mL). The aqueous mixture was separated and the aqueous layer was extracted with $CH_2Cl_2$ (300 mL×2). The combined organic extracts were washed with $H_2O$, sat. $NaHCO_3$, and brine. The organic solution was dried with $Na_2SO_4$, filtered, and concentrated in vacuo to give 7.63 g of bromide 200G (98%) as dark pinkish oil.

Step 7

To a stirred solution of bromide 200G (3.0 g, 14.02 mmol) in 140 mL of $CH_2Cl_2$ at 0° C. was added MCPBA (3.93 g, 17.535 mmol). Reaction mixture was stirred overnight while temperature was increased to room temperature. A sat. $NaHCO_3$ aq. solution was added. The layers were separated. The aqueous layer was extracted with $CH_2Cl_2$ (100 mL×2). The combined organic extracts were washed with a sat. $NaHCO_3$ aq. solution and brine, dried over $Na_2SO_4$, and concentrated in vacuo to give 3.34 g (quantitative) of the N-oxide 200H as a yellow oil.

Step 8

To a stirred solution of N-benzylacetamide (3.12 g, 20.92 mmol) in 40 mL of $CH_2Cl_2$ at 0° C. was added 2,6-lutidine (4 mL, 37.454 mmol) followed by dropwise addition of oxalyl chloride (1.82 mL, 20.86 mmol). After 30 min, a solution of N-oxide 200H (3.2 g, 13.91 mmol) in 30 mL of $CH_2Cl_2$ was added dropwise. Cooling bath was removed; reaction was continued at room temperature for 2.5 g, and quenched with a sat. $NaHCO_3$ aqueous solution. The aqueous mixture was extracted with $CH_2Cl_2$ (100 mL×3). The combined organic extracts were washed with sat. $NaHCO_3$, $H_2O$, and brine. The organic solution was dried with $Na_2SO_4$, filtered, and concentrated in vacuo to a dark brown oil, which was separated by flash column chromatography eluting with ethyl acetate in $CH_2Cl_2$ (20%, and then 30%) to afford 2.72 g of bromide 200I (54%) as a dark yellow oil.

Step 9

To a stirred solution of bromide 200I (2.72 g, 7.53 mmol) in 40 mL of acetonitrile was added triphenylphosphine (1.88 g, 7.17 mmol). The mixture was heated at reflux for 2.5 d. Solvent was removed in vacuo. The oily residue was dried on high vacuum overnight, afforded 4.56 g of phosphine salt 200J (97%) as a brown solid.

Step 10

To a stirred solution of phosphine salt 200J (3.23 g, 5.18 mmol) in 30 mL of THF at −78° C. was added dropwise a 1.0 M solution of LHMDS in THF (6.2 mL, 6.2 mmol). The mixture was stirred for 2.5 h while temperature was maintained at −78° C. for the first 2 h and increased to −65° C. for the next 30 min. A solution of 1-trityl-4-imidazole carboxaldehyde (2.1 g, 6.20 mmol) in 20 mL of THF was added dropwise. Reaction was continued for 3.5 h as temperature of the cooling bath was gradually increased to −10° C. Cooling bath was removed. Reaction was continued overnight, and quenched with a sat. $NaHCO_3$ aq. solution. The aqueous mixture was concentrated in vacuo, extracted with $CH_2Cl_2$ (70 mL×3). The combined organic extracts were washed with brine, dried over $Na_2SO_4$, and concentrated in vacuo to a dark brown oily residue, purified by flash column chromatography, eluting with ethyl acetate in $CH_2Cl_2$ (10%, 15%, v/v) to afford 792 mg of alkenyl product 200K (25%) as a light yellow fluffy solid.

Step 11

Alkenyl product 200K (789 mg, 1.3 mmol) was dissolved in 10 mL of ethanol and treated with sodium hydroxide (210 mg, 5.25 mmol). The mixture was heated in a microwave oven at 120° C. for 25 min. After cooling, the mixture was concentrated in vacuo to an oily solid residue, which was partitioned between $CH_2Cl_2$ and brine. The layers were separated, the aqueous layer was extracted with $CH_2Cl_2$ (2×). The combined organic layers were washed with brine, dried over $Na_2SO_4$, and filtered. The filtrate was concentrated in vacuo to give 780 mg of pyridyl benzyl amine 200L (crude, quantitative) as a yellow solid.

Step 12

To a nitrogen flushed solution of benzyl amine 200L (780 mg) in 15 mL of methanol was added 20% palladium hydroxide on carbon (wet with 50% $H_2O$, 750 mg). 0.1 mL of trifluoroacetic acid was added. The mixture was degassed via house vacuum, and refilled with $H_2$ from a gas balloon. Reaction was continued overnight. The mixture was diluted with methanol and $CH_2Cl_2$, filtered through a celite pad. The filtrate was concentrated in vacuo to an oily solid, purified by preparative TLC ($CH_2Cl_2$-7 N $NH_3$ in MeOH=20:1, v/v) to give 174 mg of 2 amino-pyridine 200M (58% over two steps) as a near colorless glassy solid.

Step 13

To a stirred solution of 2-amino-pyridine 200M (110 mg, 0.4777 mmol) in 7 mL of $CH_2Cl_2$ at −78° C. was added pyridine (0.11 mL, 1.36 mmol) followed by dropwise addition of a 20 wt % solution of phosgene in toluene (0.38 mL, 0.722 mmol). The mixture was stirred for 45 min while temperature was slightly increased to −60° C. 4 mL of methanol was added. The mixture was stirred overnight, quenched with a sat. NaHCO₃ aq. solution. The aqueous mixture was concentrated in vacuo, extracted with CH₂Cl₂ (50 mL×3). The combined organic extracts were washed with brine, dried over Na₂SO₄, and concentrated in vacuo to an oily solid, which was purified by flash column chromatography eluting with MeOH (containing 0.1% NEt₃) in CH₂Cl₂ (5% and 10%, v/v) to afford 73 mg of the titled product 200 (53%) as a glassy solid. LMCS m/z 289 (MH⁺).

Preparative Example 201 hydrolyzed to provided the N-ethyl-N-pyridyl amine 201D (30 mg, 14%).

Step 5

Following a similar procedure described in Example 200 (Step 13), amine 201D (30 mg, 0.0602 mmol) was converted to the methyl carbamate 201E (80 mg, crude, quantitative).

Step 6

To a nitrogen flushed solution of carbamate 201E (80 mg, ~0.0602 mmol) in 2 mL of MeOH and 3 drops of trifluoro-

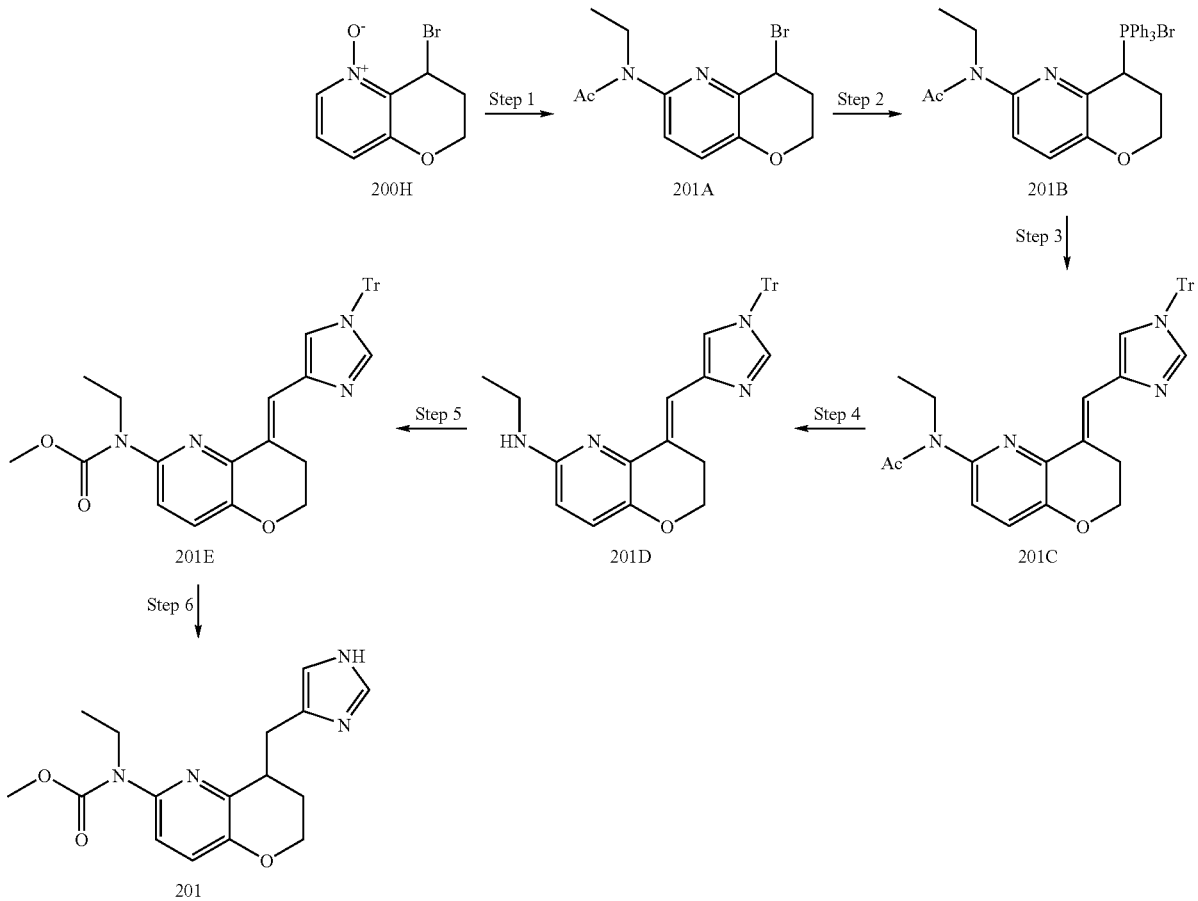

Step 1

N-oxide 200H (2.176 g, 9.46 mmol, available from Example 200, Step 7), was converted to N-ethyl-acetamide 201A (0.995 g, 35%) in a manner similar to that described in Example 200 (Step 8).

Step 2

N-ethyl acetamide 201A (0.995 g, 3.326 mmol) was heated with triphenylphosphine (0.873 g, 3.328 mmol) in 30 mL of acetonitrile at reflux for 1 d. Solvent was removed in vacuo to afford 1.83 g of phosphine salt 201B (98%).

Step 3

Following a similar procedure described in Example 200 (Step 10), phosphine salt 201B (1.2 g, 2.137 mmol) was converted to alkene product 201C (0.234 g, 20%, light yellow glassy solid).

Step 4

Following a similar procedure described in Example 200 (Step 11), alkene compound 201C (234 mg, 0.433 mmol) was acetic acid was added 20% palladium hydroxide on carbon (30 mg). The mixture was stirred over two days at room temperature, and then diluted with methanol and CH₂Cl₂. The mixture was filtered through a celite pad, rinsing with methanol. The filtrate was concentrated in vacuo to an oily residue.

The oily residue from above was dissolved in 2 mL of methanol, and degassed via house vacuum. 10% Palladium on carbon (20 mg) was added. The mixture was degassed again, and refilled with H₂ from a gas balloon. Reaction was continued for 2 d. The mixture was diluted with methanol and CH₂Cl₂, filtered through a celite pad. The filtrated was concentrated, purified by preparative TLC(CH₂Cl₂-7N NH₃ in MeOH=25; 1, v/v) to afford 10 mg of the titled product 201 (53% over two steps) as an off white solid. LMCS m/z 317 (MH⁺).

Assay:

Efficacy agonist activity values (Emax, GTPγS assay) for α2A and α2C were determined by following the general procedure detailed by Umland et. al ("Receptor reserve analysis of the human $\alpha_{2c}$-adrenoceptor using [$^{35}$S]GTPγS and cAMP functional assays" European Journal of Pharmacology 2001, 411, 211-221). For the purposes of the present invention, a compound is defined to be a specific or at least selective agonist of the α2C receptor subtype if the compound's efficacy at the α2C receptor is ≧30% Emax (GTPγS assay) and its efficacy at the α2A receptor is ≦35% Emax (GTPγS assay).

The following compounds were evaluated to be specific or at least selective agonists of the α2C receptor subtype based on the previously defined definition: 1, 5, 7, 16, 47, 48, 49, 50, 51, 55, 58, 62, 63, 64, 65, 67, 113, 115, 119, 120, 121, 122, 123, 128, 132, 134, 140, 142, 143, 144 and 152.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. The following compounds:

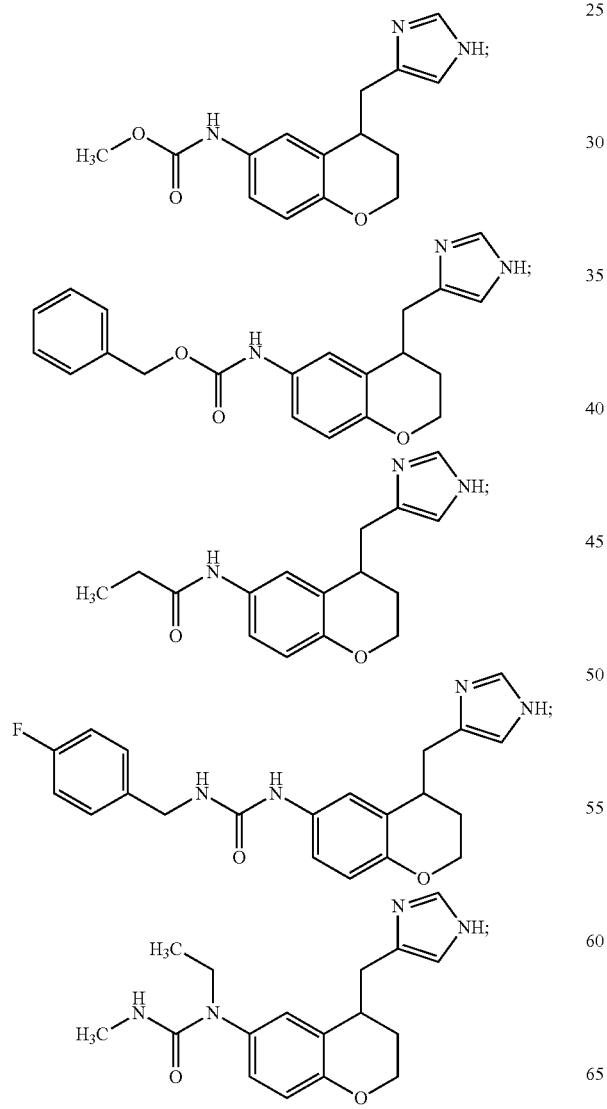

-continued

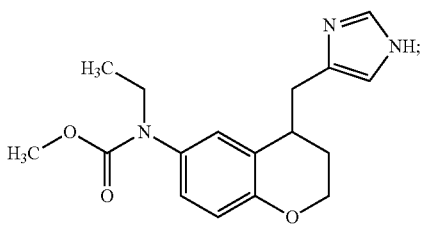

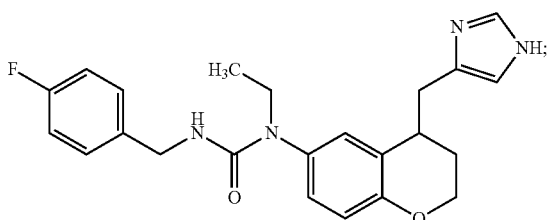

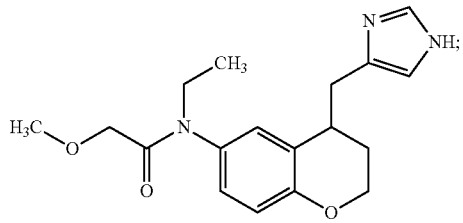

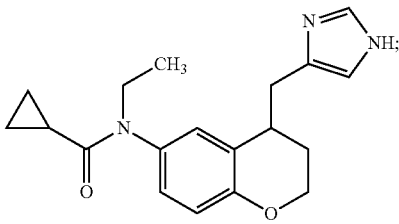

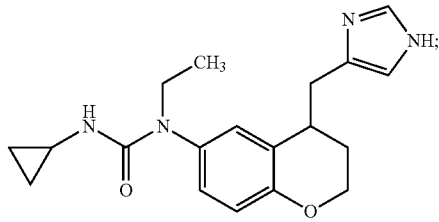

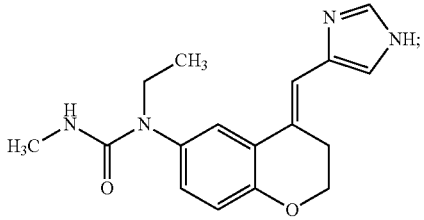

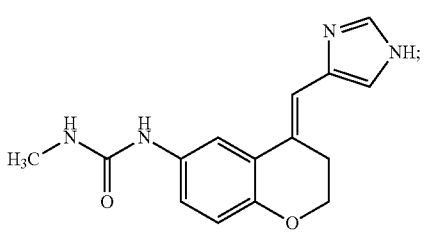

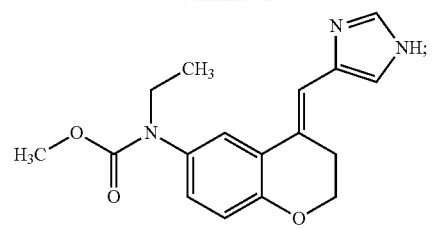
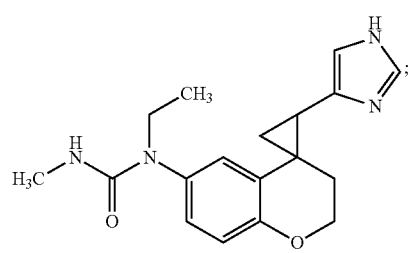
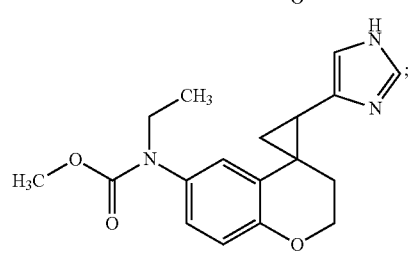
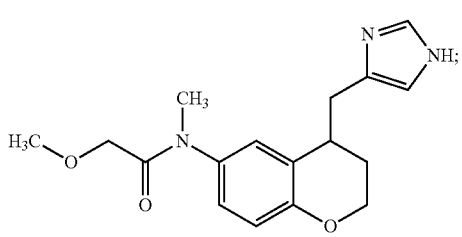
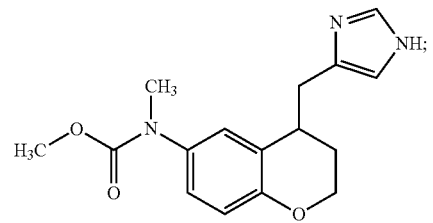
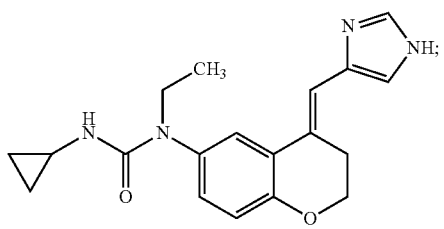
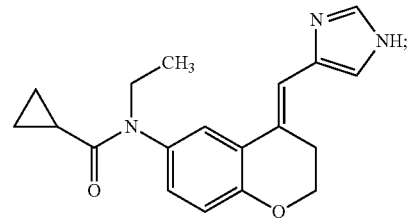
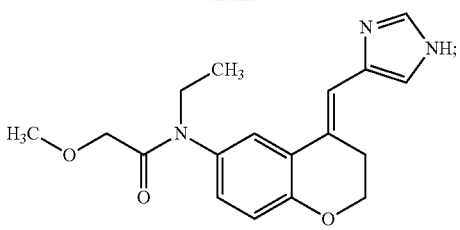
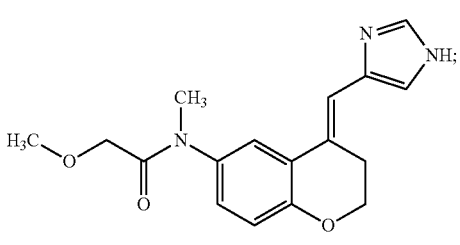
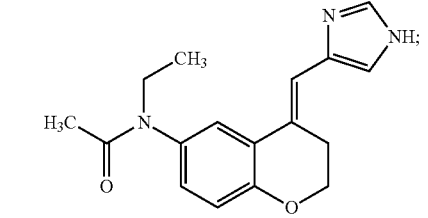
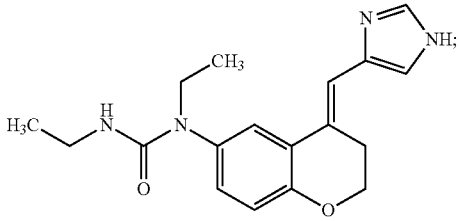
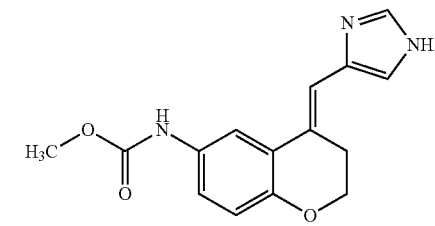
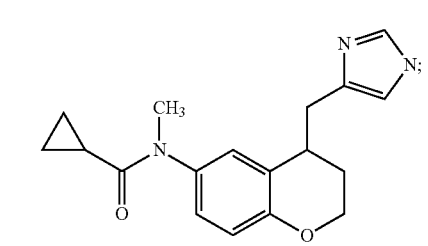
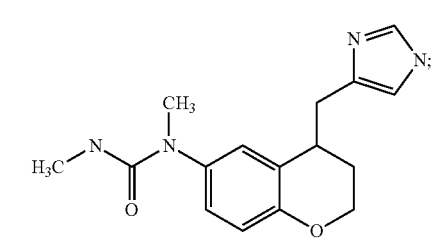

-continued

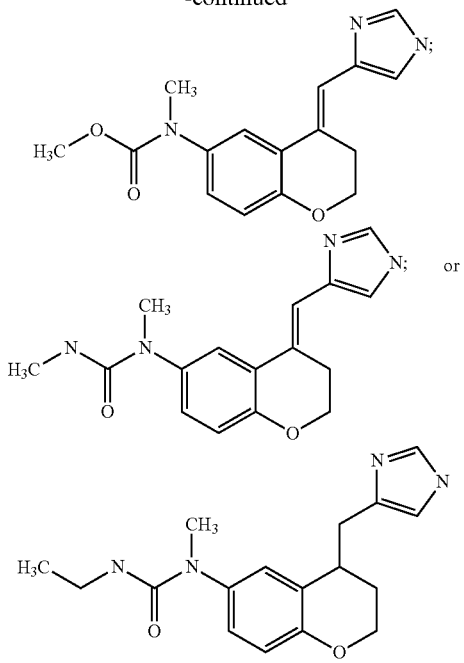

or a pharmaceutically acceptable salt thereof.

2. A pharmaceutical composition comprising at least one compound of claim 1, or a pharmaceutically acceptable salt thereof and at least one pharmaceutically acceptable carrier, adjuvant or vehicle.

3. The pharmaceutical composition of claim 2, further comprising one or more additional therapeutic agents, wherein said additional therapeutic agents are selected from the group consisting of steroids, glucocorticosteroids, PDE-4 inhibitors, anti-muscarinic agents, muscle relaxants, cromolyn sodium, $H_1$ receptor antagonists, $5-HT_1$ agonists, NSAIDs, angiotensin-converting enzyme inhibitors, angiotensin 11 receptor agonists, β-blockers, long and short acting β-agonists, leukotriene antagonists, diuretics, aldosterone antagonists, ionotropic agents, natriuretic peptides, pain management/analgesic agents, anti-anxiety agents, anti-migraine agents, sedatives, NMDA receptor antagonists, alpha-adrenergics not including alpha-1 receptor antagonists, anti-convulsants, tachykinin (NK) antagonists, COX-2 inhibitors, neuroleptics, vanilloid receptor agonists or antagonists, beta-adrenergics, local anaesthetic, corticosteroids, serotonin receptor agonists or antagonists, PDEV inhibitors, alpha-2-delta ligands, canabinoids and therapeutic agents suitable for treating heart conditions, psychotic disorders, or glaucoma.

4. A method of treating a condition selected from allergic rhinitis, congestion, pain, diarrhea, glaucoma, congestive heart failure, chronic heart failure, cardiac ischemia, manic disorders, depression, anxiety, migraine, stress-induced urinary incontinence, neuronal damage from ischemia, schizophrenia, attention deficit hyperactivity disorder, and symptoms of diabetes comprising administering to a mammal in need of such treatment a compound of claim 1 or a pharmaceutically acceptable salt thereof.

5. The method of claim 4, wherein the condition is congestion is associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis.

6. The method of claim 4, wherein the condition is congestion caused by polyps or the common cold.

7. The method of claim 4, wherein the condition is pain.

8. The method of claim 4, wherein the pain is associated with neuropathy, inflammation, arthritis, diabetes.

9. A compound of claim 1, in isolated and purified form.

10. A compound of claim 1, having the formula:

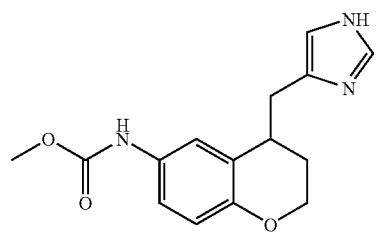 [SMILES: COC(=O)Nc1ccc2c(c1)C(Cc1c[nH]cn1)CCO2]

or a pharmaceutically acceptable salt thereof.

11. A compound of claim 1, having the formula:

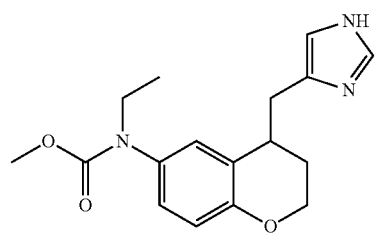 [SMILES: CCN(C(=O)OC)c1ccc2c(c1)C(Cc1c[nH]cn1)CCO2]

or a pharmaceutically acceptable salt thereof.

12. A compound of claim 1, having the formula:

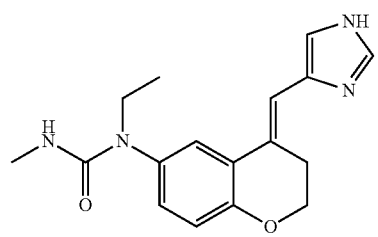 [SMILES: CCN(C(=O)NC)c1ccc2c(c1)/C(=C/c1c[nH]cn1)CCO2]

or a pharmaceutically acceptable salt thereof.

13. A compound of claim 1, having the formula:

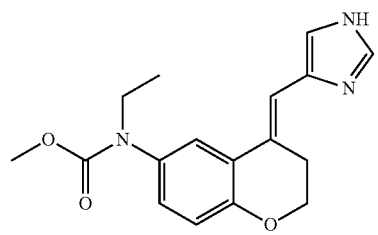 [SMILES: CCN(C(=O)OC)c1ccc2c(c1)/C(=C/c1c[nH]cn1)CCO2]

or a pharmaceutically acceptable salt thereof.

14. A compound of claim 1, having the formula:
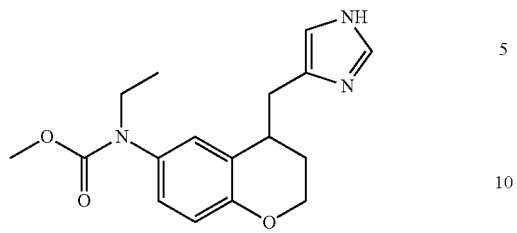
or a pharmaceutically acceptable salt thereof.
* * * * *